(12) United States Patent
Knust et al.

(10) Patent No.: US 7,592,345 B2
(45) Date of Patent: Sep. 22, 2009

(54) PIPERAZINE AND [1,4]DIAZEPAN DERIVATIVES AS NK ANTAGONISTS

(75) Inventors: Henner Knust, Rheinfelden (DE); Matthias Nettekoven, Grenzach-Wyhlen (DE); Hasane Ratni, Habsheim (FR); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/132,002

(22) Filed: Jun. 3, 2008

(65) Prior Publication Data

US 2008/0312216 A1 Dec. 18, 2008

(30) Foreign Application Priority Data

Jun. 13, 2007 (EP) .................. 07110143

(51) Int. Cl.
*A61K 31/497* (2006.01)
(52) U.S. Cl. .................. 514/252.13; 544/353; 546/348
(58) Field of Classification Search ............ 514/252.13; 544/353; 546/348
See application file for complete search history.

(56) References Cited

FOREIGN PATENT DOCUMENTS

WO WO 02/38548 5/2002

OTHER PUBLICATIONS

Tooney et al., Neurosci. Letters, vol. 283 pp. 185-188 (2000).
Giardina et al., Exp. Opin. Ther. Patents vol. 10, pp. 939-960 (2000).
Jung et al., Neuroscience vol. 74 pp. 403-414 (1996).
Marco et al., Neuropeptides vol. 32, pp. 481-488 (1998).
Kamali, F., Current Opinion in Investigational Drugs, vol. 2(7) pp. 950-956 (2001).
Clark et al. Journal of Medicinal Chemistry, vol. 26(5), pp. 657-661 (1983).

*Primary Examiner*—James O Wilson
*Assistant Examiner*—Douglas M Willis
(74) *Attorney, Agent, or Firm*—George W. Johnston; Patricia S. Rocha-Tramaloni; Kimberly J. Prior

(57) ABSTRACT

The present invention relates to a compound of formula I

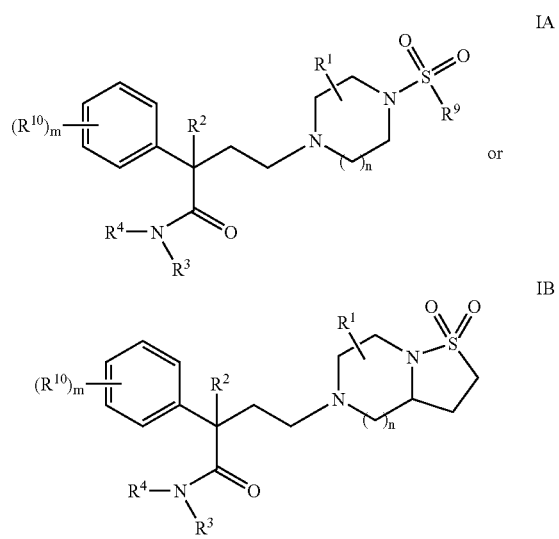

wherein
$R^1$, $R^2$, $R^3$, $R^4$,
$R^9$, $R^{10}$, m and n are as defined herein, or to a pharmaceutically acceptable acid addition salt thereof. The present compounds are high potential NK-3 receptor antagonists for the treatment of depression, bipolar disorders, pain, psychosis, Parkinson's disease, schizophrenia, anxiety and attention deficit hyperactivity disorder (ADHD).

24 Claims, No Drawings

PIPERAZINE AND [1,4]DIAZEPAN DERIVATIVES AS NK ANTAGONISTS

PRIORITY TO RELATED APPLICATION(S)

This application claims the benefit of European Patent Application No. 07110143.0, filed Jun. 13, 2007, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH— terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Resources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956 and *Psychiatric Disorders Study* 4, *Schizophrenia*, June 2003, Decision Resources, Inc., Waltham, Mass.).

SUMMARY OF THE INVENTION

The present invention provides a compound of formula I

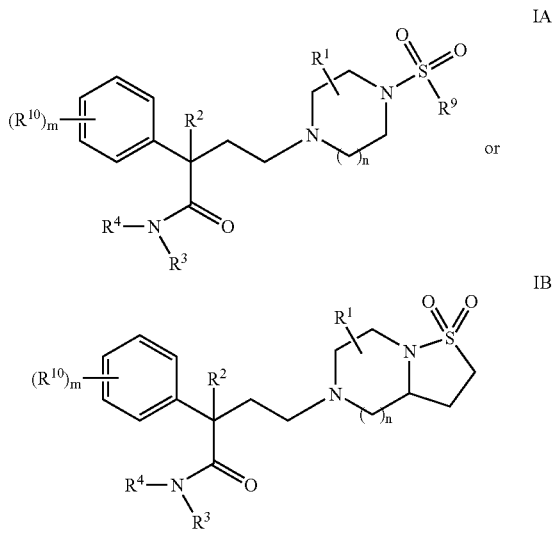

wherein
$R^1$ is hydrogen or lower alkyl;
$R^2$ is hydrogen, fluoro, hydroxy or lower alkyl;
$R^3$ is hydrogen or lower alkyl;
$R^4$ is —CHR$^5$-A
  $R^5$ is hydrogen, lower alkyl, fluoro, CF$_3$, CH$_2$OH or cycloalkyl;
  A is aryl or heteroaryl, each of which is unsubstituted or substituted by (R$^6$)$_o$;
  $R^6$ is heteroaryl, lower alkyl, lower alkoxy, cyano, halogen, lower alkyl substituted by halogen, lower alkoxy substituted by halogen or NR$^7$R$^8$, wherein when o is more than one, each R$^6$ is the same or different;
  o is 1, 2 or 3;
  $R^7$ and $R^8$ are each independently hydrogen or lower alkyl;
$R^9$ is lower alkyl;

$R^{10}$ is lower alkyl, lower alkoxy or halogen;
n is 1 or 2;
m is 1 or 2;
or a pharmaceutically acceptable acid addition salt thereof.

The invention includes all sterioisomeric forms, including individual diastereoisomers and enantiomers of the compound of formula (I) as well as racemic and non-racemic mixtures thereof.

The invention also provides pharmaceutical compositions which contain a therapeutically effective compound of formula I or a pharmaceutically acceptable acid addition salt thereof and a pharmaceutically acceptable carrier. The invention further provides methods for the manufacture of the compounds and compositions of the invention.

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "halogen" denotes chlorine, iodine, fluorine and bromine.

The term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CF$_2$CF$_3$ and the like. Preferred lower alkyl substituted by halogen groups are groups having 1-4 carbon atoms.

The term "lower alkoxy" denotes a lower alkyl group as defined above that is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes a lower alkoxy group substituted by halogen as defined above that is attached via an oxygen atom. Preferred lower alkoxy substituted by halogen groups are groups having 1-4 carbon atoms.

The term "cycloalkyl" denotes a saturated carbon ring containing from 3-7 carbon atoms, for example, cyclopropyl, cyclobutyl, cyclopentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic radical consisting of one or more fused rings containing 3-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazinyl, pyrazolyl, pyridinyl, pyridyl, pyrimidyl, oxadiazolyl, triazolyl, tetrazolyl, thiazolyl, thiadiazolyl, thienyl, furyl or imidazolyl.

Preferred heteroaryl groups are quinoxalinyl and pyridinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following groups of compounds of formula IA are preferred:

A compound of formula IA, wherein n is 1.
A compound of formula IA, wherein $R^2$ is lower alkyl.
A compound of formula IA, wherein $R^3$ is hydrogen or lower alkyl and $R^4$ is —CHR$^5$-A. Preferably A is an optionally substituted aryl, and particularly A is an optionally substituted phenyl.

The following compounds relate to this group. N-(4-chloro-benzyl)-2-(3,4-dichloro-phenyl)-4-(4-methanesulfonyl-piperazin-1-yl)-2,N-dimethyl-butyramide, 2-(3,4-dichloro-phenyl)-N-(3-fluoro-4-trifluoromethyl-benzyl)-4-(4-methanesulfonyl-piperazin-1-yl)-2-methyl-butyramide, N-(3,4-dichloro-benzyl)-2-(3,4-dichloro-phenyl)-4-(4-methanesulfonyl-piperazin-1-yl)-2-methyl-butyramide, 2-(3,4-dichloro-phenyl)-4-(4-methanesulfonyl-piperazin-1-yl)-2,N-dimethyl-N-(4-methyl-benzyl)-butyramide, 2-(3,4-dichloro-phenyl)-4-(4-methanesulfonyl-piperazin-1-yl)-2-methyl-N-(4-trifluoromethyl-benzyl)-butyramide, 2-(3,4-dichloro-phenyl)-4-(4-methanesulfonyl-piperazin-1-yl)-2,N-dimethyl-N-(4-trifluoromethyl-benzyl)-butyramide, N-(4-chloro-benzyl)-2-(3,4-dichloro-phenyl)-4-(4-methanesulfonyl-piperazin-1-yl)-2-methyl-butyramide, N-[cyclopropyl-(4-methoxy-phenyl)-methyl]-2-(3,4-dichloro-phenyl)-4-((R)-4-methanesulfonyl-3-methyl-piperazin-1-yl)-2-methyl-butyramide, 2-(3,4-dichloro-phenyl)-N-(4-fluoro-3-trifluoromethyl-benzyl)-4-((R)-4-methanesulfonyl-3-methyl-piperazin-1-yl)-2,N-dimethyl-butyramide, N-(3,5-bis-trifluoromethyl-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2,N-dimethyl-N-(4-methyl-benzyl)-butyramide, N-(4-chloro-3-trifluoromethyl-benzyl)-2-(3,4-dichloro-phenyl)-4-((R)-4-methanesulfonyl-3-methyl-piperazin-1-yl)-2,N-dimethyl-butyramide, 2-(3,4-dichloro-phenyl)-N-(3-fluoro-4-trifluoromethyl-benzyl)-4-((R)-4-methanesulfonyl-3-methyl-piperazin-1-yl)-2,N-dimethyl-butyramide, N-(3,4-dichloro-benzyl)-2-(3,4-dichloro-phenyl)-4-((R)-4-methanesulfonyl-3-methyl-piperazin-1-yl)-2,N-dimethyl-butyramide, N-(3,4-dichloro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-N-(3-difluoromethoxy-benzyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(4-trifluoromethyl-benzyl)-butyramide, 2-(3,4-dichloro-phenyl)-N-(2-fluoro-5-trifluoromethyl-benzyl)-4-((R)-4-methanesulfonyl-3-methyl-piperazin-1-yl)-2-methyl-butyramide, N-[1-(4-chloro-phenyl)-ethyl]-2-(3,4-dichloro-phenyl)-4-((R)-4- methanesulfonyl-3-methyl-piperazin-1-yl)-2-methyl-butyramide, N-(2-chloro-benzyl)-2-(3,4-dichloro-phenyl)-4-((R)-4-methanesulfonyl-3-methyl-piperazin-1-yl)-2,N-dimethyl-butyramide, 2-(3,4-dichloro-phenyl)-N-[1-(3,4-dichloro-phenyl)-ethyl]-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(3-trifluoromethoxy-benzyl)-butyramide, N-(4-chloro-3-fluoro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(4-trifluoromethoxy-benzyl)-butyramide, N-(4-chloro-3-trifluoromethyl-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2,N-dimethyl-N-(4-trifluoromethyl-benzyl)-butyramide, N-(4-chloro-benzyl)-2-(3,4-dichloro-phenyl)-4-((R)-4-methanesulfonyl-3-methyl-piperazin-1-yl)-2,N-dimethyl-butyramide, 2-(3,4-dichloro-phenyl)-4-((R)-4-methanesulfonyl-3-methyl-piperazin-1-yl)-2,N-dimethyl-N-(3-trifluoromethyl-benzyl)-butyramide, N-[cyclopropyl-(4-methoxy-phenyl)-methyl]-2-(3,4-dichloro-phenyl)-4-((S)-4-methanesulfonyl-3-methyl-piperazin-1-yl)-2-methyl-butyramide, 2-(3,4-dichloro-phenyl)-N-(4-fluoro-3-trifluoromethyl-benzyl)-4-((S)-4-methanesulfonyl-3-methyl-piperazin-1-yl)-2,N-dimethyl-butyramide, N-(3,5-bis-trifluoromethyl-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2,N-dimethyl-N-(4-methyl-benzyl)-butyramide, N-(4-chloro-3-trifluoromethyl-benzyl)-2-(3,4-dichloro-phenyl)-4-((S)-4-methanesulfonyl-3-methyl-piperazin-1-yl)-2,N-dimethyl-butyramide, 2-(3,4-dichloro-phenyl)-N-(3-fluoro-4-trifluoromethyl-benzyl)-4-((S)-4-methanesulfonyl-3-methyl-piperazin-1-yl)-2,N-dimethyl-butyramide, N-(3,4-dichloro-benzyl)-2-(3,4-dichloro-phenyl)-4-((S)-4-methanesulfonyl-3-methyl-piperazin-1-yl)-2,N-dimethyl-butyramide, N-(3,4-dichloro-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2-methyl-N-(4-trifluoromethyl-benzyl)-butyramide, N-[1-(4-chloro-phenyl)-ethyl]-2-(3,4-dichloro-phenyl)-4-((S)-4-methanesulfonyl-3-methyl-piperazin-1-yl)-2-methyl-butyramide, 2-(3,4-dichloro-phenyl)-N-[1-(3,4-dichloro-phenyl)-ethyl]-4-((S)-4-methanesulfonyl-3-methyl-piperazin-1-yl)-2-methyl-butyramide, N-(4-chloro-3-fluoro-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2-methyl-N-(4-trifluoromethoxy-benzyl)-butyramide, N-(4-chloro-3-trifluoromethyl-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2,N-dimethyl-N-(4-trifluoromethyl-benzyl)-butyramide, N-(4-chloro-benzyl)-2-(3,4-dichloro-phenyl)-4-((S)-4-methanesulfonyl-3-methyl-piperazin-1-yl)-2,N-dimethyl-butyramide, 2-(3,4-dichloro-phenyl)-4-((S)-4-methanesulfonyl-3-methyl-piperazin-1-yl)-2,N-dimethyl-N-(3-trifluoromethyl-benzyl)-butyramide, (S)—N-(3,4-dichloro-benzyl)-2-(3,4-dichloro-phenyl)-4-((R)-4-methanesulfonyl-3-methyl-piperazin-1-yl)-2-methyl-butyramide, (R)—N-(3,4-dichloro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-(4-methanesulfonyl-piperazin-1-yl)-2,N-dimethyl-N-(3-trifluoromethyl-benzyl)-butyramide, (R or S)-2-(3,4-dichloro-phenyl)-N—((R)-2-hydroxy-1-phenyl-ethyl)-4-(4-methanesulfonyl-piperazin-1-yl)-2-methyl-butyramide and N—[(R)-1-(4-chloro-phenyl)-2-hydroxy-ethyl]-2-(3,4-dichloro-phenyl)-4-(4-methanesulfonyl-piperazin-1-yl)-2-methyl-butyramide.

Preferred are further compounds of formula IA, wherein n is 2. The following compounds relate to this group. 2-(3,4-dichloro-phenyl)-N-(3-fluoro-4-trifluoromethyl-benzyl)-4-(4-methanesulfonyl-[1,4]diazepan-1-yl)-2-methyl-butyramide, 2-(3,4-dichloro-phenyl)-4-(4-methanesulfonyl-[1,4]diazepan-1-yl)-2,N-dimethyl-N-(4-trifluoromethyl-benzyl)-butyramide, N-(4-chloro-benzyl)-2-(3,4-dichloro-phenyl)-4-(4-methanesulfonyl-[1,4]diazepan-1-yl)-2,N-dimethyl-butyramide, N-(4-chloro-3-fluoro-benzyl)-2-(3,4-dichloro-phenyl)-4-(4-methanesulfonyl-[1,4]diazepan-1-yl)-2-methyl-butyramide, 2-(3,4-dichloro-phenyl)-N-(3-fluoro-benzyl)-4-(4-methanesulfonyl-[1,4]diazepan-1-yl)-2,N-dimethyl-butyramide, 2-(3,4-dichloro-phenyl)-4-(4-methanesulfonyl-[1,4]diazepan-1-yl)-2,N-dimethyl-N-(3-trifluoromethyl-benzyl)-butyramide, N-(3-chloro-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-(3-fluoro-4-methoxy-benzyl)-4-(4-methanesulfonyl-[1,4]diazepan-1-yl)-2,N-dimethyl-butyramide, 2-(3,4-dichloro-phenyl)-N-(4-fluoro-3-trifluoromethyl-benzyl)-4-(4-methanesulfonyl-[1,4]diazepan-1-yl)-2,N-dimethyl-butyramide, 2-(3,4-dichloro-phenyl)-N-(4-difluoromethoxy-3-methoxy-benzyl)-4-(4-methanesulfonyl-[1,4]diazepan-1-yl)-2,N-dimethyl-butyramide, 2-(3,4-dichloro-phenyl)-4-(4-methanesulfonyl-[1,4]diazepan-1-yl)-2,N-dimethyl-N-(4-methyl-benzyl)-butyramide, N-(4-chloro-3-trifluoromethyl-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-(3-fluoro-4-trifluoromethyl-benzyl)-4-(4-methanesulfonyl-[1,4]diazepan-1-yl)-2,N-dimethyl-butyramide, N-(3,4-dichloro-benzyl)-2-(3,4-dichloro-phenyl)-4-(4-methanesulfonyl-[1,4]diazepan-1-yl)-2,N-dimethyl-butyramide, N-(3,4-dichloro-benzyl)-2-(3,4-dichloro-phenyl)-4-(4-methanesulfonyl-[1,4]diazepan-1-yl)-2-methyl-butyramide, 2-(3,4-dichloro-phenyl)-4-(4-methanesulfonyl-[1,4]diazepan-1-yl)-2-methyl-N-(4-trifluoromethyl-benzyl)-butyramide, N-(2-chloro-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-[1-(3,4-dichloro-phenyl)-ethyl]-4-(4-methanesulfonyl-[1,4]diazepan-1-yl)-2-methyl-butyramide, and 2-(3,4-dichloro-phenyl)-4-(4-methanesulfonyl-[1,4]diazepan-1-yl)-2,N-dimethyl-N-(4-pyridin-4-yl-benzyl)-butyramide.

The following groups of compounds of formula IB are preferred:

A compound of formula IB, wherein n is 1.

A compound of formula IB, wherein $R^2$ is lower alkyl.

A compound of formula IB, wherein $R^3$ is hydrogen or lower alkyl and $R^4$ is —$CHR^5$-A. Preferably A is an optionally substituted aryl, and particularly A is an optionally substituted phenyl, for example the following compounds N—[(R)-1-(4-chloro-phenyl)-2-hydroxy-ethyl]-2-(3,4-dichloro-phenyl)-4-(1,1-dioxo-hexahydro-1$\lambda^6$-thia-5,7a-diaza-inden-5-yl)-2-methyl-butyramide and 2-(3,4-dichloro-phenyl)-4-(1,1-dioxo-hexahydro-1$\lambda^6$-thia-5,7a-diaza-inden-5-yl)-N—[(R)-1-(4-fluoro-phenyl)-2-hydroxy-ethyl]-2-methyl-butyramide.

A further embodiment of the invention are compounds of formula

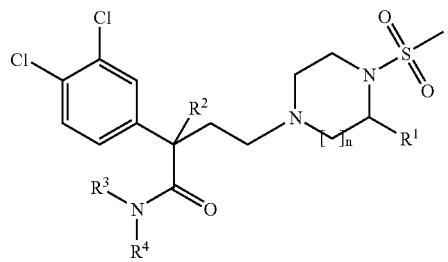

IA-1 wherein
R¹ is hydrogen or lower alkyl;
R² is hydrogen, fluoro or lower alkyl;
R³ is hydrogen or lower alkyl;
R⁴ is —CHR⁵-A
  R⁵ is hydrogen, lower alkyl, fluoro, CF₃, CH₂OH or cycloalkyl;
  A is aryl or heteroaryl, each of which is unsubstituted or substituted by (R⁶)ₒ;
  R⁶ is heteroaryl, lower alkyl, lower alkoxy, cyano, halogen, lower alkyl substituted by halogen, lower alkoxy substituted by halogen or NR⁷R⁸, wherein when o is more than one, each R⁶ is the same or different;
  o is 1, 2 or 3;
  R⁷ and R⁸ are each independently hydrogen or lower alkyl; and
n is 1 or 2;

or a pharmaceutically acceptable acid addition salt thereof.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by processes described below, which process comprises
cleaving off the ester group from a compound of formula

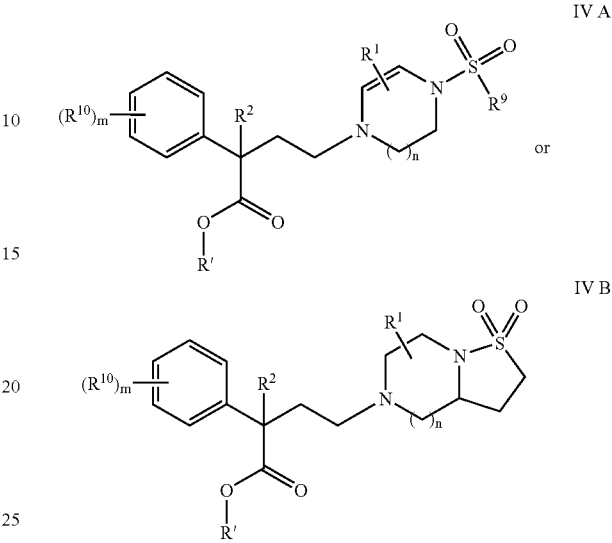

IV A or

IV B with aqueous bases, for example with NaOH or LiOH, and converting the acid of formula

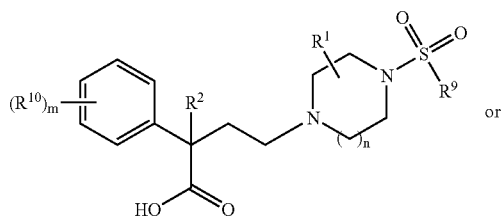

VIII A or

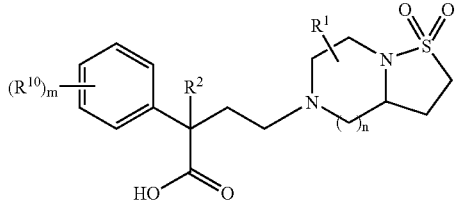

VIII B with a respective amine of formula

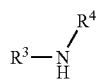

IX under coupling conditions to a compound of formula

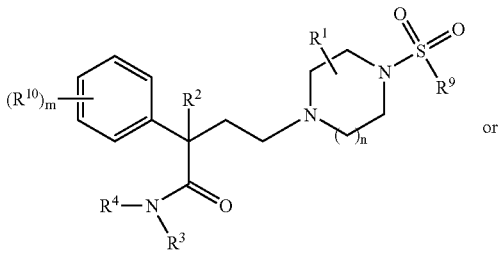

IA or

-continued

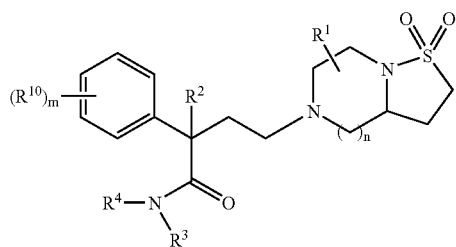
IB wherein the substituents and n have same meanings as described above, and R' is an O— protecting group, such as alkyl (e.g. methyl) or aryl (e.g. phenyl), and if desired, converting the compounds obtained into pharmaceutically acceptable acid addition salts.

The process is described in scheme 1 and scheme 2 in more detail.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 or 2, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

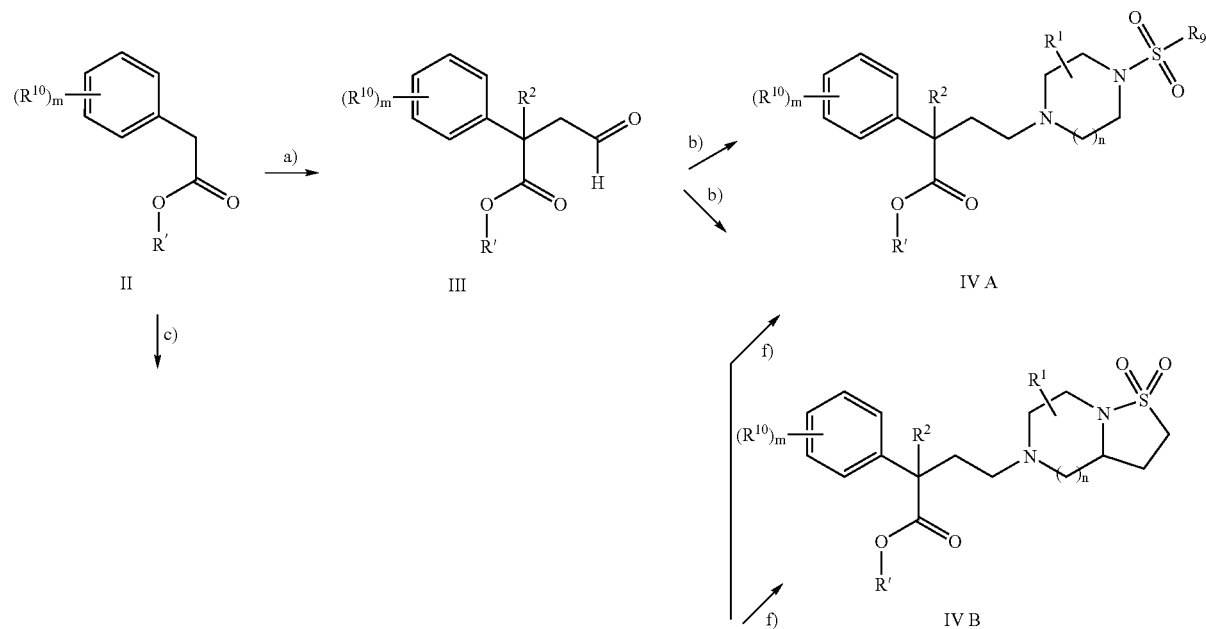

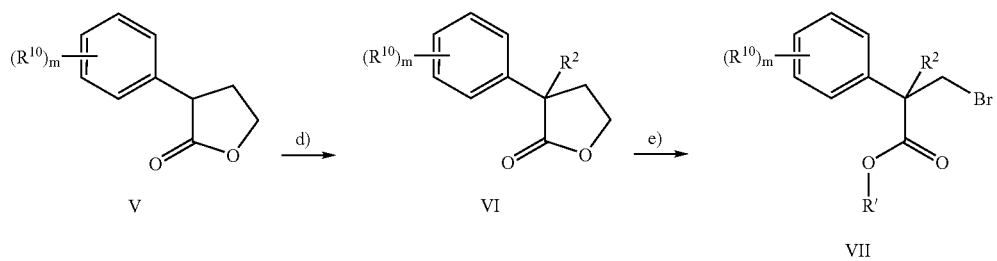

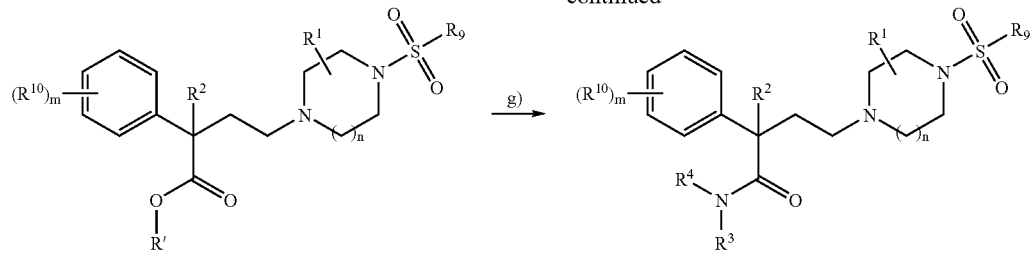

IV A → IA

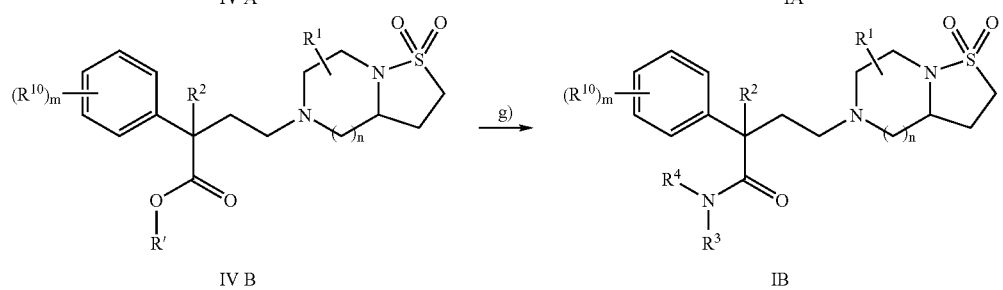

IV B → IB

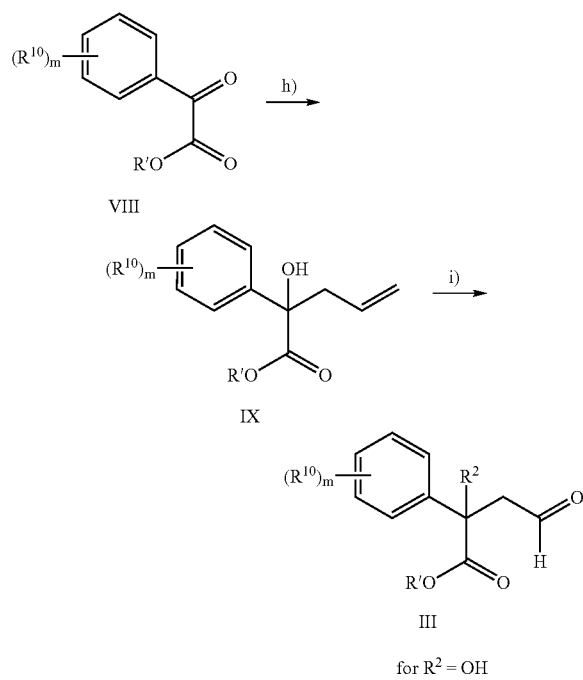

Scheme 2

VIII → IX → III for R² = OH

The substituents and n have same meanings as described above, and R' is an O— protecting group, such as alkyl (e.g. methyl) and aryl (e.g. phenyl)]

a) Phenylacetic acid ester derivatives II are commercially available or can be accessed by methods described in literature.

Reaction of ester derivatives II with protected bromo alkyl aldehydes (either commercially available or synthetically accessible by methods known in the art) under basic conditions lead to aldehyde derivatives III as described analogously in literature (for reaction conditions described in literature affecting such reactions see for example: *Comprehensive Organic Transformations: A Guide to Functional Group Preparations, 2nd Edition,* Richard C. Larock. John Wiley & Sons, New York, N.Y. 1999). However, it is convenient to react ester derivative II with the respective protected bromo alkyl aldehyde (commercially available or accessible by methods known) in the presence of a base and a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction can equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the aldehyde protected intermediate which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include tetrahydrofuran (THF) and the like.

There is no particular restriction on the nature of the acid used in this stage, and any acid commonly used in this type of reaction can equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield aldehyde derivatives III. Additionally, the protected aldehyde derivative can further be reacted to introduce $R^2$=alkyl. For reaction conditions described in literature affecting such reactions see for example: *Comprehensive Organic Transformations: A Guide to Functional Group Preparations, 2nd Edition,* Richard C. Larock. John Wiley & Sons, New York, N.Y. 1999). However, it is convenient to react the protected aldehyde intermediate with an electophile a in the presence of a base and a solvent.

There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction can equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the aldehyde protected intermediate which then can be subjected to acidic cleavage of the protecting group. The order of reaction of phenyl acetic acid derivatives consecutively with two suitable electrophiles can be chosen freely according to the reactivity of the reagents and compounds.

b) Reductive aminations are widely described in literature (for reaction conditions described in literature affecting such reactions see for example: *Comprehensive Organic Transformations: A Guide to Functional Group Preparations, 2nd Edition,* Richard C. Larock. John Wiley & Sons, New York, N.Y. 1999). However, we find it convenient to transform aldehyde derivative III with (homo) piperazine derivatives (*Journal of Medicinal Chemistry* (1983), 26(5), 657-61) under reductive conditions in the presence of a solvent to afford ester derivatives IV A or IV B. There is no particular restriction on the nature of the solvent to be employed, provided that it has no adverse effect on the reaction or the reagents involved and that it can dissolve the reagents, at least to some extent. Examples for suitable solvents include tetrahydrofuran (THF) and the like. There is no particular restriction on the nature of the reducing agent used in this stage, and any reducing agent commonly used in this type of reaction can equally be employed here. Examples of such reducing agents include sodium triacetoxyborohydride and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield ester derivative IV.

c) Reaction of ester derivatives II with hydroxy-protected alkyl halides (either commercially available or synthetically accessible by methods known in the art) under basic conditions lead upon cleavage of the hydroxyl protecting group to lactones V as described in literature (for reaction conditions described in literature affecting such reactions see for example: *Comprehensive Organic Transformations: A Guide to Functional Group Preparations, 2nd Edition,* Richard C. Larock. John Wiley & Sons, New York, N.Y. 1999). However, it is convenient to react ester derivative II with 2-(2-bromoethoxy)tetrahydro-2-H-pyrane (commercially available in the presence of a base and a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction can equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the hydroxy protected intermediate which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the acid used in this stage, and any acid commonly used in this type of reaction can equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield lactone derivatives V.

d) Lactone derivatives V can conveniently be transferred into the respective substituted lactone derivatives VI by reaction of lactone V with an electrophile in the presence of a base in the presence of a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction can equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield lactone derivatives VI.

e) Lactone derivative VI can conveniently transferred into the respective ester derivative VII by a two step reaction sequence. Any commonly used synthetic sequence is applicable however, we find it convenient to open the lactone derivative VII with HBr in the presence of an acid. Any commonly used acid which in combination with HBr affects such a reaction can be used. Examples of such acids include acetic acid and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the intermediately built acid derivative which is subjected to esterification conditions. Common procedures are described in literature, however, we find it convenient to transform the intermediately built acid into the respective ester derivative VII by reaction with $SOCl_2$ in methanol. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield ester derivative VII.

f) Transformation of ester derivative VII with (homo) piperazine derivatives (described in literature: see for instance *Journal of Medicinal Chemistry* (1983), 26(5), 657-61) to access (homo) piperazine derivatives IV A or IV B ca be affected by any commonly used procedure. However, we find it convenient to react ester derivative VII with (homo) piperazine derivatives in the presence of a solvent and a base. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction can equally be employed here. Examples of such bases include DIPEA, $NEt_3$ and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield (homo) piperazine derivatives IV A or IV B.

g) Transformation of (homo) piperazine derivatives IV A or IV B into the final amide derivatives can be done according to procedures described in literature. However, we find it convenient to employ a two step reaction sequence in which the ester functionality in IV A or IV B is cleaved under aqueous basic conditions and the liberated acid functionality converted with the respective amines under coupling conditions and to the (homo) piperazine derivatives IA or IB. There is no particular restriction on the nature of the aqueous base to be employed, provided that it has no adverse effect on the reaction or the reagents involved and that it can dissolve the reagents, at least to some extent. Examples for suitable aqueous bases include NaOH, LiOH and the like. Any commonly used co-solvent can be employed. Examples include THF and the like. The coupling of carboxylic acids with amines is widely described in literature and the procedures are known to those in the art (For reaction conditions described in literature affecting such reactions see for example: *Comprehensive Organic Transformations: A Guide to Functional Group Preparations, 2nd Edition*, Richard C. Larock. John Wiley & Sons, New York, N.Y. 1999). The intermediately built acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield (homo) piperazine derivatives I A or I B.

h) Pyruvate derivatives VIII are commercially available or can be synthesised by methods described in literature (For reaction conditions see for example: *Comprehensive Organic Transformations: A Guide to Functional Group Preparations, 2nd Edition*, Richard C. Larock. John Wiley & Sons, New York, N.Y. 1999). However we find it convenient to react pyruvate derivative VIII with allyl bromide and indium (0) in analogy to the procedure described in Synthetic Communications 2001, 3189-3196 to yield hydroxy-ester derivatives IX.

i) Transformation of the allyl-moiety in hydroxy-ester derivative IX to an aldehyde moiety can be achieved by various methods as described in literature. See for example *Comprehensive Organic Transformations: A Guide to Functional Group Preparations, 2nd Edition*, Richard C. Larock. John Wiley & Sons, New York, N.Y. 1999. However, we find it convenient to di-hydroxylate the allyl-moiety with $OsO_4$ and treat the intermediate product with $NaIO_4$ (for analogous reaction see for example: J. Am Chem Soc. 2006, 128,4590-4591) to furnish the allyl moiety in derivatives III ($R^2$=OH).

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. It has been found that the compounds of the present invention are antagonists of neurokinin 3 (NK-3) receptors. The compounds were investigated in accordance with the tests given hereinafter.

Experimental Procedure

The compounds were investigated in accordance with the tests given hereinafter.

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 μM phosphoramidon, 0.1% BSA binding buffer at pH 7.4 to a final assay concentration of 5 μg protein/well. For inhibition experiments, membranes were incubated with [$^3$H] SR142801 at a concentration equal to K$_D$ value of radioligand and 10 concentrations of the inhibitory compound (0.0003-10 μM) (in a total reaction volume of 500 μl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 μM SB222200 for both radioligands. The radioactivity on the filter was counted (5 min) on a Packard Top-count microplate scintillation counter with quenching correction after addition of 45 μl of microscint 40 (Canberra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

Some results of preferred compounds of the hNK-3 receptor affinity were shown in the following Table 1.

TABLE 1

| Example | Compound name | hNK$_3$ Ki [μM] |
|---|---|---|
| 1 | N-(4-Chloro-benzyl)-2-(3,4-dichloro-phenyl)-4-(4-methanesulfonyl-piperazin-1-yl)-N-methyl-butyramide | 0.1709 |
| 2 | 2-(3,4-Dichloro-phenyl)-4-(4-methanesulfonyl-piperazin-1-yl)-N-methyl-N-(4-pyridin-4-yl-benzyl)-butyramide | 0.3149 |
| 3 | N-(2-Chloro-benzyl)-2-(3,4-dichloro-phenyl)-4-(4-methanesulfonyl-piperazin-1-yl)-N-methyl-butyramide | 0.6546 |
| 4 | N-Benzyl-2-(3,4-dichloro-phenyl)-4-(4-methanesulfonyl-piperazin-1-yl)-N-methyl-butyramide | 0.3554 |
| 5 | 2-(3,4-Dichloro-phenyl)-4-(4-methanesulfonyl-piperazin-1-yl)-N-methyl-N-(4-trifluoromethyl-benzyl)-butyramide | 0.1355 |
| 6 | 2-(3,4-Dichloro-phenyl)-N-(3-fluoro-4-methoxy-benzyl)-4-(4-methanesulfonyl-piperazin-1-yl)-N-methyl-butyramide | 0.6899 |
| 7 | 2-(3,4-Dichloro-phenyl)-N-(3-fluoro-benzyl)-4-(4-methanesulfonyl-piperazin-1-yl)-N-methyl-butyramide | 0.3878 |
| 8 | 2-(3,4-Dichloro-phenyl)-4-(4-methanesulfonyl-piperazin-1-yl)-2-methyl-N-(3-trifluoromethyl-benzyl)-butyramide | 0.2884 |
| 9 | 2-(3,4-Dichloro-phenyl)-4-(4-methanesulfonyl-piperazin-1-yl)-2-methyl-N-(3-trifluoromethoxy-benzyl)-butyramide | 0.1896 |
| 10 | N-(3-Chloro-benzyl)-2-(3,4-dichloro-phenyl)-4-(4-methanesulfonyl-piperazin-1-yl)-2,N-dimethyl-butyramide | 0.1453 |
| 11 | 2-(3,4-Dichloro-phenyl)-N-(3-difluoromethoxy-benzyl)-4-(4-methanesulfonyl-piperazin-1-yl)-2-methyl-butyramide | 0.4168 |
| 12 | N-(4-Chloro-benzyl)-2-(3,4-dichloro-phenyl)-4-(4-methanesulfonyl-piperazin-1-yl)-2,N-dimethyl-butyramide | 0.0664 |
| 13 | 2-(3,4-Dichloro-phenyl)-N-(4-difluoromethoxy-benzyl)-4-(4-methanesulfonyl-piperazin-1-yl)-2-methyl-butyramide | 0.3259 |
| 14 | N-[1-(4-Chloro-phenyl)-ethyl]-2-(3,4-dichloro-phenyl)-4-(4-methanesulfonyl-piperazin-1-yl)-2-methyl-butyramide | 0.1707 |
| 15 | N-[Cyclopropyl-(4-methoxy-phenyl)-methyl]-2-(3,4-dichloro-phenyl)-4-(4-methanesulfonyl-piperazin-1-yl)-2-methyl-butyramide | 0.2338 |
| 16 | N-(2-Chloro-benzyl)-2-(3,4-dichloro-phenyl)-4-(4-methanesulfonyl-piperazin-1-yl)-2,N-dimethyl-butyramide | 0.1694 |
| 17 | 2-(3,4-Dichloro-phenyl)-4-(4-methanesulfonyl-piperazin-1-yl)-2-methyl-N-(4-trifluoromethoxy-benzyl)-butyramide | 0.1464 |
| 18 | N-(4-Cyano-benzyl)-2-(3,4-dichloro-phenyl)-4-(4-methanesulfonyl-piperazin-1-yl)-2-methyl-butyramide | 0.4337 |
| 19 | 2-(3,4-Dichloro-phenyl)-4-(4-methanesulfonyl-piperazin-1-yl)-2-methyl-N-(2-trifluoromethoxy-benzyl)-butyramide | 0.429 |
| 20 | 2-(3,4-Dichloro-phenyl)-N-(3-fluoro-4-trifluoromethyl-benzyl)-4-(4-methanesulfonyl-piperazin-1-yl)-2-methyl-butyramide | 0.0671 |
| 21 | N-(3,4-Dichloro-benzyl)-2-(3,4-dichloro-phenyl)-4-(4-methanesulfonyl-piperazin-1-yl)-2-methyl-butyramide | 0.0655 |
| 22 | 2-(3,4-Dichloro-phenyl)-4-(4-methanesulfonyl-piperazin-1-yl)-2,N-dimethyl-N-(4-methyl-benzyl)-butyramide | 0.0774 |
| 23 | 2-(3,4-Dichloro-phenyl)-4-(4-methanesulfonyl-piperazin-1-yl)-2,N-dimethyl-N-(4-pyridin-4-yl-benzyl)-butyramide | 0.2009 |

TABLE 1-continued

| Example | Compound name | hNK$_3$ Ki [μM] |
|---|---|---|
| 24 | 2-(3,4-Dichloro-phenyl)-N-(3-fluoro-benzyl)-4-(4-methanesulfonyl-piperazin-1-yl)-2,N-dimethyl-butyramide | 0.2238 |
| 25 | 2-(3,4-Dichloro-phenyl)-N-(3-fluoro-4-methoxy-benzyl)-4-(4-methanesulfonyl-piperazin-1-yl)-2,N-dimethyl-butyramide | 0.1335 |
| 26 | 2-(3,4-Dichloro-phenyl)-N-(4-difluoromethoxy-3-methoxy-benzyl)-4-(4-methanesulfonyl-piperazin-1-yl)-2,N-dimethyl-butyramide | 0.2748 |
| 27 | 2-(3,4-Dichloro-phenyl)-4-(4-methanesulfonyl-piperazin-1-yl)-2-methyl-N-(4-trifluoromethyl-benzyl)-butyramide | 0.082 |
| 28 | 2-(3,4-Dichloro-phenyl)-4-(4-methanesulfonyl-piperazin-1-yl)-2,N-dimethyl-N-(4-trifluoromethyl-benzyl)-butyramide | 0.045 |
| 29 | N-(4-Chloro-benzyl)-2-(3,4-dichloro-phenyl)-4-(4-methanesulfonyl-piperazin-1-yl)-2-methyl-butyramide | 0.0984 |
| 30 | N-(4-Chloro-3-fluoro-benzyl)-2-(3,4-dichloro-phenyl)-4-(4-methanesulfonyl-piperazin-1-yl)-2-methyl-butyramide | 0.1334 |
| 31 | 2-(3,4-Dichloro-phenyl)-N-(3-fluoro-4-methoxy-benzyl)-4-((R)-4-methanesulfonyl-3-methyl-piperazin-1-yl)-2,N-dimethyl-butyramide | 0.1087 |
| 32 | N-[Cyclopropyl-(4-methoxy-phenyl)-methyl]-2-(3,4-dichloro-phenyl)-4-((R)-4-methanesulfonyl-3-methyl-piperazin-1-yl)-2-methyl-butyramide | 0.0168 |
| 33 | 2-(3,4-Dichloro-phenyl)-N-(4-fluoro-3-trifluoromethyl-benzyl)-4-((R)-4-methanesulfonyl-3-methyl-piperazin-1-yl)-2,N-dimethyl-butyramide | 0.0158 |
| 34 | N-(3,5-Bis-trifluoromethyl-benzyl)-2-(3,4-dichloro-phenyl)-4-((R)-4-methanesulfonyl-3-methyl-piperazin-1-yl)-2-methyl-butyramide | 0.0481 |
| 35 | 2-(3,4-Dichloro-phenyl)-N-(4-difluoromethoxy-3-methoxy-benzyl)-4-((R)-4-methanesulfonyl-3-methyl-piperazin-1-yl)-2,N-dimethyl-butyramide | 0.2159 |
| 36 | 2-(3,4-Dichloro-phenyl)-4-((R)-4-methanesulfonyl-3-methyl-piperazin-1-yl)-2,N-dimethyl-N-(4-methyl-benzyl)-butyramide | 0.0508 |
| 37 | 2-(3,4-Dichloro-phenyl)-N-(4-dimethylamino-benzyl)-4-((R)-4-methanesulfonyl-3-methyl-piperazin-1-yl)-2-methyl-butyramide | 0.4851 |
| 38 | 2-(3,4-Dichloro-phenyl)-4-((R)-4-methanesulfonyl-3-methyl-piperazin-1-yl)-2-methyl-N-quinoxalin-6-ylmethyl-butyramide | 0.5452 |
| 39 | N-(4-Chloro-3-trifluoromethyl-benzyl)-2-(3,4-dichloro-phenyl)-4-((R)-4-methanesulfonyl-3-methyl-piperazin-1-yl)-2,N-dimethyl-butyramide | 0.0126 |
| 40 | 2-(3,4-Dichloro-phenyl)-N-(3-fluoro-4-trifluoromethyl-benzyl)-4-((R)-4-methanesulfonyl-3-methyl-piperazin-1-yl)-2,N-dimethyl-butyramide | 0.0167 |
| 41 | N-(3,4-Dichloro-benzyl)-2-(3,4-dichloro-phenyl)-4-((R)-4-methanesulfonyl-3-methyl-piperazin-1-yl)-2,N-dimethyl-butyramide | 0.0133 |
| 42 | N-(3,4-Dichloro-benzyl)-2-(3,4-dichloro-phenyl)-4-((R)-4-methanesulfonyl-3-methyl-piperazin-1-yl)-2-methyl-butyramide | 0.0057 |
| 43 | 2-(3,4-Dichloro-phenyl)-N-(3-difluoromethoxy-benzyl)-4-((R)-4-methanesulfonyl-3-methyl-piperazin-1-yl)-2-methyl-butyramide | 0.0999 |
| 44 | 2-(3,4-Dichloro-phenyl)-N-(5-fluoro-2-trifluoromethyl-benzyl)-4-((R)-4-methanesulfonyl-3-methyl-piperazin-1-yl)-2-methyl-butyramide | 0.2123 |
| 45 | 2-(3,4-Dichloro-phenyl)-4-((R)-4-methanesulfonyl-3-methyl-piperazin-1-yl)-2-methyl-N-(4-trifluoromethyl-benzyl)-butyramide | 0.0333 |
| 46 | 2-(3,4-Dichloro-phenyl)-N-(2-fluoro-5-trifluoromethyl-benzyl)-4-((R)-4-methanesulfonyl-3-methyl-piperazin-1-yl)-2-methyl-butyramide | 0.0995 |
| 47 | N-[1-(4-Chloro-phenyl)-ethyl]-2-(3,4-dichloro-phenyl)-4-((R)-4-methanesulfonyl-3-methyl-piperazin-1-yl)-2-methyl-butyramide | 0.0159 |
| 48 | 2-(3,4-Dichloro-phenyl)-4-((R)-4-methanesulfonyl-3-methyl-piperazin-1-yl)-N-(3-methoxy-benzyl)-2,N-dimethyl-butyramide | 0.2629 |
| 49 | N-(2-Chloro-benzyl)-2-(3,4-dichloro-phenyl)-4-((R)-4-methanesulfonyl-3-methyl-piperazin-1-yl)-2,N-dimethyl-butyramide | 0.088 |
| 50 | 2-(3,4-Dichloro-phenyl)-N-[1-(3,4-dichloro-phenyl)-ethyl]-4-((R)-4-methanesulfonyl-3-methyl-piperazin-1-yl)-2-methyl-butyramide | 0.0258 |

TABLE 1-continued

| Example | Compound name | hNK$_3$ Ki [µM] |
|---|---|---|
| 51 | 2-(3,4-Dichloro-phenyl)-4-((R)-4-methanesulfonyl-3-methyl-piperazin-1-yl)-2-methyl-N-(3-trifluoromethoxy-benzyl)-butyramide | 0.0146 |
| 52 | N-(4-Chloro-3-fluoro-benzyl)-2-(3,4-dichloro-phenyl)-4-((R)-4-methanesulfonyl-3-methyl-piperazin-1-yl)-2-methyl-butyramide | 0.0464 |
| 53 | 2-(3,4-Dichloro-phenyl)-4-((R)-4-methanesulfonyl-3-methyl-piperazin-1-yl)-2-methyl-N-(4-trifluoromethoxy-benzyl)-butyramide | 0.0228 |
| 54 | N-(4-Chloro-3-trifluoromethyl-benzyl)-2-(3,4-dichloro-phenyl)-4-((R)-4-methanesulfonyl-3-methyl-piperazin-1-yl)-2-methyl-butyramide | 0.0175 |
| 55 | 2-(3,4-Dichloro-phenyl)-4-((R)-4-methanesulfonyl-3-methyl-piperazin-1-yl)-2,N-dimethyl-N-(4-trifluoromethyl-benzyl)-butyramide | 0.0169 |
| 56 | N-(4-Chloro-benzyl)-2-(3,4-dichloro-phenyl)-4-((R)-4-methanesulfonyl-3-methyl-piperazin-1-yl)-2,N-dimethyl-butyramide | 0.0265 |
| 57 | N-(4-Cyano-benzyl)-2-(3,4-dichloro-phenyl)-4-((R)-4-methanesulfonyl-3-methyl-piperazin-1-yl)-2-methyl-butyramide | 0.1611 |
| 58 | 2-(3,4-Dichloro-phenyl)-4-((R)-4-methanesulfonyl-3-methyl-piperazin-1-yl)-2,N-dimethyl-N-(3-trifluoromethyl-benzyl)-butyramide | 0.0562 |
| 59 | N-(3-Chloro-benzyl)-2-(3,4-dichloro-phenyl)-4-((R)-4-methanesulfonyl-3-methyl-piperazin-1-yl)-2,N-dimethyl-butyramide | 0.1032 |
| 60 | 2-(3,4-Dichloro-phenyl)-N-(3-fluoro-benzyl)-4-((R)-4-methanesulfonyl-3-methyl-piperazin-1-yl)-2,N-dimethyl-butyramide | 0.1305 |
| 61 | 2-(3,4-Dichloro-phenyl)-4-((S)-4-methanesulfonyl-3-methyl-piperazin-1-yl)-2,N-dimethyl-N-(4-pyridin-4-yl-benzyl)-butyramide | 0.2468 |
| 62 | 2-(3,4-Dichloro-phenyl)-N-(3-fluoro-4-methoxy-benzyl)-4-((S)-4-methanesulfonyl-3-methyl-piperazin-1-yl)-2,N-dimethyl-butyramide | 0.2156 |
| 63 | N-[Cyclopropyl-(4-methoxy-phenyl)-methyl]-2-(3,4-dichloro-phenyl)-4-((S)-4-methanesulfonyl-3-methyl-piperazin-1-yl)-2-methyl-butyramide | 0.0657 |
| 64 | 2-(3,4-Dichloro-phenyl)-N-(4-fluoro-3-trifluoromethyl-benzyl)-4-((S)-4-methanesulfonyl-3-methyl-piperazin-1-yl)-2,N-dimethyl-butyramide | 0.0168 |
| 65 | N-(3,5-Bis-trifluoromethyl-benzyl)-2-(3,4-dichloro-phenyl)-4-((S)-4-methanesulfonyl-3-methyl-piperazin-1-yl)-2-methyl-butyramide | 0.0846 |
| 66 | 2-(3,4-Dichloro-phenyl)-N-(4-difluoromethoxy-3-methoxy-benzyl)-4-((S)-4-methanesulfonyl-3-methyl-piperazin-1-yl)-2,N-dimethyl-butyramide | 0.2767 |
| 67 | 2-(3,4-Dichloro-phenyl)-4-((S)-4-methanesulfonyl-3-methyl-piperazin-1-yl)-2,N-dimethyl-N-(4-methyl-benzyl)-butyramide | 0.0992 |
| 68 | 2-(3,4-Dichloro-phenyl)-N-(4-dimethylamino-benzyl)-4-((S)-4-methanesulfonyl-3-methyl-piperazin-1-yl)-2-methyl-butyramide | 0.7341 |
| 69 | N-(4-Chloro-3-trifluoromethyl-benzyl)-2-(3,4-dichloro-phenyl)-4-((S)-4-methanesulfonyl-3-methyl-piperazin-1-yl)-2,N-dimethyl-butyramide | 0.0114 |
| 70 | 2-(3,4-Dichloro-phenyl)-N-(3-fluoro-4-trifluoromethyl-benzyl)-4-((S)-4-methanesulfonyl-3-methyl-piperazin-1-yl)-2,N-dimethyl-butyramide | 0.0192 |
| 71 | N-(3,4-Dichloro-benzyl)-2-(3,4-dichloro-phenyl)-4-((S)-4-methanesulfonyl-3-methyl-piperazin-1-yl)-2,N-dimethyl-butyramide | 0.0125 |
| 72 | N-(3,4-Dichloro-benzyl)-2-(3,4-dichloro-phenyl)-4-((S)-4-methanesulfonyl-3-methyl-piperazin-1-yl)-2-methyl-butyramide | 0.0429 |
| 73 | 2-(3,4-Dichloro-phenyl)-N-(3-difluoromethoxy-benzyl)-4-((S)-4-methanesulfonyl-3-methyl-piperazin-1-yl)-2-methyl-butyramide | 0.2998 |
| 74 | 2-(3,4-Dichloro-phenyl)-N-(5-fluoro-2-trifluoromethyl-benzyl)-4-((S)-4-methanesulfonyl-3-methyl-piperazin-1-yl)-2-methyl-butyramide | 0.4962 |
| 75 | 2-(3,4-Dichloro-phenyl)-4-((S)-4-methanesulfonyl-3-methyl-piperazin-1-yl)-2-methyl-N-(4-trifluoromethyl-benzyl)-butyramide | 0.0681 |

TABLE 1-continued

| Example | Compound name | hNK$_3$ Ki [µM] |
|---|---|---|
| 76 | 2-(3,4-Dichloro-phenyl)-N-(2-fluoro-5-trifluoromethyl-benzyl)-4-((S)-4-methanesulfonyl-3-methyl-piperazin-1-yl)-2-methyl-butyramide | 0.311 |
| 77 | N-[1-(4-Chloro-phenyl)-ethyl]-2-(3,4-dichloro-phenyl)-4-((S)-4-methanesulfonyl-3-methyl-piperazin-1-yl)-2-methyl-butyramide | 0.0674 |
| 78 | 2-(3,4-Dichloro-phenyl)-4-((S)-4-methanesulfonyl-3-methyl-piperazin-1-yl)-N-(3-methoxy-benzyl)-2,N-dimethyl-butyramide | 0.6112 |
| 79 | N-(2-Chloro-benzyl)-2-(3,4-dichloro-phenyl)-4-((S)-4-methanesulfonyl-3-methyl-piperazin-1-yl)-2,N-dimethyl-butyramide | 0.1677 |
| 80 | 2-(3,4-Dichloro-phenyl)-N-[1-(3,4-dichloro-phenyl)-ethyl]-4-((S)-4-methanesulfonyl-3-methyl-piperazin-1-yl)-2-methyl-butyramide | 0.0162 |
| 81 | 2-(3,4-Dichloro-phenyl)-4-((S)-4-methanesulfonyl-3-methyl-piperazin-1-yl)-2-methyl-N-(3-trifluoromethoxy-benzyl)-butyramide | 0.1259 |
| 82 | N-(4-Chloro-3-fluoro-benzyl)-2-(3,4-dichloro-phenyl)-4-((S)-4-methanesulfonyl-3-methyl-piperazin-1-yl)-2-methyl-butyramide | 0.0942 |
| 83 | 2-(3,4-Dichloro-phenyl)-4-((S)-4-methanesulfonyl-3-methyl-piperazin-1-yl)-2-methyl-N-(4-trifluoromethoxy-benzyl)-butyramide | 0.0571 |
| 84 | N-(4-Chloro-3-trifluoromethyl-benzyl)-2-(3,4-dichloro-phenyl)-4-((S)-4-methanesulfonyl-3-methyl-piperazin-1-yl)-2-methyl-butyramide | 0.0452 |
| 85 | 2-(3,4-Dichloro-phenyl)-4-((S)-4-methanesulfonyl-3-methyl-piperazin-1-yl)-2,N-dimethyl-N-(4-trifluoromethyl-benzyl)-butyramide | 0.0277 |
| 86 | N-(4-Chloro-benzyl)-2-(3,4-dichloro-phenyl)-4-((S)-4-methanesulfonyl-3-methyl-piperazin-1-yl)-2,N-dimethyl-butyramide | 0.0663 |
| 87 | 2-(3,4-Dichloro-phenyl)-4-((S)-4-methanesulfonyl-3-methyl-piperazin-1-yl)-2,N-dimethyl-N-(3-trifluoromethyl-benzyl)-butyramide | 0.052 |
| 88 | N-(3-Chloro-benzyl)-2-(3,4-dichloro-phenyl)-4-((S)-4-methanesulfonyl-3-methyl-piperazin-1-yl)-2,N-dimethyl-butyramide | 0.1069 |
| 89 | 2-(3,4-Dichloro-phenyl)-N-(3-fluoro-benzyl)-4-((S)-4-methanesulfonyl-3-methyl-piperazin-1-yl)-2,N-dimethyl-butyramide | 0.2656 |
| 90 | 2-(3,4-Dichloro-phenyl)-4-((S)-4-methanesulfonyl-3-methyl-piperazin-1-yl)-2,N-dimethyl-N-(6-trifluoromethyl-pyridin-3-ylmethyl)-butyramide | 0.5251 |
| 91 | 2-(3,4-Dichloro-phenyl)-4-((S)-4-methanesulfonyl-3-methyl-piperazin-1-yl)-2-methyl-N-(6-trifluoromethyl-pyridin-3-ylmethyl)-butyramide | 0.9063 |
| 92 | 2-(3,4-Dichloro-phenyl)-4-((R)-4-methanesulfonyl-3-methyl-piperazin-1-yl)-2-methyl-N-(6-trifluoromethyl-pyridin-3-ylmethyl)-butyramide | 0.5821 |
| 93 | (S or R)—N-(3,4-Dichloro-benzyl)-2-(3,4-dichloro-phenyl)-4-((R)-4-methanesulfonyl-3-methyl-piperazin-1-yl)-2-methyl-butyramide | 0.0192 |
| 94 | (R or S)—N-(3,4-Dichloro-benzyl)-2-(3,4-dichloro-phenyl)-4-((R)-4-methanesulfonyl-3-methyl-piperazin-1-yl)-2-methyl-butyramide | 0.112 |
| 95 | 2-(3,4-Dichloro-phenyl)-N-(3-fluoro-4-trifluoromethyl-benzyl)-4-(4-methanesulfonyl-[1,4]diazepan-1-yl)-2-methyl-butyramide | 0.0643 |
| 96 | 2-(3,4-Dichloro-phenyl)-4-(4-methanesulfonyl-[1,4]diazepan-1-yl)-2,N-dimethyl-N-(4-trifluoromethyl-benzyl)-butyramide | 0.0245 |
| 97 | N-(4-Chloro-benzyl)-2-(3,4-dichloro-phenyl)-4-(4-methanesulfonyl-[1,4]diazepan-1-yl)-2,N-dimethyl-butyramide | 0.0299 |
| 98 | N-(4-Chloro-3-fluoro-benzyl)-2-(3,4-dichloro-phenyl)-4-(4-methanesulfonyl-[1,4]diazepan-1-yl)-2-methyl-butyramide | 0.066 |
| 99 | 2-(3,4-Dichloro-phenyl)-4-(4-methanesulfonyl-[1,4]diazepan-1-yl)-2-methyl-N-(4-trifluoromethoxy-benzyl)-butyramide | 0.1277 |
| 100 | 2-(3,4-Dichloro-phenyl)-N-(3-fluoro-benzyl)-4-(4-methanesulfonyl-[1,4]diazepan-1-yl)-2,N-dimethyl-butyramide | 0.0965 |
| 101 | 2-(3,4-Dichloro-phenyl)-4-(4-methanesulfonyl-[1,4]diazepam-1-yl)-2,N-dimethyl-N-(3-trifluoromethyl-benzyl)-butyramide | 0.0184 |
| 102 | 2-(3,4-Dichloro-phenyl)-4-(4-methanesulfonyl-[1,4]diazepan-1-yl)-2-methyl-N-(3-trifluoromethoxy-benzyl)-butyramide | 0.1229 |

TABLE 1-continued

| Example | Compound name | hNK$_3$ Ki [μM] |
|---|---|---|
| 103 | N-(3-Chloro-benzyl)-2-(3,4-dichloro-phenyl)-4-(4-methanesulfonyl-[1,4]diazepan-1-yl)-2,N-dimethyl-butyramide | 0.0418 |
| 104 | 2-(3,4-Dichloro-phenyl)-N-(3-fluoro-4-methoxy-benzyl)-4-(4-methanesulfonyl-[1,4]diazepan-1-yl)-2,N-dimethyl-butyramide | 0.0602 |
| 105 | N-[Cyclopropyl-(4-methoxy-phenyl)-methyl]-2-(3,4-dichloro-phenyl)-4-(4-methanesulfonyl-[1,4]diazepan-1-yl)-2-methyl-butyramide | 0.1345 |
| 106 | 2-(3,4-Dichloro-phenyl)-N-(4-fluoro-3-trifluoromethyl-benzyl)-4-(4-methanesulfonyl-[1,4]diazepan-1-yl)-2,N-dimethyl-butyramide | 0.0092 |
| 107 | N-(3,5-Bis-trifluoromethyl-benzyl)-2-(3,4-dichloro-phenyl)-4-(4-methanesulfonyl-[1,4]diazepan-1-yl)-2-methyl-butyramide | 0.2094 |
| 108 | 2-(3,4-Dichloro-phenyl)-N-(4-difluoromethoxy-3-methoxy-benzyl)-4-(4-methanesulfonyl-[1,4]diazepan-1-yl)-2,N-dimethyl-butyramide | 0.0895 |
| 109 | 2-(3,4-Dichloro-phenyl)-4-(4-methanesulfonyl-[1,4]diazepan-1-yl)-2,N-dimethyl-N-(4-methyl-benzyl)-butyramide | 0.0335 |
| 110 | 2-(3,4-Dichloro-phenyl)-N-(4-dimethylamino-benzyl)-4-(4-methanesulfonyl-[1,4]diazepan-1-yl)-2-methyl-butyramide | 0.2908 |
| 111 | N-(4-Chloro-3-trifluoromethyl-benzyl)-2-(3,4-dichloro-phenyl)-4-(4-methanesulfonyl-[1,4]diazepan-1-yl)-2,N-dimethyl-butyramide | 0.0067 |
| 112 | 2-(3,4-Dichloro-phenyl)-N-(3-fluoro-4-trifluoromethyl-benzyl)-4-(4-methanesulfonyl-[1,4]diazepan-1-yl)-2,N-dimethyl-butyramide | 0.0162 |
| 113 | N-(3,4-Dichloro-benzyl)-2-(3,4-dichloro-phenyl)-4-(4-methanesulfonyl-[1,4]diazepan-1-yl)-2,N-dimethyl-butyramide | 0.0101 |
| 114 | N-(3,4-Dichloro-benzyl)-2-(3,4-dichloro-phenyl)-4-(4-methanesulfonyl-[1,4]diazepan-1-yl)-2-methyl-butyramide | 0.0399 |
| 115 | 2-(3,4-Dichloro-phenyl)-N-(3-difluoromethoxy-benzyl)-4-(4-methanesulfonyl-[1,4]diazepan-1-yl)-2-methyl-butyramide | 0.1832 |
| 116 | 2-(3,4-Dichloro-phenyl)-N-(5-fluoro-2-trifluoromethyl-benzyl)-4-(4-methanesulfonyl-[1,4]diazepan-1-yl)-2-methyl-butyramide | 0.5751 |
| 117 | 2-(3,4-Dichloro-phenyl)-4-(4-methanesulfonyl-[1,4]diazepan-1-yl)-2-methyl-N-(4-trifluoromethyl-benzyl)-butyramide | 0.0496 |
| 118 | 2-(3,4-Dichloro-phenyl)-N-(2-fluoro-5-trifluoromethyl-benzyl)-4-(4-methanesulfonyl-[1,4]diazepan-1-yl)-2-methyl-butyramide | 0.1358 |
| 119 | N-[1-(4-Chloro-phenyl)-ethyl]-2-(3,4-dichloro-phenyl)-4-(4-methanesulfonyl-[1,4]diazepan-1-yl)-2-methyl-butyramide | 0.1212 |
| 120 | 2-(3,4-Dichloro-phenyl)-4-(4-methanesulfonyl-[1,4]diazepan-1-yl)-N-(3-methoxy-benzyl)-2,N-dimethyl-butyramide | 0.1079 |
| 121 | N-(2-Chloro-benzyl)-2-(3,4-dichloro-phenyl)-4-(4-methanesulfonyl-[1,4]diazepan-1-yl)-2,N-dimethyl-butyramide | 0.0312 |
| 122 | 2-(3,4-Dichloro-phenyl)-N-[1-(3,4-dichloro-phenyl)-ethyl]-4-(4-methanesulfonyl-[1,4]diazepan-1-yl)-2-methyl-butyramide | 0.0434 |
| 123 | 2-(3,4-Dichloro-phenyl)-4-(4-methanesulfonyl-[1,4]diazepan-1-yl)-2,N-dimethyl-N-(4-pyridin-4-yl-benzyl)-butyramide | 0.0934 |
| 124 | N-(4-Cyano-benzyl)-2-(3,4-dichloro-phenyl)-4-(4-methanesulfonyl-[1,4]diazepan-1-yl)-2-methyl-butyramide | 0.1074 |
| 125 | 2-(3,4-Dichloro-phenyl)-4-(4-methanesulfonyl-[1,4]diazepan-1-yl)-2,N-dimethyl-N-(6-trifluoromethyl-pyridin-3-ylmethyl)-butyramide | 0.2751 |
| 126 | 2-(3,4-Dichloro-phenyl)-4-(4-methanesulfonyl-[1,4]diazepan-1-yl)-2-methyl-N-(6-trifluoromethyl-pyridin-3-ylmethyl)-butyramide | 0.9486 |
| 127 | 2-(3,4-Dichloro-phenyl)-4-(4-methanesulfonyl-piperazin-1-yl)-2,N-dimethyl-N-(3-trifluoromethyl-benzyl)-butyramide | 0.0784 |
| 128 | (R or S)-2-(3,4-Dichloro-phenyl)-N-((R)-2-hydroxy-1-phenyl-ethyl)-4-(4-methanesulfonyl-piperazin-1-yl)-2-methyl-butyramide | 0.0406 |
| 129 | (S or R)-2-(3,4-Dichloro-phenyl)-N-((R)-2-hydroxy-1-phenyl-ethyl)-4-(4-methanesulfonyl-piperazin-1-yl)-2-methyl-butyramide | 0.3338 |
| 130 | N-[(R)-1-(4-Chloro-phenyl)-2-hydroxy-ethyl]-2-(3,4-dichloro-phenyl)-4-(4-methanesulfonyl-piperazin-1-yl)-2-methyl-butyramide | 0.0399 |
| 131 | N-[(S)-1-(4-Chloro-phenyl)-2-hydroxy-ethyl]-2-(3,4-dichloro-phenyl)-4-(4-methanesulfonyl-piperazin-1-yl)-2-methyl-butyramide | 0.1863 |

TABLE 1-continued

| Example | Compound name | hNK$_3$ Ki [μM] |
|---|---|---|
| 132 | 2-(3,4-Dichloro-phenyl)-N-[(R)-1-(4-fluoro-phenyl)-2-hydroxy-ethyl]-4-(4-methanesulfonyl-piperazin-1-yl)-2-methyl-butyramide | 0.1463 |
| 133 | 2-(3,4-Dichloro-phenyl)-N-[(S)-1-(4-fluoro-phenyl)-2-hydroxy-ethyl]-4-(4-methanesulfonyl-piperazin-1-yl)-2-methyl-butyramide | 0.3972 |
| 134 | 2-(3,4-Dichloro-phenyl)-N-[1-(4-fluoro-phenyl)-ethyl]-4-(4-methanesulfonyl-piperazin-1-yl)-2-methyl-butyramide | 0.2287 |
| 135 | 2-(3,4-Dichloro-phenyl)-4-(4-methanesulfonyl-piperazin-1-yl)-2-methyl-N-[2,2,2-trifluoro-1-(4-fluoro-phenyl)-ethyl]-butyramide | 0.1961 |
| 136 | N-[(R)-1-(4-Chloro-phenyl)-2-hydroxy-ethyl]-2-(3,4-dichloro-phenyl)-4-(1,1-dioxo-hexahydro-1$\lambda^6$-thia-5,7a-diaza-inden-5-yl)-2-methyl-butyramide | 0.0154 |
| 137 | 2-(3,4-Dichloro-phenyl)-4-(1,1-dioxo-hexahydro-1$\lambda^6$-thia-5,7a-diaza-inden-5-yl)-N-[(R)-1-(4-fluoro-phenyl)-2-hydroxy-ethyl]-2-methyl-butyramide | 0.0305 |

In addition, the present compounds showed high selective affinity to the hNK-3 receptor compared with the hNK-1 and hNK-2 receptors.

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatin capsules.

EXAMPLE C

Suppositories of the following composition can be manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool, the suppositories then can be removed from the moulds and packed individually in wax paper or metal foil.

The following Examples illustrate the present invention without limiting it. All temperatures are given in degrees Celsius.

Abbreviations
DCM=dichloromethane;
DIPEA=N,N-diisopropylethylamine;
DMA=N,N-dimethylacetamido;
DMF=N,N-dimethylformamide;
HPLC=high-performance liquid chromatography;
MS=mass spectroscopy;
TBTU=O-benzotriazol-1-yl-N,N,N',N'-tetramethyluronium tetrafluoroborate;
THF=tetrahydrofurane.

Intermediate 1

2-(3,4-Dichloro-phenyl)-4-(4-methanesulfonyl-piperazin-1-yl)-butyric acid

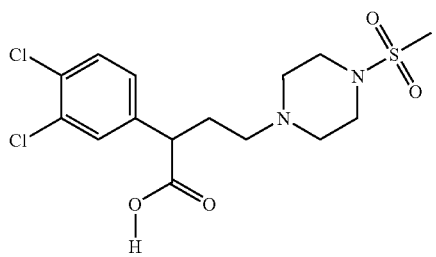

a) step 1: 2-(3,4-Dichloro-phenyl)-4-oxo-butyric acid methyl ester

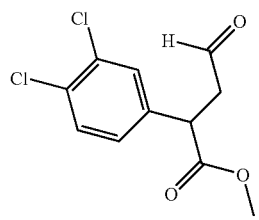

A mixture of 25 g (114 mmol) (3,4-dichloro-phenyl)-acetic acid methyl ester (commercially available), 5.7 g (131 mmol) NaH (55%) and 23.1 g (137 mmol) bromoacetaldehyde dimethylacetal in 80 mL DMF was stirred at room temperature for 3 h. The mixture was poured onto ice/water and extracted with ethyl acetate. The combined organic phases were washed with NaCl aq., dried with $Na_2SO_4$ and evaporated to dryness. The residue was dissolved in 250 mL THF and treated with 300 mL 1N HCl at room temperature for 20 h. Water was added and the mixture was extracted with ethyl acetate. The combined organic phases were washed with NaCl aq., dried with $Na_2SO_4$, evaporated to dryness and subjected to column chromatography on silica eluting with a gradient formed from heptane and ethyl acetate. The product containing fractions were evaporated to yield 9.7 g (32%) of the title compound as light yellow oil.

MS(m/e): 260.1/262.2 ($MH^+$).

b) step 2: 2-(3,4-Dichloro-phenyl)-4-(4-methanesulfonyl-piperazin-1-yl)-butyric acid methyl ester

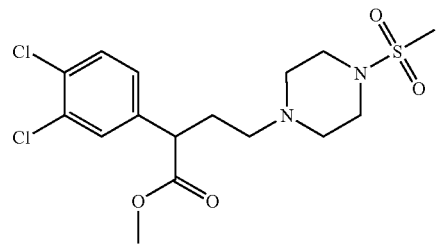

A mixture of 1.07 g (4.1 mmol) 2-(3,4-dichloro-phenyl)-4-oxo-butyric acid methyl ester, 0.74 g (4.5 mmol) 1-methanesolfonyl-piperazine, 1.3 g (6.1 mmol) sodium triacteoxyborohydride and 0.37 g (6.1 mmol) acetic acid in 40 mL THF was stirred at room temperature for 17 h. Water and $Na_2CO_3$ aq. (10%) was added and the mixture was extracted with ethyl acetate. The combined organic fractions were washed with NaCl sat. aq. dried with $MgSO_4$, filtered and evaporated to dryness. The residue was purified by flash column chromatography on silica eluting with a gradient formed from DCM, methanol and $NH_3$ aq. The product containing fractions were evaporated to yield 1.42 g (85%) of the title compound as colorless waxy solid. MS(m/e): 409.3 ($MH^+$).

c) step 3: 2-(3,4-Dichloro-phenyl)-4-(4-methanesulfonyl-piperazin-1-yl)-butyric acid A mixture of 1.42 g (3.4 mmol) 2-(3,4-dichloro-phenyl)-4-(4-methanesulfonyl-piperazin-1-yl)-butyric acid methyl ester and 0.182 g (4.3 mmol) $LiOH.H_2O$ in 30 mL water and 30 mL THF was heated to reflux for 1 h. The mixture was treated with 4N HCl aq. and evaporated to dryness. The residue was used without further purification in the subsequent step. MS(m/e): 395.0 ($MH^+$).

Intermediate 2

2-(3,4-Dichloro-phenyl)-4-(4-methanesulfonyl-piperazin-1-yl)-2-methyl-butyric acid

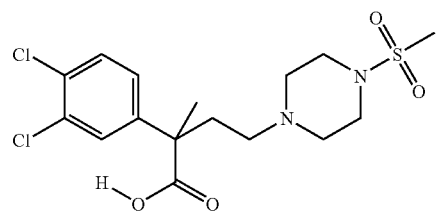

a) step 1: 3-(3,4-Dichloro-phenyl)-dihydro-furan-2-one (commercially available)

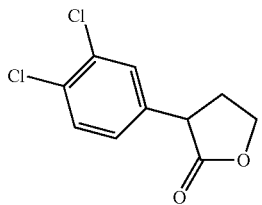

A mixture of 30 g (137 mmol) (3,4-dichloro-phenyl)-acetic acid methyl ester (commercially available), 6.47 g (151 mmol) NaH (55%) and 35.8 g (171 mmol) 2-(2-bromo-ethoxy)-tetrahydro-pyran in 100 mL DMF was stirred at room temperature for 17 h. The mixture was evaporated to dryness and partitioned between water and ethyl acetate. The combined organic phases were washed with NaCl aq., dried with Na$_2$SO$_4$ and evaporated. The residue was treated with 400 mL 4N HCl in dioxane in 250 mL methanol and stirred for 16 h at room temperature. The mixture was evaporated to dryness and subjected to column chromatography on silica eluting with a gradient formed from ethyl acetate and heptane. The combined product fractions were evaporated to yield 18.5 g (58%) of the title compound as yellow oil.

b) step 2: 3-(3,4-Dichloro-phenyl)-3-methyl-dihydro-furan-2-one

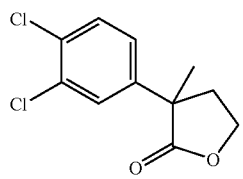

A mixture of 18.5 g (80 mmol) 3-(3,4-dichloro-phenyl)-dihydro-furan-2-one, 3.84 g (88 mmol) NaH (55% suspension) and 14.2 g (100 mmol) iodomethane in 300 mL THF was stirred for 64 h at room temperature. NH$_4$Cl aq. sat. was added and the mixture was extracted with ethyl acetate. The organic phases were washed with NaCl aq. sat. dried with Na$_2$SO$_4$, filtered and evaporated to dryness. The residue was purified by flash column chromatography on silica eluting with a gradient formed from ethyl acetate and heptane. The product containing fractions were evaporated to yield 16 g (82%) of the title compound as yellow oil. MS(m/e): 246.0 (MH$^+$).

c) step 3: 4-Bromo-2-(3,4-dichloro-phenyl)-2-methyl-butyric acid methyl ester

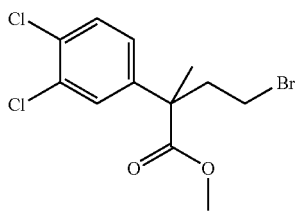

To a mixture of 3.3 g (13.5 mmol) 3-(3,4-dichloro-phenyl)-3-methyl-dihydro-furan-2-one in 15 mL acetic acid was added 48 mL HBr (33%) in acetic acid and after 63 h 20 mL HBr (33%) in acetic acid and stirred for another 21 h at room temperature. The mixture was pored onto ice-water and extracted with ethyl ether. The combined organic phases were washed with NaCl aq. sat., dried with Na$_2$SO$_4$, filtered and evaporated to dryness. The residue was taken up in 150 mL toluene and 6.5 mL (89 mmol) thionylchloride were added. The mixture was heated to 75° C. for 4 h, cooled to 0° C., treated with 20 mL methanol and allowed to stand for 16 h at room temperature. The mixture was evaporated to dryness and subjected to column chromatography on silica eluting with a gradient formed from ethyl acetate and heptane. The product containing fractions were evaporated to yield 4.32 g (94%) of the title compound as light yellow oil. MS(m/e): 341.9 (MH$^+$).

d) step 4: 2-(3,4-Dichloro-phenyl)-4-(4-methanesulfonyl-piperazin-1-yl)-2-methyl-butyric acid methyl ester

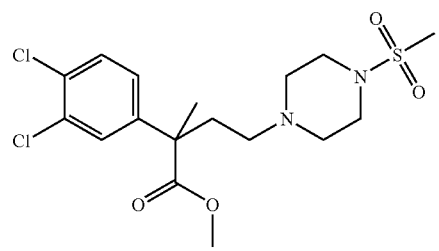

A mixture of 0.325 g (0.95 mmol) 4-bromo-2-(3,4-dichloro-phenyl)-2-methyl-butyric acid methyl ester, 0.667 g (4 mmol) 1-methanesulfonyl piperazine (commercially available) and 0.154 g (1.2 mmol) N,N-diisopropylethylamine in 2.5 mL DMF was heated to 50° C. for 42 h.

Another mixture of 1.2 g (3.5 mmol) 4-bromo-2-(3,4-dichloro-phenyl)-2-methyl-butyric acid methyl ester, 2.32 g (14 mmol) 1-methanesulfonyl piperazine (commercially available) and 0.722 g (5.5 mmol) N,N-diisopropylethylamine in 30 mL DMF was heated to 55° C. for 84 h. The two mixtures were combined, evaporated to dryness, suspended in a mixture formed from methanol and DCM and filtered. The precipitate was washed with DCM, isolute was added and evaporated to dryness. The residue was subjected to column chromatography on silica eluting with a gradient formed from DCM, methanol and NH$_3$ aq. The product containing fractions were evaporated to yield 1.16 g (61%) of the title compound as light yellow viscous oil. MS(m/e): 423.1 (MH$^+$).

e) step 5: 2-(3,4-Dichloro-phenyl)-4-(4-methanesulfonyl-piperazin-1-yl)-2-methyl-butyric acid A mixture of 1.15 g (2.7 mmol) 2-(3,4-dichloro-phenyl)-4-(4-methanesulfonyl-piperazin-1-yl)-2-methyl-butyric acid methyl ester and 0.171 g (4.08 mmol) LiOH.H$_2$O in 25 mL water and 25 mL THF was stirred at room temperature for 16 h. The mixture was treated with 4N HCl aq. and evaporated to dryness. The residue was used without further purification in the subsequent step. MS(m/e): 409.2 (MH$^+$).

Intermediate 3

2-(3,4-Dichloro-phenyl)-4-((R)-4-methanesulfonyl-3-methyl-piperazin-1-yl)-2-methyl-butyric acid

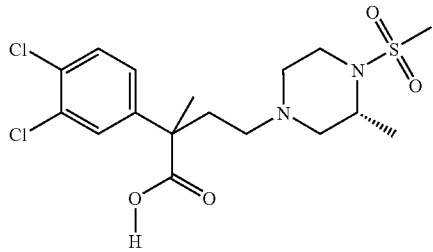

a) step 1: 2-(3,4-Dichloro-phenyl)-4-((R)-4-methanesulfonyl-3-methyl-piperazin-1-yl)-2-methyl-butyric acid methyl ester

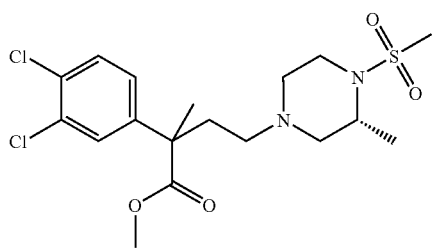

In analogy to the procedure described for the synthesis of 2-(3,4-dichloro-phenyl)-4-(4-methanesulfonyl-piperazin-1-yl)-2-methyl-butyric acid methyl ester (intermediate 2, step 4) the title compound was prepared from 4-bromo-2-(3,4-dichloro-phenyl)-2-methyl-butyric acid methyl ester (intermediate 2, step 3) and (R)-1-methanesulfonyl-2-methyl-piperazine (commercially available) in DMA as light brown viscous oil.

MS(m/e): 437.0 (MH$^+$).

b) step 2: 2-(3,4-Dichloro-phenyl)-4-((R)-4-methanesulfonyl-3-methyl-piperazin-1-yl)-2-methyl-butyric acid In analogy to the procedure described for the synthesis of 2-(3,4-dichloro-phenyl)-4-(4-methanesulfonyl-piperazin-1-yl)-2-methyl-butyric acid (intermediate 2, step 5) the title compound was prepared from 2-(3,4-dichloro-phenyl)-4-((R)-4-methanesulfonyl-3-methyl-piperazin-1-yl)-2-methyl-butyric acid methyl ester by saponification with LiOH.H$_2$O as yellow foam. MS(m/e): 423.1 (MH$^+$).

Intermediate 4

2-(3,4-Dichloro-phenyl)-4-((S)-4-methanesulfonyl-3-methyl-piperazin-1-yl)-2-methyl-butyric acid

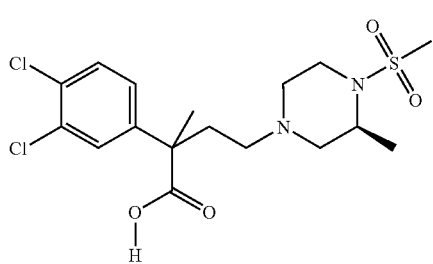

a) step 1: 2-(3,4-Dichloro-phenyl)-4-((S)-4-methanesulfonyl-3-methyl-piperazin-1-yl)-2-methyl-butyric acid methyl ester

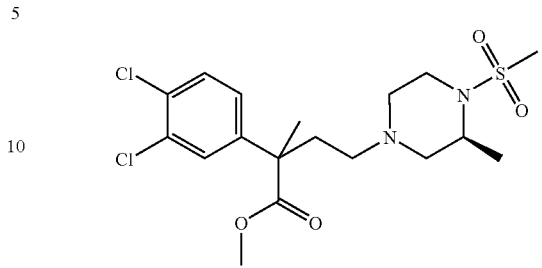

In analogy to the procedure described for the synthesis of 2-(3,4-dichloro-phenyl)-4-(4-methanesulfonyl-piperazin-1-yl)-2-methyl-butyric acid methyl ester (intermediate 2, step 4) the title compound was prepared from 4-bromo-2-(3,4-dichloro-phenyl)-2-methyl-butyric acid methyl ester (intermediate 2, step 3) and (S)-1-methanesulfonyl-2-methyl-piperazine (commercially available) in DMA as light brown viscous oil.

MS(m/e): 437.0 (MH$^+$).

b) step 2: 2-(3,4-Dichloro-phenyl)-4-((S)-4-methanesulfonyl-3-methyl-piperazin-1-yl)-2-methyl-butyric acid In analogy to the procedure described for the synthesis of 2-(3,4-dichloro-phenyl)-4-(4-methanesulfonyl-piperazin-1-yl)-2-methyl-butyric acid (intermediate 2, step 5) the title compound was prepared from 2-(3,4-dichloro-phenyl)-4-((S)-4-methanesulfonyl-3-methyl-piperazin-1-yl)-2-methyl-butyric acid methyl ester by saponification with LiOH.H$_2$O as yellow foam. MS(m/e): 423.1 (MH$^+$).

Intermediate 5

2-(3,4-Dichloro-phenyl)-4-(4-methanesulfonyl-[1,4]diazepan-1-yl)-2-methyl-butyric acid

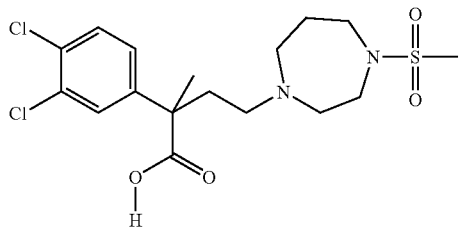

a) step 1: 2-(3,4-Dichloro-phenyl)-4-(4-methanesulfonyl-[1,4]diazepan-1-yl)-2-methyl-butyric acid methyl ester

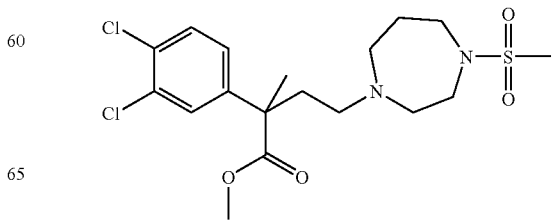

In analogy to the procedure described for the synthesis of 2-(3,4-dichloro-phenyl)-4-(4-methanesulfonyl-piperazin-1-yl)-2-methyl-butyric acid methyl ester (intermediate 2, step 4) the title compound was prepared from 4-bromo-2-(3,4-dichloro-phenyl)-2-methyl-butyric acid methyl ester (intermediate 2, step 3) and 1-methanesulfonyl-[1,4]diazepane (commercially available) in DMA as light brown viscous oil. MS(m/e): 437.2 (MH+).

b) step 2: 2-(3,4-Dichloro-phenyl)-4-(4-methanesulfonyl-[1,4]diazepan-1-yl)-2-methyl-butyric acid In analogy to the procedure described for the synthesis of 2-(3,4-dichloro-phenyl)-4-(4-methanesulfonyl-piperazin-1-yl)-2-methyl-butyric acid (intermediate 2, step 5) the title compound was prepared from 2-(3,4-dichloro-phenyl)-4-(4-methanesulfonyl-[1,4]diazepan-1-yl)-2-methyl-butyric acid methyl ester by saponification with LiOH.H₂O as yellow foam. MS(m/e): 423.1 (MH+).

Intermediate 6

2-(3,4-Dichloro-phenyl)-4-(1,1-dioxo-hexahydro-1λ⁶-thia-5,7a-diaza-inden-5-yl)-2-methyl-butyric acid

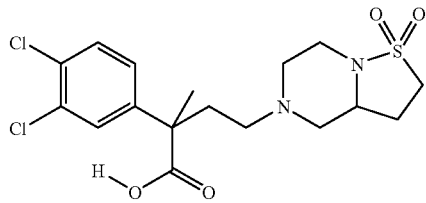

a) step 1: 2-(3,4-Dichloro-phenyl)-4,4-dimethoxy-2-methyl-butyric acid methyl ester

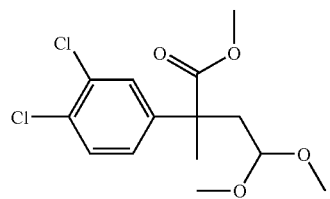

A mixture of 35 g (150 mmol) 2-(3,4-dichloro-phenyl)-propionic acid methyl ester (*Journal of Medicinal Chemistry* (2004), 47(23), 5753-5765), 31.7 g (188 mmol) bromoacetaldehyde dimethyl acetal (commercially available and 6.6 g (165 mmol) NaH (55%) in 100 mL DMF was stirred at room temperature and afterwards evaporated to dryness. Ice water and ethyl acetate was added and the organic fraction was washed with sat. NaCl aq., dried with Na₂SO₄ and evaporated. The residue was purified by column chromatography on silica eluting with a mixture of ethyl acetate and hexane. The product containing fractions were evaporated to yield 29.6 g (61%) of the title compound as yellow liquid.

b) step 2: 2-(3,4-Dichloro-phenyl)-2-methyl-4-oxo-butyric acid methyl ester

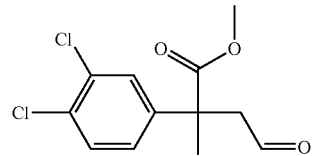

A mixture of 6 g (19 mmol) 2-(3,4-dichloro-phenyl)-4,4-dimethoxy-2-methyl-butyric acid methyl ester and 28 mL 2N HCl aq. in 60 mL THF and 60 mL water was stirred at room temperature for 20 h. The mixture was extracted with diethyl ether. The combined organic phases were washed with sat. NaCl aq., dried with Na₂SO₄ and evaporated to dryness. The residue was subjected to column chromatography on silica eluting with a gradient formed from ethyl acetate and hexane. The product containing fractions were evaporated to yield 3 g (58%) of the title compound as light yellow oil.

c) step 3: 2-(3,4-Dichloro-phenyl)-4-(1,1-dioxo-hexahydro-1λ⁶-thia-5,7a-diaza-inden-5-yl)-2-methyl-butyric acid methyl ester

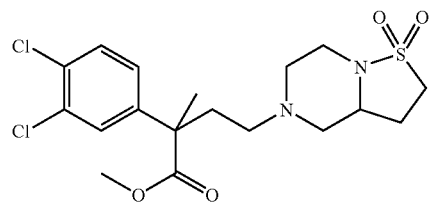

A mixture of 0.8 g (2.9 mmol) 2-(3,4-dichloro-phenyl)-2-methyl-4-oxo-butyric acid methyl ester, 0.742 g (3.48 mmol) 2H-isothiazolo[2,3-a]pyrazine, hexahydro-1,1-dioxide (WO 2007/028654), 0.924 g (4.36 mmol) sodium triacetoxyborohydride, 0.26 g (4.3 mmol) acetic acid and 0.353 g (3.5 mmol) NEt₃ in 80 mL DCM was stirred at room temperature. Na₂CO₃ aq. (10%) was added and the organic phase was washed with sat. NaCl aq., dried with Na₂SO₄ and evaporated. The residue was subjected to column chromatography on silica eluting with a gradient formed from DCM, methanol and NH₃ aq. (2N). The product containing fractrions were evaporated to yield 1.18 g (92%) of the title compound as colorless viscous oil. MS(m/e): 435.2 (MH+).

d) step 4: 2-(3,4-Dichloro-phenyl)-4-(1,1-dioxo-hexahydro-1λ⁶-thia-5,7a-diaza-inden-5-yl)-2-methyl-butyric acid A mixture of 1.16 g (2.6 mmol) 2-(3,4-dichloro-phenyl)-4-(1,1-dioxo-hexahydro-1λ⁶-thia-5,7a-diaza-inden-5-yl)-2-methyl-butyric acid methyl ester and 0.123 g (2.9 mmol) LiOH.H₂O in 40 mL water and 40 mL THF was stirred at room temperature for 48 h. After evaporation of THF the pH was adjusted to pH=2 with 2N HCl aq., evaporated to dryness, taken up in acetonitrile and evaporated (3×), The residue was dried at 60° C. under high vacuum and used without further purification in the consecutive amide coupling step. MS(m/e): 421.0 (MH+).

EXAMPLE 1

N-(4-Chloro-benzyl)-2-(3,4-dichloro-phenyl)-4-(4-methanesulfonyl-piperazin-1-yl)-N-methyl-butyramide

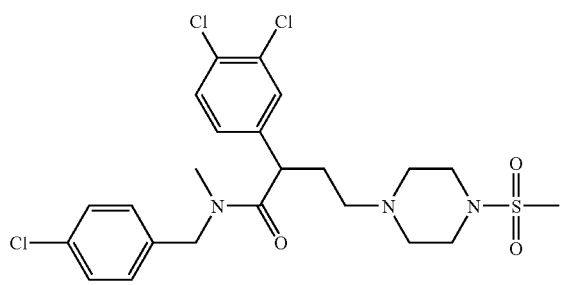

A mixture of 25 mg 2-(3,4-dichloro-phenyl)-4-(4-methanesulfonyl-piperazin-1-yl)-butyric acid (intermediate 1), 24.1 mg (0.075 mmol) TBTU, 11.67 mg (0.075 mmol) (4-chloro-benzyl)-methyl-amine (commercially available) and 0.06 mL N,N-diisopropyl ethylamine in 0.75 mL DMF was shaken at room temperature and subsequently subjected to purification by preparative HPLC on reversed phase eluting with a gradient formed from acetonitrile, water and NEt$_3$. The product containing fractions were evaporated to yield 20.7 mg (67%) of the title compound as yellow viscous oil. MS(m/e): 534.2 (MH$^+$).

In analogy to the procedure described for the synthesis of N-(4-chloro-benzyl)-2-(3,4-dichloro-phenyl)-4-(4-methanesulfonyl-piperazin-1-yl)-N-methyl-butyramide (example 1) further piperazine derivatives have been synthesized from the starting materials listed in Table 2. Table 2 comprises examples 2-92.

TABLE 2

| No | MW | structure | Systematic Name | starting materials | MW found MH+ |
|---|---|---|---|---|---|
| 2 | 575.6 | 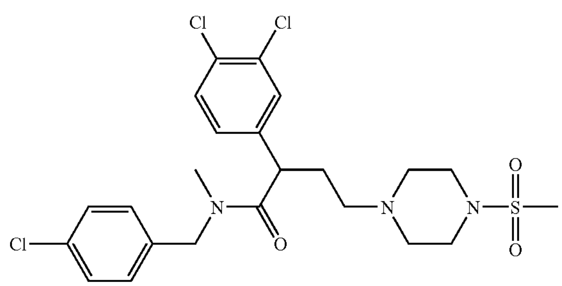 | 2-(3,4-Dichloro-phenyl)-4-(4-methanesulfonyl-piperazin-1-yl)-N-methyl-N-(4-pyridin-4-yl-benzyl)-butyramide | 2-(3,4-Dichloro-phenyl)-4-(4-methanesulfonyl-piperazin-1-yl)-butyric acid (intermediate 1) and Methyl-(4-pyridin-4-yl-benzyl)-amine (commercially available) | 575.3 |
| 3 | 532.9 | 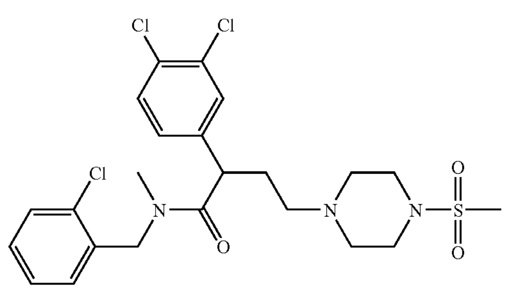 | N-(2-Chloro-benzyl)-2-(3,4-Dichloro-phenyl)-4-(4-methanesulfonyl-piperazin-1-yl)-N-methyl-butyramide | 2-(3,4-Dichloro-phenyl)-4-(4-methanesulfonyl-piperazin-1-yl)-butyric acid (intermediate 1) and (2-Chloro-benzyl)-methyl-amine (commercially available) | 534.2 |
| 4 | 498.5 | 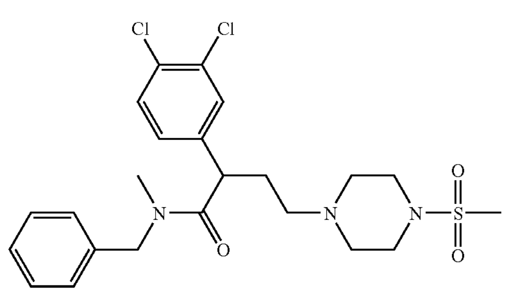 | N-Benzyl-2-(3,4-dichloro-phenyl)-4-(4-methanesulfonyl-piperazin-1-yl)-N-methyl-butyramide | 2-(3,4-Dichloro-phenyl)-4-(4-methanesulfonyl-piperazin-1-yl)-butyric acid (intermediate 1) and Benzyl-methyl-amine (commercially available) | 498.3 |

TABLE 2-continued

| No | MW | structure | Systematic Name | starting materials | MW found MH+ |
|---|---|---|---|---|---|
| 5 | 566.5 | 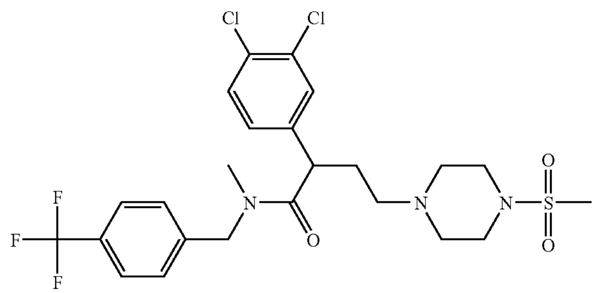 | 2-(3,4-Dichloro-phenyl)-4-(4-methanesulfonyl-piperazin-1-yl)-N-methyl-N-(4-trifluoromethyl-benzyl)-butyramide | 2-(3,4-Dichloro-phenyl)-4-(4-methanesulfonyl-piperazin-1-yl)-butyric acid (intermediate 1) and Methyl-(4-trifluoromethyl-benzyl)-amine (commercially available) | 566.3 |
| 6 | 546.5 | 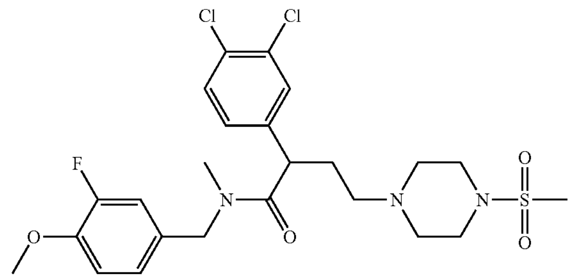 | 2-(3,4-Dichloro-phenyl)-N-(3-fluoro-4-methoxy-benzyl)-4-(4-methanesulfonyl-piperazin-1-yl)-N-methyl-butyramide | 2-(3,4-Dichloro-phenyl)-4-(4-methanesulfonyl-piperazin-1-yl)-butyric acid (intermediate 1) and (3-Fluoro-4-methoxy-benzyl)-methyl-amine (commercially available) | 546.1 |
| 7 | 516.5 | 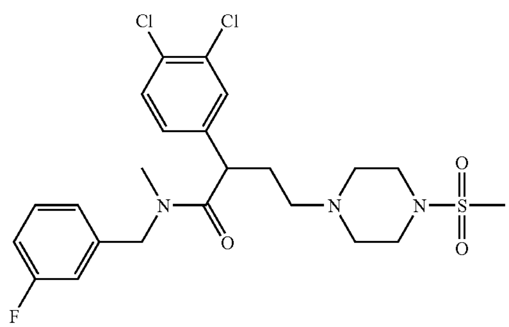 | 2-(3,4-Dichloro-phenyl)-N-(3-fluoro-benzyl)-4-(4-methanesulfonyl-piperazin-1-yl)-N-methyl-butyramide | 2-(3,4-Dichloro-phenyl)-4-(4-methanesulfonyl-piperazin-1-yl)-butyric acid (intermediate 1) and (3-Fluoro-benzyl)-methyl-amine (commercially available) | 516.2 |
| 8 | 566.5 | 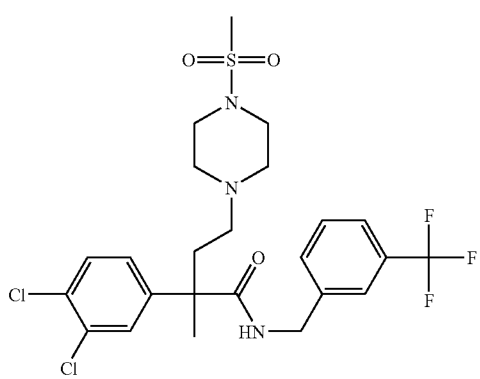 | 2-(3,4-Dichloro-phenyl)-4-(4-methanesulfonyl-piperazin-1-yl)-2-methyl-N-(3-trifluoromethyl-benzyl)-butyramide | 2-(3,4-Dichloro-phenyl)-4-(4-methanesulfonyl-piperazin-1-yl)-2-methyl-butyric acid (intermediate 2) and 3-Trifluoromethyl-benzylamine (commercially available) | 566.3 |

TABLE 2-continued

| No | MW | structure | Systematic Name | starting materials | MW found MH+ |
|---|---|---|---|---|---|
| 9 | 582.5 | 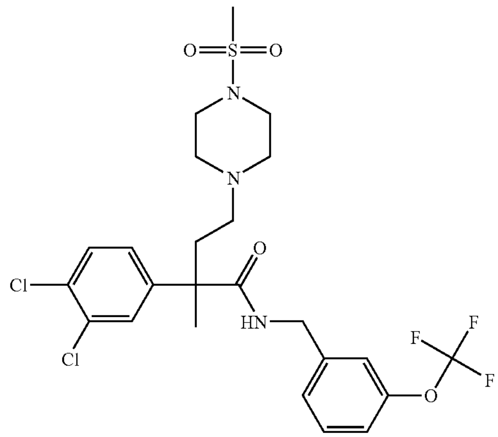 | 2-(3,4-Dichloro-phenyl)-4-(4-methanesulfonyl-piperazin-1-yl)-2-methyl-N-(3-trifluoromethoxy-benzyl)-butyramide | 2-(3,4-Dichloro-phenyl)-4-(4-methanesulfonyl-piperazin-1-yl)-2-methyl-butyric acid (intermediate 2) and 3-Trifluoromethoxy-benzylamine (commercially available) | 582.2 |
| 10 | 546.9 | 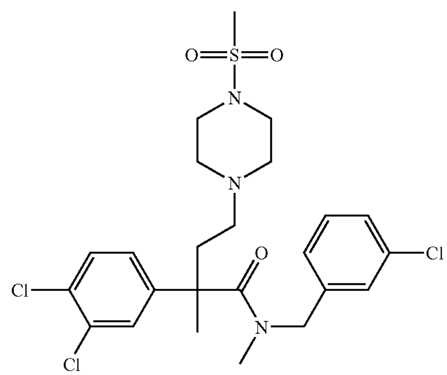 | N-(3-Chloro-benzyl)-2-(3,4-Dichloro-phenyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and (3-Chloro-benzyl)-methyl-amine (commercially available) | 546.2 |
| 11 | 564.5 | 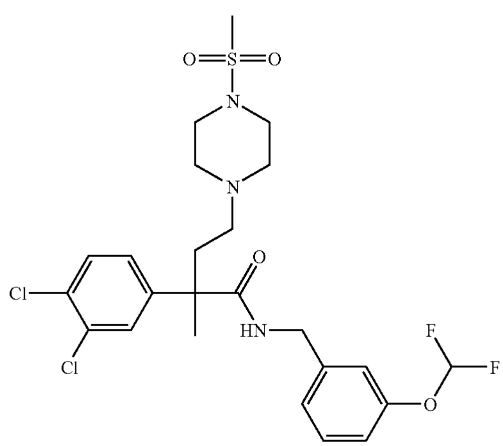 | 2-(3,4-Dichloro-phenyl)-N-(3-difluoromethoxy-benzyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 3-Difluoromethoxy-benzylamine (commercially available) | 564.2 |

TABLE 2-continued

| No | MW | structure | Systematic Name | starting materials | MW found MH+ |
|---|---|---|---|---|---|
| 12 | 546.9 | 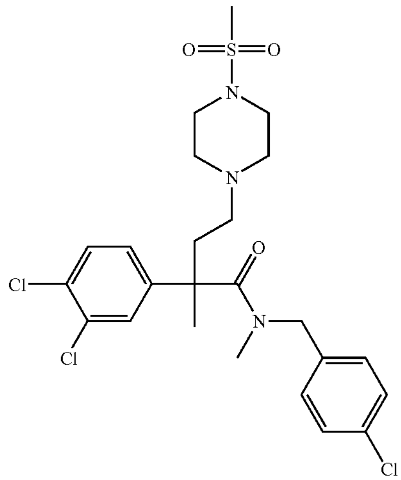 | N-(4-Chloro-benzyl)-2-(3,4-Dichloro-phenyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and (4-Chloro-benzyl)-methyl-amine (commercially available) | 546.1 |
| 13 | 564.5 | 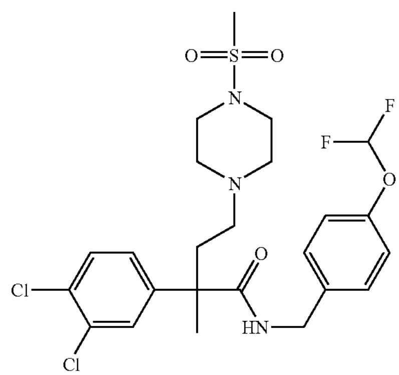 | 2-(3,4-Dichloro-phenyl)-N-(4-difluoromethoxy-benzyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 4-Difluoromethoxy-benzylamine (commercially available) | 564.2 |
| 14 | 546.9 | 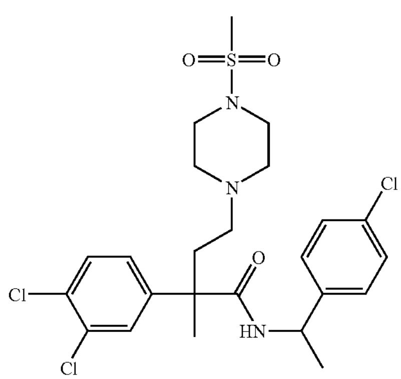 | N-[1-(4-Chloro-phenyl)-ethyl]-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 1-(4-Chloro-phenyl)-ethylamine (commercially available) | 546.2 |

TABLE 2-continued

| No | MW | structure | Systematic Name | starting materials | MW found MH+ |
|---|---|---|---|---|---|
| 15 | 568.6 | 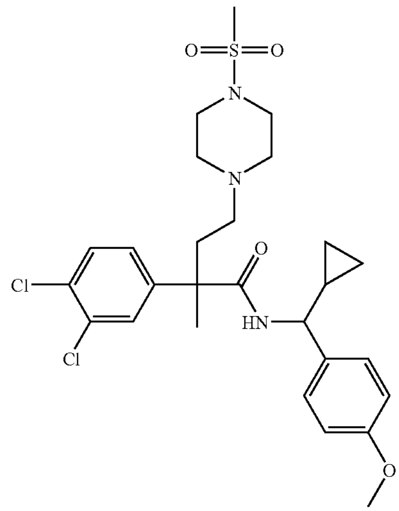 | N-[Cyclopropyl-(4-methoxy-phenyl)-methyl]-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and C-Cyclopropyl-C-(4-methoxy-phenyl)-methylamine (commercially available) | 568.4 |
| 16 | 546.9 | 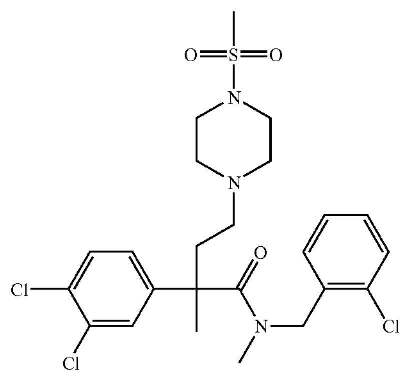 | N-(2-Chloro-benzyl)-2-(3,4-Dichloro-phenyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and (2-Chloro-benzyl)-methyl-amine (commercially available) | 546.2 |
| 17 | 582.5 | 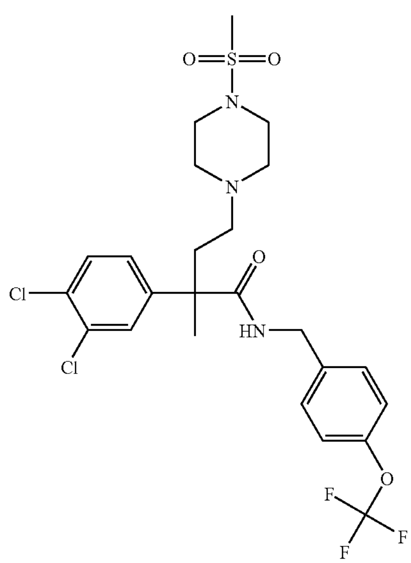 | 2-(3,4-Dichloro-phenyl)-4-(4-methanesulfonyl-piperazin-1-yl)-2-methyl-N-(4-trifluoromethoxy-benzyl)-butyramide | 2-(3,4-Dichloro-phenyl)-4-(4-methanesulfonyl-piperazin-1-yl)-2-methyl-butyric acid (intermediate 2) and 4-Trifluoromethoxy-benzylamine (commercially available) | 582 |

TABLE 2-continued

| No | MW | structure | Systematic Name | starting materials | MW found MH+ |
|---|---|---|---|---|---|
| 18 | 523.5 | 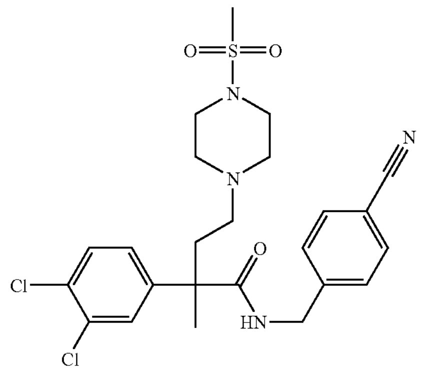 | N-(4-Cyano-benzyl)-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 4-Aminomethyl-benzonitrile (commercially available) | 523.3 |
| 19 | 582.5 | 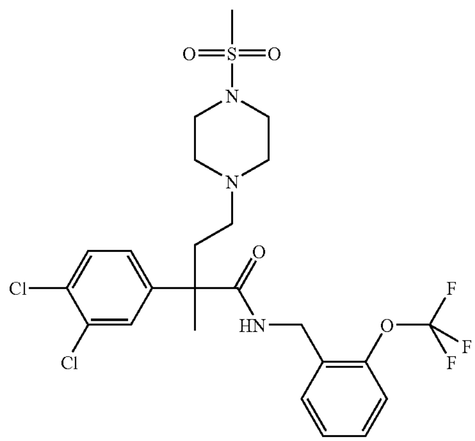 | 2-(3,4-Dichloro-phenyl)-4-(4-methanesulfonyl-piperazin-1-yl)-2-methyl-N-(2-trifluoromethoxy-benzyl)-butyramide | 2-(3,4-Dichloro-phenyl)-4-(4-methanesulfonyl-piperazin-1-yl)-2-methyl-butyric acid (intermediate 2) and 2-Trifluoromethoxy-benzylamine (commercially available) | 582.2 |
| 20 | 584.5 | 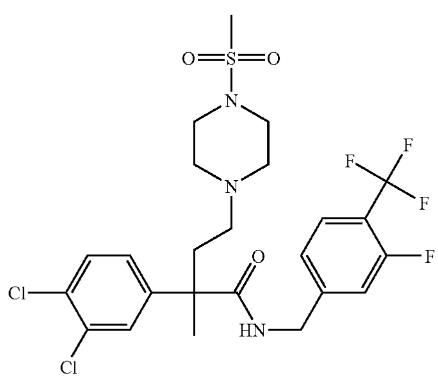 | 2-(3,4-Dichloro-phenyl)-N-(3-fluoro-4-trifluoromethyl-benzyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 3-Fluoro-4-trifluoromethyl-benzylamine (commercially available) | 584 |
| 21 | 567.4 | 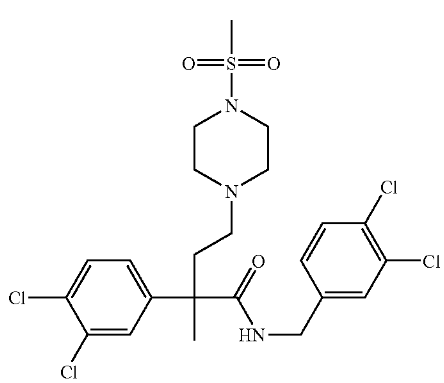 | N-(3,4-Dichloro-benzyl)-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 3,4-Dichloro-benzylamine (commercially available) | 568 |

TABLE 2-continued

| No | MW | structure | Systematic Name | starting materials | MW found MH+ |
|---|---|---|---|---|---|
| 22 | 526.5 | 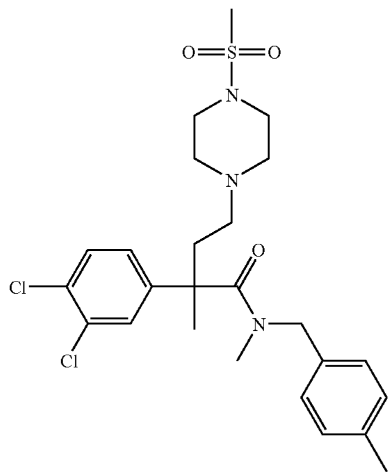 | 2-(3,4-Dichloro-phenyl)-4-(4-methanesulfonyl-piperazin-1-yl)-2,N-dimethyl-N-(4-methyl-benzyl)-butyramide | 2-(3,4-Dichloro-phenyl)-4-(4-methanesulfonyl-piperazin-1-yl)-2-methyl-butyric acid (intermediate 2) and Methyl-(4-methyl-benzyl)-amine (commercially available) | 526.3 |
| 23 | 589.6 | 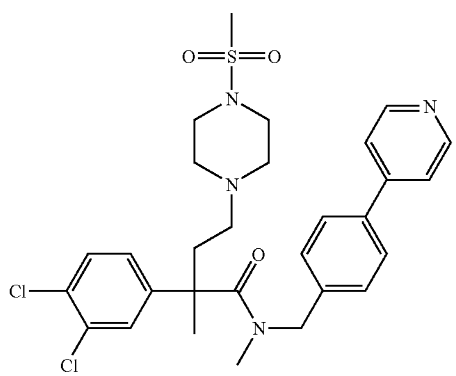 | 2-(3,4-Dichloro-phenyl)-4-(4-methanesulfonyl-piperazin-1-yl)-2,N-dimethyl-N-(4-pyridin-4-yl-benzyl)-butyramide | 2-(3,4-Dichloro-phenyl)-4-(4-methanesulfonyl-piperazin-1-yl)-2-methyl-butyric acid (intermediate 2) and Methyl-(4-pyridin-4-yl-benzyl)-amine (commercially available) | 589.3 |
| 24 | 530.5 | 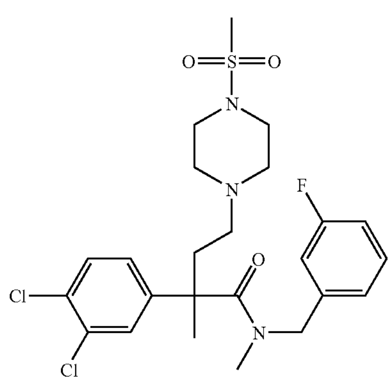 | 2-(3,4-Dichloro-phenyl)-N-(3-fluoro-benzyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and 3-Fluoro-benzyl)-methyl-amine (commercially available) | 530.2 |

TABLE 2-continued

| No | MW | structure | Systematic Name | starting materials | MW found MH+ |
|---|---|---|---|---|---|
| 25 | 560.5 | 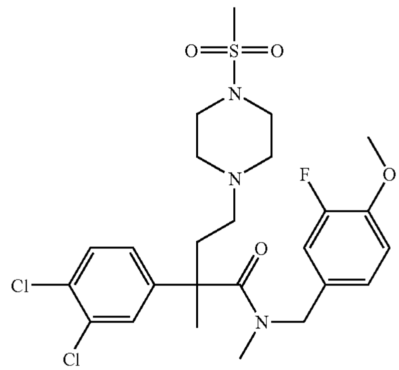 | 2-(3,4-Dichloro-phenyl)-N-(3-fluoro-4-methoxy-benzyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and (3-Fluoro-4-methoxy-benzyl)-methyl-amine (commercially available) | 560.3 |
| 26 | 608.5 | 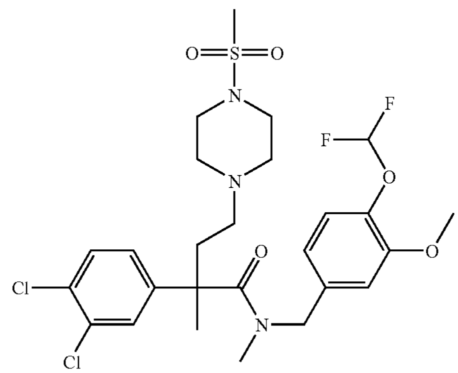 | 2-(3,4-Dichloro-phenyl)-N-(4-difluoromethoxy-3-methoxy-benzyl)-4-(4-methanesulfonyl-piperazin-1-yl)-2,N-dimethyl-butyramide | 2-(3,4-Dichloro-phenyl)-4-(4-methanesulfonyl-piperazin-1-yl)-2-methyl-butyric acid (intermediate 2) and (4-Difluoromethoxy-3-methoxy-benzyl)-methyl-amine (commercially available) | 608 |
| 27 | 566.5 | 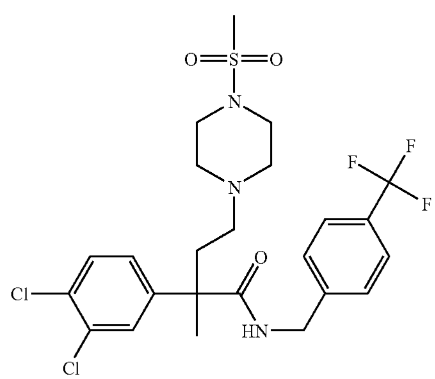 | 2-(3,4-Dichloro-phenyl)-4-(4-methanesulfonyl-piperazin-1-yl)-2-methyl-N-(4-trifluoromethyl-benzyl)-butyramide | 2-(3,4-Dichloro-phenyl)-4-(4-methanesulfonyl-piperazin-1-yl)-2-methyl-butyric acid (intermediate 2) and 4-Trifluoromethyl-benzylamine (commercially available) | 566.3 |
| 28 | 580.5 | 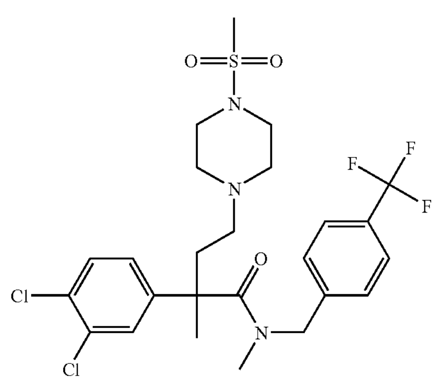 | 2-(3,4-Dichloro-phenyl)-4-(4-methanesulfonyl-piperazin-1-yl)-2,N-dimethyl-N-(4-trifluoromethyl-benzyl)-butyramide | 2-(3,4-Dichloro-phenyl)-4-(4-methanesulfonyl-piperazin-1-yl)-2-methyl-butyric acid (intermediate 2) and Methyl-(4-trifluoromethyl-benzyl)-amine (commercially available) | 580.3 |

TABLE 2-continued

| No | MW | structure | Systematic Name | starting materials | MW found MH+ |
|---|---|---|---|---|---|
| 29 | 532.9 | 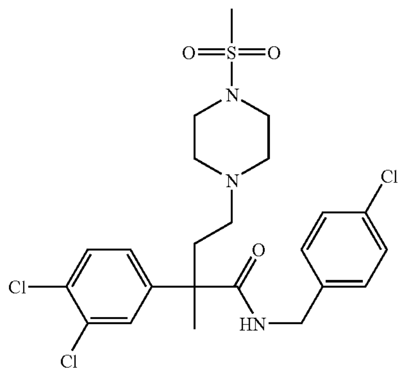 | N-(4-Chloro-benzyl)-2-(3,4-Dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 4-Chloro-benzylamine (commercially available) | 534 |
| 30 | 550.9 | 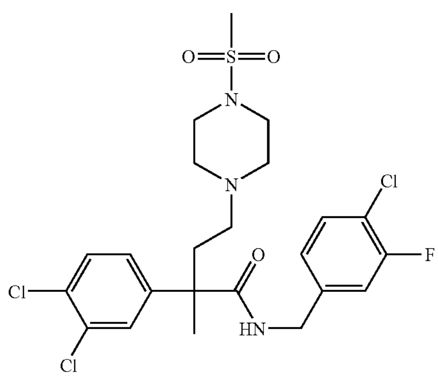 | N-(4-Chloro-3-fluoro-benzyl)-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 4-Chloro-3-fluoro-benzylamine (commercially available) | 552.3 |
| 31 | 574.5 | 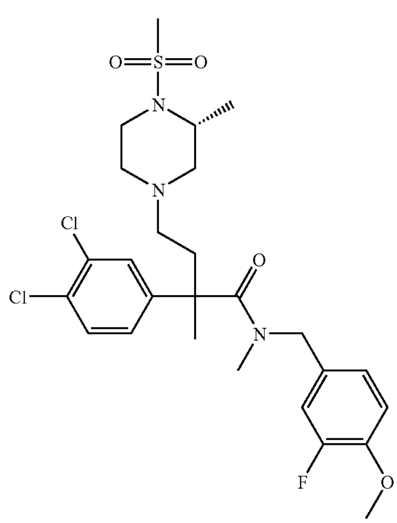 | 2-(3,4-Dichloro-phenyl)-N-(3-fluoro-4-methoxy-benzyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (3-Fluoro-4-methoxy-benzyl)-methyl-amine (commercially available) | 574.3 |

TABLE 2-continued

| No | MW | structure | Systematic Name | starting materials | MW found MH+ |
|---|---|---|---|---|---|
| 32 | 582.6 | 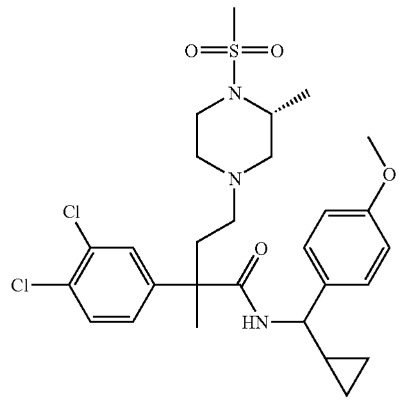 | N-[Cyclopropyl-(4-methoxy-phenyl)-methyl]-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and C-Cyclopropyl-C-(4-methoxy-phenyl)-methylamine (commercially available) | 584.1 |
| 33 | 612.5 | 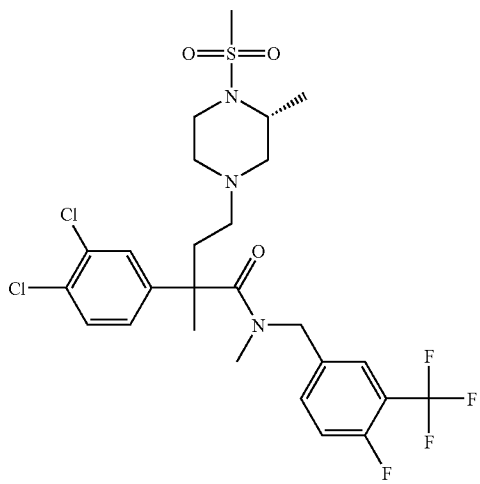 | 2-(3,4-Dichloro-phenyl)-N-(4-fluoro-3-trifluoromethyl-benzyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (4-Fluoro-3-trifluoromethyl-benzyl)-methyl-amine (commercially available) | 612.2 |
| 34 | 648.5 | 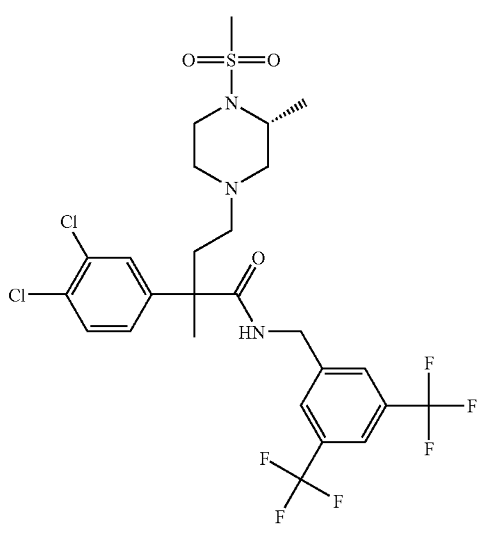 | N-(3,5-Bis-trifluoromethyl-benzyl)-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 3,5-Bis-trifluoromethyl-benzylamine (commercially available) | 648.1 |

TABLE 2-continued

| No | MW | structure | Systematic Name | starting materials | MW found MH+ |
|---|---|---|---|---|---|
| 35 | 622.6 | 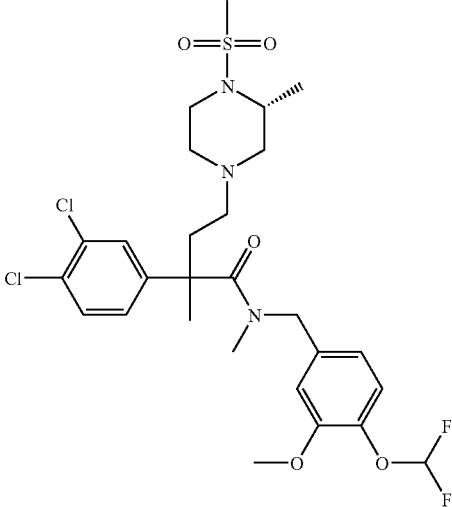 | 2-(3,4-Dichloro-phenyl)-N-(4-difluoromethoxy-3-methoxy-benzyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (4-Difluoromethoxy-3-methoxy-benzyl)-methyl-amine (commercially available) | 622.2 |
| 36 | 540.6 | 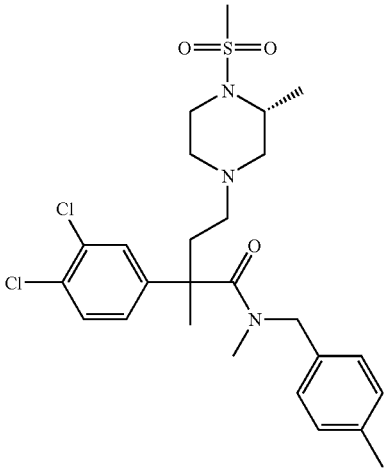 | 2-(3,4-Dichloro-phenyl)-4-((R)-4-methanesulfonyl-3-methyl-piperazin-1-yl)-2,N-dimethyl-N-(4-methyl-benzyl)-butyramide | 2-(3,4-Dichloro-phenyl)-4-((R)-4-methanesulfonyl-3-methyl-piperazin-1-yl)-2-methyl-butyric acid (intermediate 3) and Methyl-(4-methyl-benzyl)-amine (commercially available) | 540.4 |
| 37 | 555.6 | 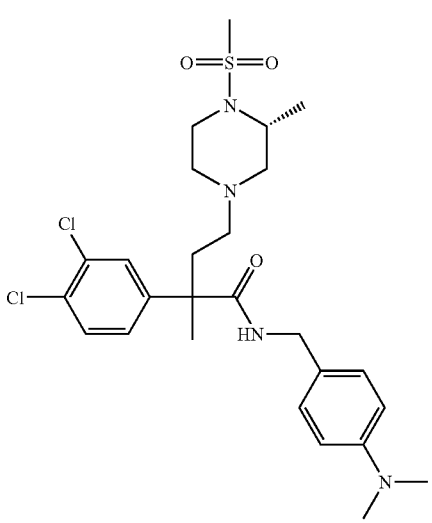 | 2-(3,4-Dichloro-phenyl)-N-(4-dimethylamino-benzyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and (4-Aminomethyl-phenyl)-dimethyl-amine (commercially available) | 555.2 |

TABLE 2-continued

| No | MW | structure | Systematic Name | starting materials | MW found MH+ |
|---|---|---|---|---|---|
| 38 | 564.5 | 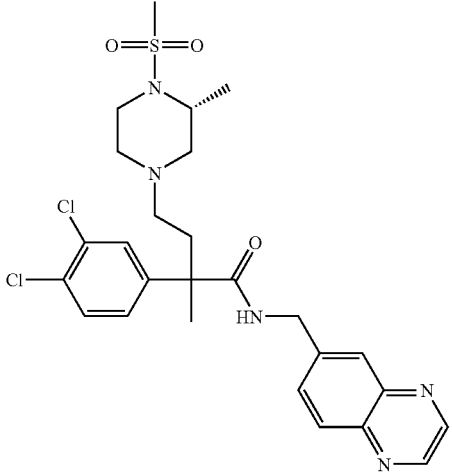 | 2-(3,4-Dichloro-phenyl)-4-((R)-4-methanesulfonyl-3-methyl-piperazin-1-yl)-2-methyl-N-quinoxalin-6-ylmethyl-butyramide | 2-(3,4-Dichloro-phenyl)-4-((R)-4-methanesulfonyl-3-methyl-piperazin-1-yl)-2-methyl-butyric acid (intermediate 3) and C-Quinoxalin-6-yl-methylamine (commercially available) | 564.3 |
| 39 | 629.0 | 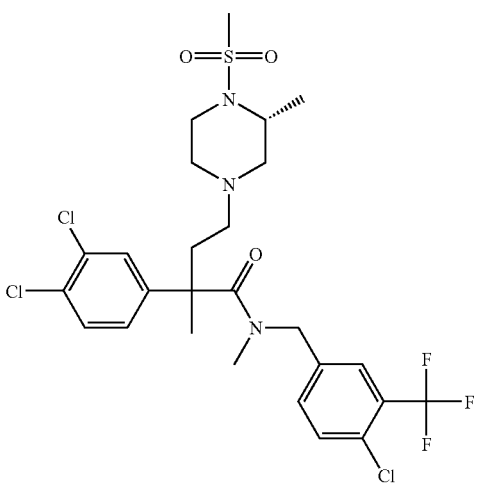 | N-(4-Chloro-3-trifluoromethyl-benzyl)-2-(3,4-dichloro-phenyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (4-Chloro-3-trifluoromethyl-benzyl)-methyl-amine (commercially available) | 628.2 |
| 40 | 612.5 | 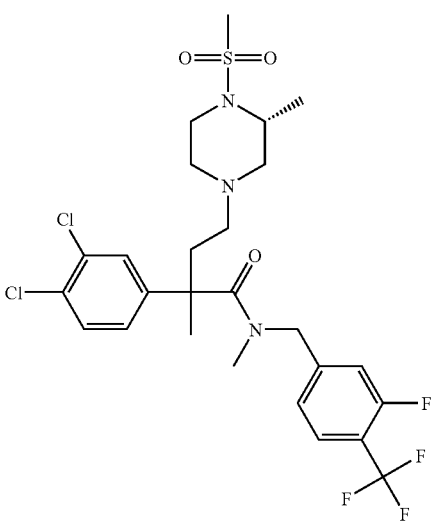 | 2-(3,4-Dichloro-phenyl)-N-(3-fluoro-4-trifluoromethyl-benzyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (3-Fluoro-4-trifluoromethyl-benzyl)-methyl-amine (commercially available) | 612.2 |

TABLE 2-continued

| No | MW | structure | Systematic Name | starting materials | MW found MH+ |
|---|---|---|---|---|---|
| 41 | 595.4 | 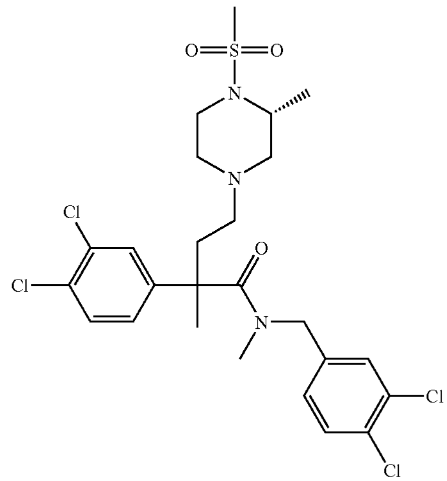 | N-(3,4-Dichloro-benzyl)-2-(3,4-dichloro-phenyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (3,4-Dichloro-benzyl)-methyl-amine (commercially available) | 596.1 |
| 42 | 581.4 | 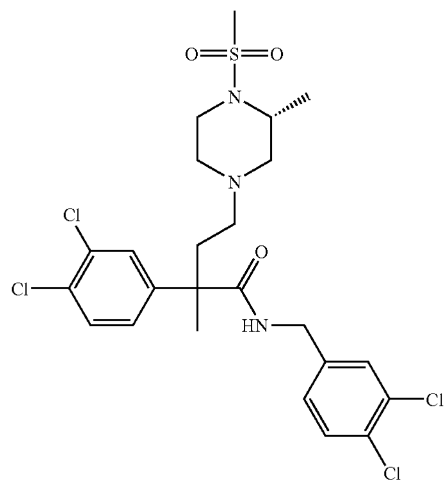 | N-(3,4-Dichloro-benzyl)-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 3,4-Dichloro-benzylamine (commercially available) | 582 |
| 43 | 578.5 | 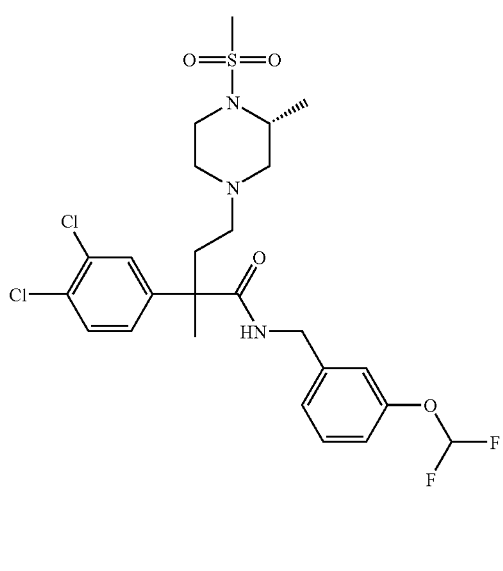 | 2-(3,4-Dichloro-phenyl)-N-(3-difluoromethoxy-benzyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 3-Difluoromethoxy-benzylamine (commercially available) | 578.1 |

| No | MW | structure | Systematic Name | starting materials | MW found MH+ |
|---|---|---|---|---|---|
| 44 | 598.5 | 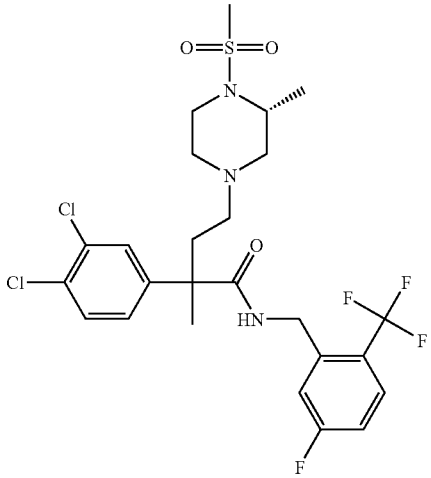 | 2-(3,4-Dichloro-phenyl)-N-(5-fluoro-2-trifluoromethyl-benzyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 5-Fluoro-2-trifluoromethyl-benzylamine (commercially available) | 598.2 |
| 45 | 580.5 | 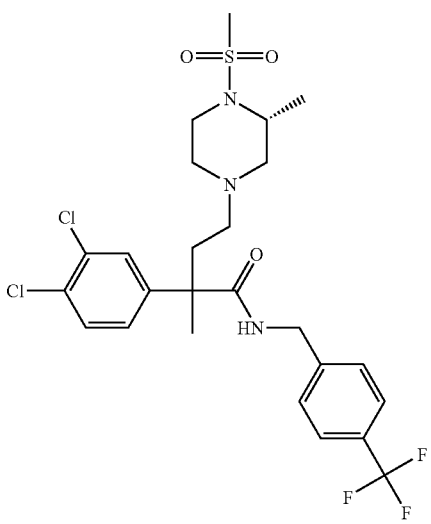 | 2-(3,4-Dichloro-phenyl)-4-((R)-4-methanesulfonyl-3-methyl-piperazin-1-yl)-2-methyl-N-(4-trifluoromethyl-benzyl)-butyramide | 2-(3,4-Dichloro-phenyl)-4-((R)-4-methanesulfonyl-3-methyl-piperazin-1-yl)-2-methyl-butyric acid (intermediate 3) and 4-Trifluoromethyl-benzylamine (commercially available) | 580.1 |
| 46 | 598.5 | 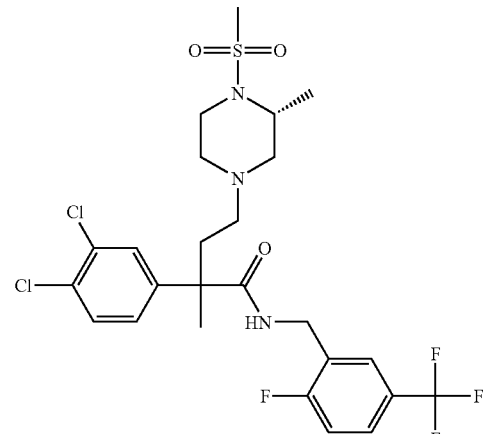 | 2-(3,4-Dichloro-phenyl)-N-(2-fluoro-5-trifluoromethyl-benzyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 2-Fluoro-5-trifluoromethyl-benzylamine (commercially available) | 598.1 |

TABLE 2-continued

| No | MW | structure | Systematic Name | starting materials | MW found MH+ |
|---|---|---|---|---|---|
| 47 | 561.0 | 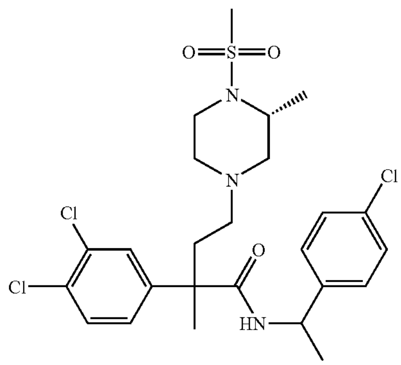 | N-[1-(4-Chloro-phenyl)-ethyl]-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 1-(4-Chloro-phenyl)-ethylamine (commercially available) | 562.5 |
| 48 | 556.6 | 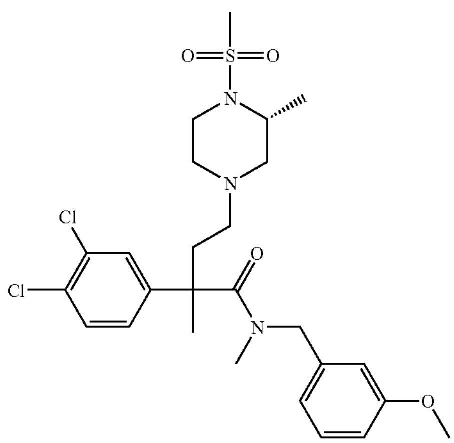 | 2-(3,4-Dichloro-phenyl)-4-((R)-4-methanesulfonyl-3-methyl-piperazin-1-yl)-N-(3-methoxy-benzyl)-2,N-dimethyl butyramide | 2-(3,4-Dichloro-phenyl)-4-((R)-4-methanesulfonyl-3-methyl-piperazin-1-yl)-2-methyl-butyric acid (intermediate 3) and (3-Methoxy-benzyl)-methyl-(commercially available) | 556.3 |
| 49 | 561.0 | 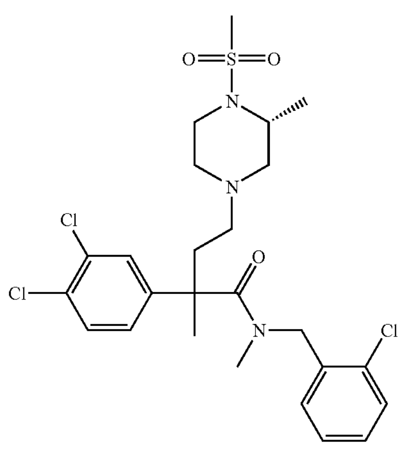 | N-(2-Chloro-benzyl)-2-(3,4-Dichloro-phenyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (2-Chloro-benzyl)-methyl-amine (commercially available) | 560.3 |

TABLE 2-continued

| No | MW | structure | Systematic Name | starting materials | MW found MH+ |
|---|---|---|---|---|---|
| 50 | 595.4 | 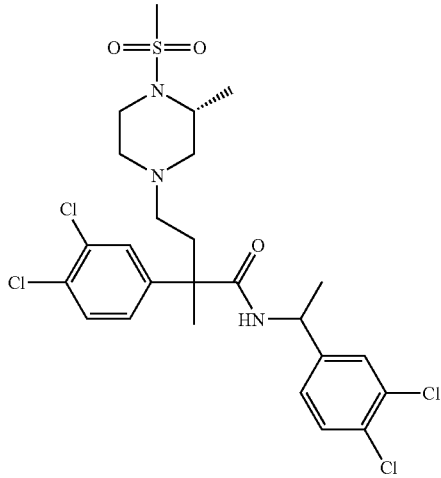 | 2-(3,4-Dichloro-phenyl)-N-[1-(3,4-dichloro-phenyl)-ethyl]-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 1-(3,4-Dichloro-phenyl)-ethylamine (commercially available) | 596.3 |
| 51 | 596.5 | 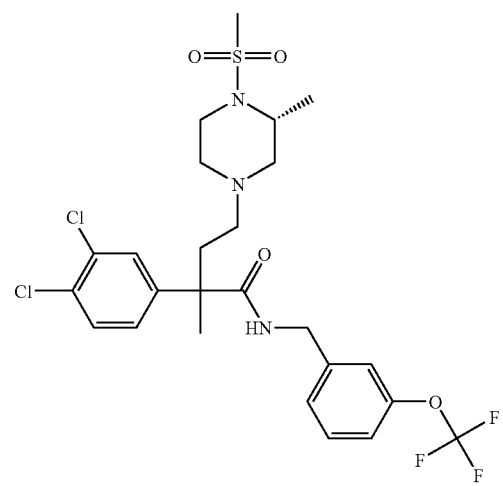 | 2-(3,4-Dichloro-phenyl)-4-((R)-4-methanesulfonyl-3-methyl-piperazin-1-yl)-2-methyl-N-(3-trifluoromethoxy-benzyl)-butyramide | 2-(3,4-Dichloro-phenyl)-4-((R)-4-methanesulfonyl-3-methyl-piperazin-1-yl)-2-methyl-butyric acid (intermediate 3) and 3-Trifluoromethoxy-benzylamine (commercially available) | 596.2 |
| 52 | 564.9 | 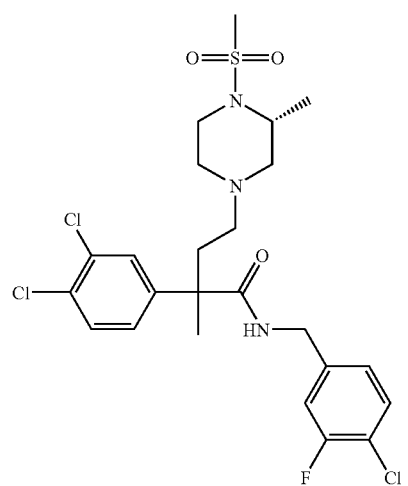 | N-(4-Chloro-3-fluoro-benzyl)-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 3-Chloro-4-fluoro-benzylamine (commercially available) | 564.3 |

TABLE 2-continued

| No | MW | structure | Systematic Name | starting materials | MW found MH+ |
|---|---|---|---|---|---|
| 53 | 596.5 | 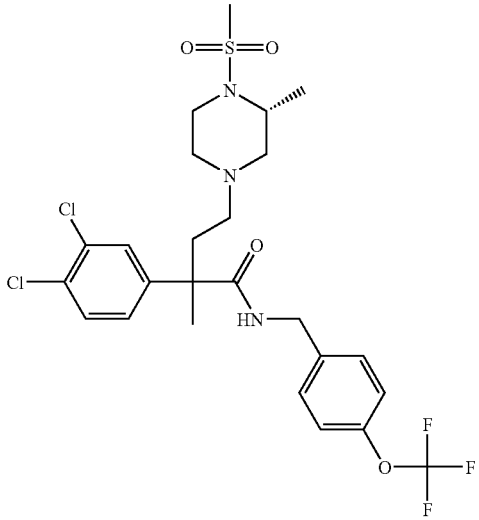 | 2-(3,4-Dichloro-phenyl)-4-((R)-4-methanesulfonyl-3-methyl-piperazin-1-yl)-2-methyl-N-(4-trifluoromethoxy-benzyl)-butyramide | 2-(3,4-Dichloro-phenyl)-4-((R)-4-methanesulfonyl-3-methyl-piperazin-1-yl)-2-methyl-butyric acid (intermediate 3) and 4-Trifluoromethoxy-benzylamine (commercially available) | 596.2 |
| 54 | 614.9 | 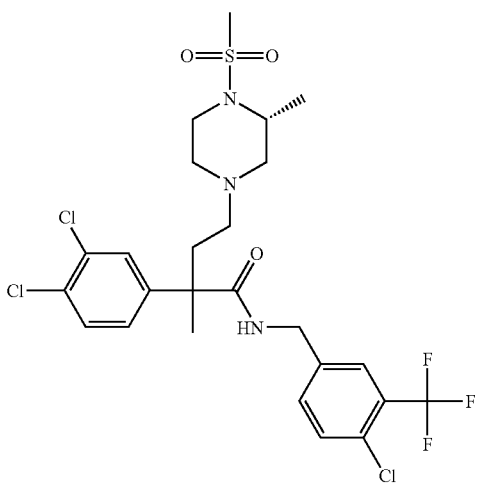 | N-(4-Chloro-3-trifluoromethyl-benzyl)-2-(3,4-dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 4-Chloro-3-trifluoromethyl-benzylamine (commercially available) | 614.3 |
| 55 | 594.5 | 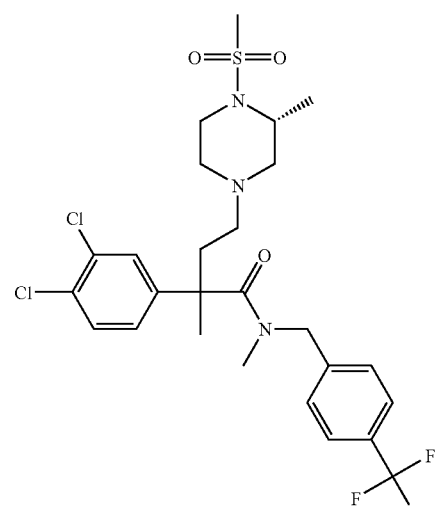 | 2-(3,4-Dichloro-phenyl)-4-((R)-4-methanesulfonyl-3-methyl-piperazin-1-yl)-2,N-dimethyl-N-(4-trifluoromethyl-benzyl)-butyramide | 2-(3,4-Dichloro-phenyl)-4-((R)-4-methanesulfonyl-3-methyl-piperazin-1-yl)-2-methyl-butyric acid (intermediate 3) and Methyl-(4-trifluoromethyl-benzyl)-amine (commercially available) | 594.2 |

TABLE 2-continued

| No | MW | structure | Systematic Name | starting materials | MW found MH+ |
|---|---|---|---|---|---|
| 56 | 561.0 | 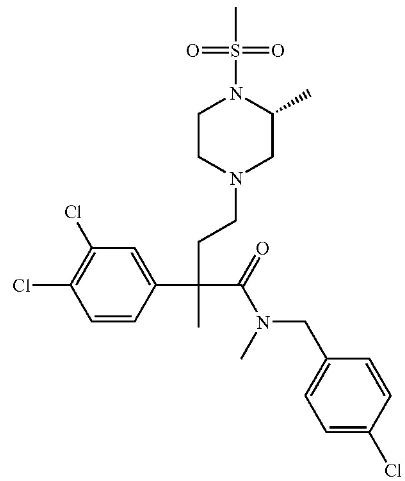 | N-(4-Chloro-benzyl)-2-(3,4-Dichloro-phenyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (4-Chloro-benzyl)-methyl-amine (commercially available) | 560.3 |
| 57 | 537.5 | 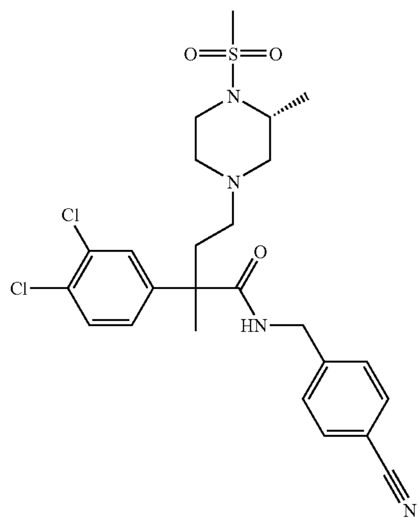 | N-(4-Cyano-benzyl)-2-(3,4-Dichloro-phenyl)-4-((R)-4-methanesulfonyl-3-methyl-piperazin-1-yl)-2-methyl-butyramide | 2-(3,4-Dichloro-phenyl)-4-((R)-4-methanesulfonyl-3-methyl-piperazin-1-yl)-2-methyl-butyric acid (intermediate 3) and 4-Aminomethyl-benzonitrile (commercially available) | 537.3 |
| 58 | 594.5 | 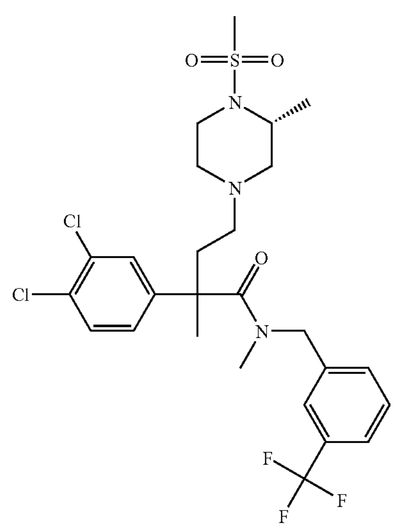 | 2-(3,4-Dichloro-phenyl)-4-((R)-4-methanesulfonyl-3-methyl-piperazin-1-yl)-2,N-dimethyl-N-(3-trifluoromethyl-benzyl)-butyramide | 2-(3,4-Dichloro-phenyl)-4-((R)-4-methanesulfonyl-3-methyl-piperazin-1-yl)-2-methyl-butyric acid (intermediate 3) and Methyl-(3-trifluoromethyl-benzyl)-amine (commercially available) | 594.2 |

TABLE 2-continued

| No | MW | structure | Systematic Name | starting materials | MW found MH+ |
|---|---|---|---|---|---|
| 59 | 561.0 | 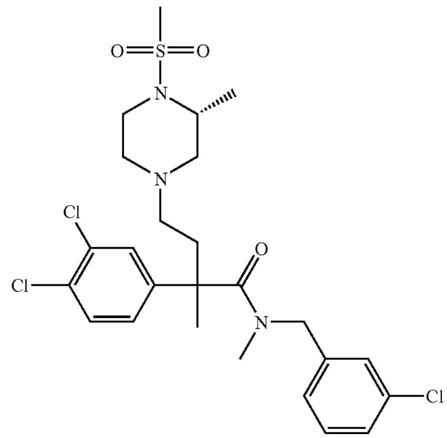 | N-(3-Chloro-benzyl)-2-(3,4-dichloro-phenyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (3-Chloro-benzyl)-methyl-amine (commercially available) | 562.5 |
| 60 | 544.5 | 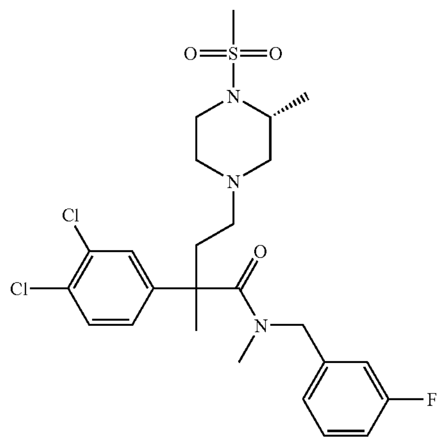 | 2-(3,4-Dichloro-phenyl)-N-(3-fluoro-benzyl)-4-((R)-4-methanesulfonyl-3-methyl-piperazin-1-yl)-2,N-dimethyl-butyramide | 2-(3,4-Dichloro-phenyl)-4-((R)-4-methanesulfonyl-3-methyl-piperazin-1-yl)-2-methyl-butyric acid (intermediate 3) and (3-Fluoro-benzyl)-methyl-amine (commercially available) | 544.2 |
| 61 | 603.6 | 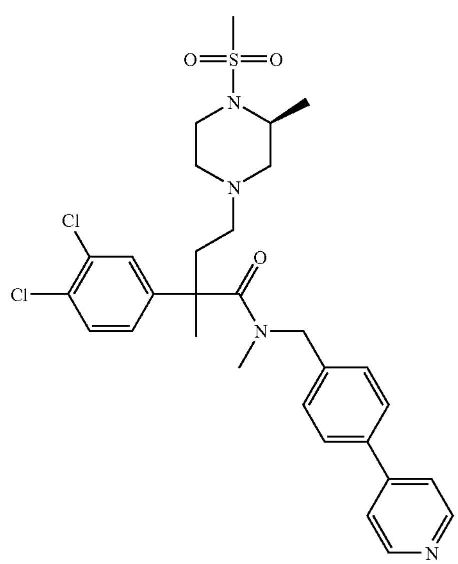 | 2-(3,4-Dichloro-phenyl)-4-((S)-4-methanesulfonyl-3-methyl-piperazin-1-yl)-2,N-dimethyl-N-(4-pyridin-4-yl-benzyl)-butyramide | 2-(3,4-Dichloro-phenyl)-4-((S)-4-methanesulfonyl-3-methyl-piperazin-1-yl)-2-methyl-butyric acid (intermediate 4) and Methyl-(4-pyridin-4-yl-benzyl)-amine (commercially available) | 603.3 |

TABLE 2-continued

| No | MW | structure | Systematic Name | starting materials | MW found MH+ |
|---|---|---|---|---|---|
| 62 | 574.5 | 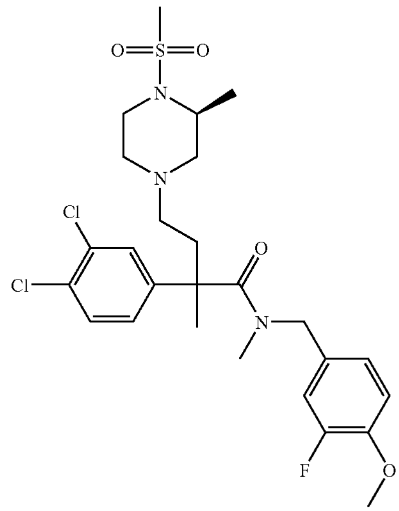 | 2-(3,4-Dichloro-phenyl)-N-(3-fluoro-4-methoxy-benzyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3-Fluoro-4-methoxy-benzyl)-methyl-amine (commercially available) | 574.3 |
| 63 | 582.6 | 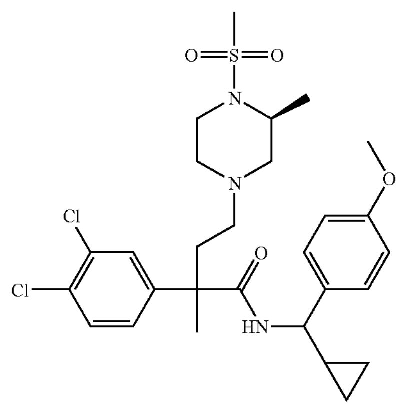 | N-[Cyclopropyl-(4-methoxy-phenyl)-methyl]-2-(3,4-dichloro-phenyl)-4-((S)-4-methanesulfonly-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and C-Cyclopropyl-C-(4-methoxy-phenyl)-methylamine (commercially available) | 584.2 |
| 64 | 612.5 | 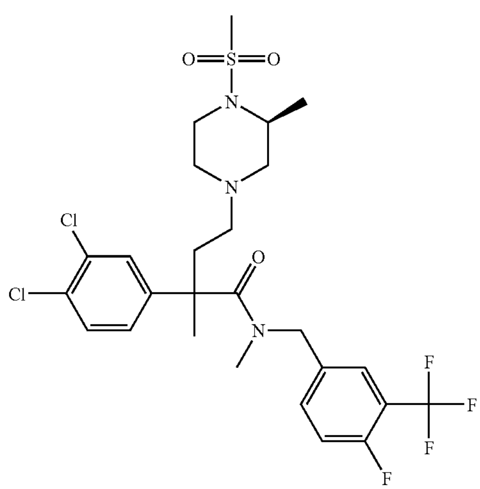 | 2-(3,4-Dichloro-phenyl)-N-(4-fluoro-3-trifluoromethyl-benzyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (4-Fluoro-3-trifluoromethyl-benzyl)-methyl-amine (commercially acid available) | 612.3 |

TABLE 2-continued

| No | MW | structure | Systematic Name | starting materials | MW found MH+ |
|---|---|---|---|---|---|
| 65 | 648.5 | 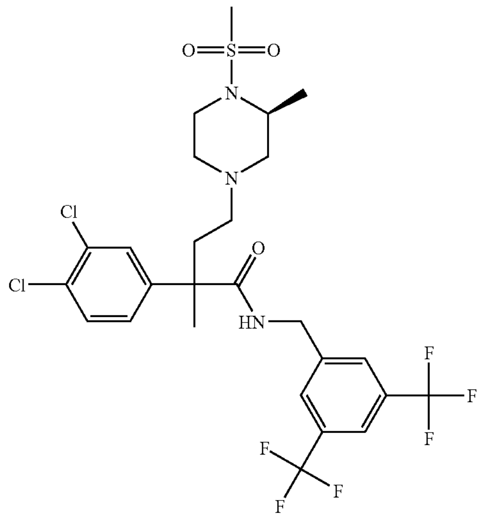 | N-(3,5-Bis-trifluoromethyl-benzyl)-2-(3,4-dichloro-phenyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 3,5-Bis-trifluoromethyl-benzylamine (commercially available) | 648.2 |
| 66 | 622.6 | 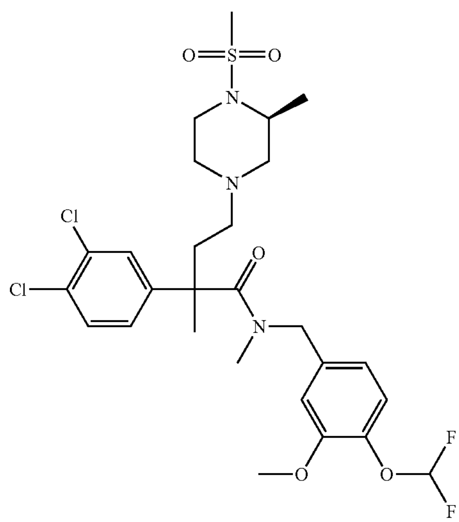 | 2-(3,4-Dichloro-phenyl)-N-(4-difluoromethoxy-3-methoxy-benzyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 3) and (4-Difluoromethoxy-3-methoxy-benzyl)-methyl-amine (commercially available) | 622.3 |
| 67 | 540.6 | 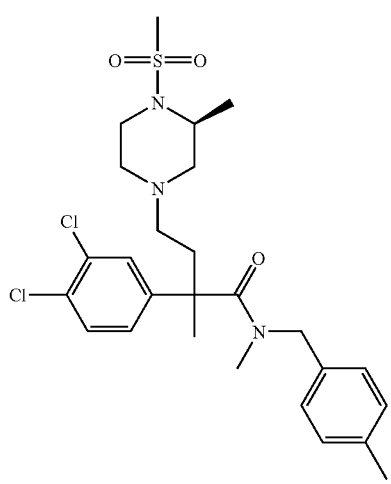 | 2-(3,4-Dichloro-phenyl)-4-((S)-4-methanesulfonyl-3-methyl-piperazin-1-yl)-2,N-dimethyl-N-(4-methyl-benzyl)-butyramide | 2-(3,4-Dichloro-phenyl)-4-((S)-4-methanesulfonyl-3-methyl-piperazin-1-yl)-2-methyl-butyric acid (intermediate 4) and Methyl-(4-methyl-benzyl)-amine (commercially available) | 540.4 |

TABLE 2-continued

| No | MW | structure | Systematic Name | starting materials | MW found MH+ |
|---|---|---|---|---|---|
| 68 | 555.6 | 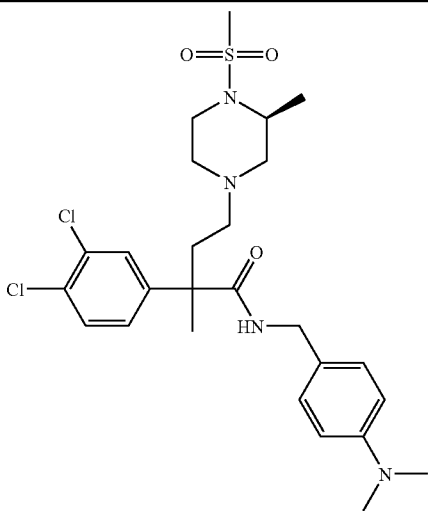 | 2-(3,4-Dichloro-phenyl)-N-(4-dimethylamino-benzyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and (4-Aminomethyl-phenyl)-dimethyl-amine (commercially available) | 555.2 |
| 69 | 629.0 | 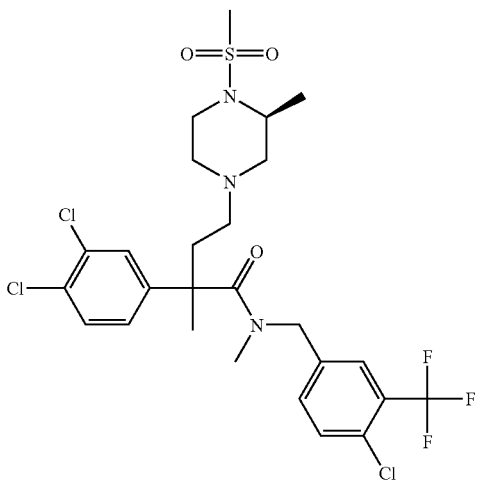 | N-(4-Chloro-3-trifluoromethyl-benzyl)-2-(3,4-dichloro-phenyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (4-Chloro-3-trifluoromethyl-benzyl)-methyl-amine (commercially available) | 630.3 |
| 70 | 612.5 | 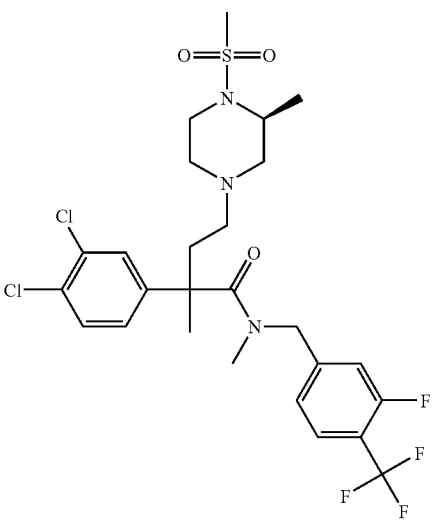 | 2-(3,4-Dichloro-phenyl)-N-(3-fluoro-4-trifluoromethyl-benzyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3-Fluoro-4-trifluoromethyl-benzyl)-methyl-amine (commercially available) | 612.1 |

TABLE 2-continued

| No | MW | structure | Systematic Name | starting materials | MW found MH+ |
|---|---|---|---|---|---|
| 71 | 595.4 | 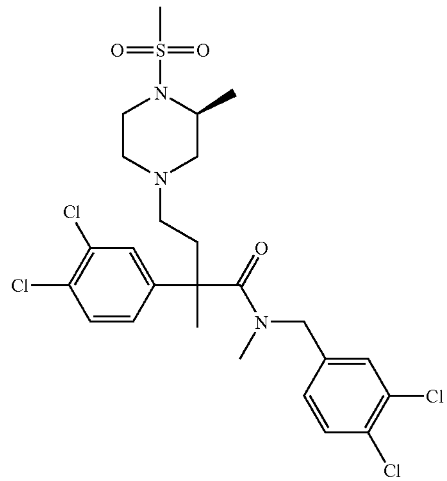 | N-(3,4-Dichloro-benzyl)-2-(3,4-dichloro-phenyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3,4-Dichloro-benzyl)-methyl-amine (commercially available) | 596.2 |
| 72 | 581.4 | 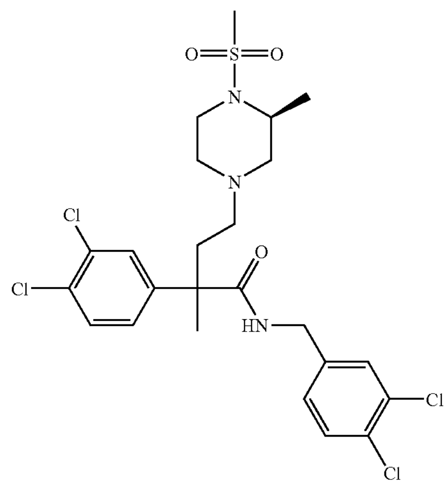 | N-(3,4-Dichloro-benzyl)-2-(3,4-dichloro-phenyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 3,4-Dichloro-benzylamine (commercially available) | 582 |
| 73 | 578.5 | 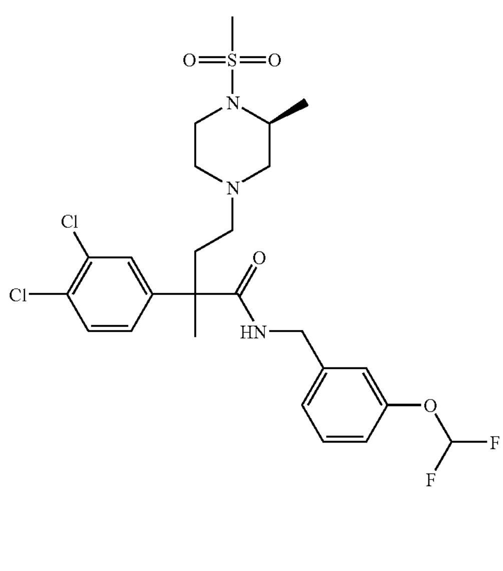 | 2-(3,4-Dichloro-phenyl)-N-(3-difluoromethoxy-benzyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 3-Difluoromethoxy-benzylamine (commercially available) | 578.1 |

TABLE 2-continued

| No | MW | structure | Systematic Name | starting materials | MW found MH+ |
|---|---|---|---|---|---|
| 74 | 598.5 | 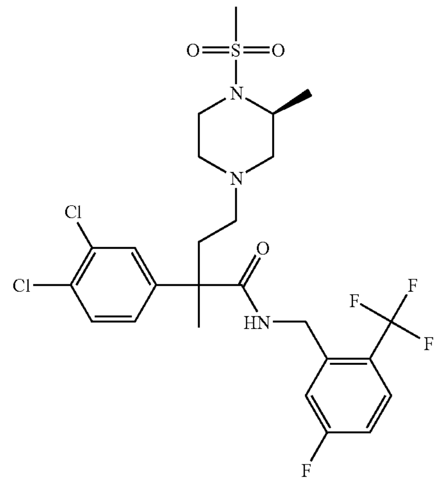 | 2-(3,4-Dichloro-phenyl)-N-(5-fluoro-2-trifluoromethyl-benzyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 5-Fluoro-2-trifluoromethyl-benzylamine (commercially available) | 598.3 |
| 75 | 580.5 | 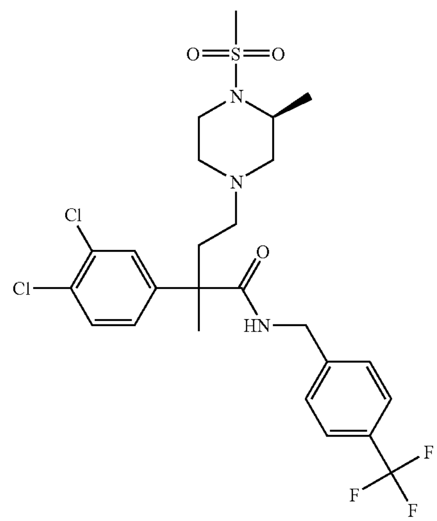 | 2-(3,4-Dichloro-phenyl)-4-((S)-4-methanesulfonyl-3-methyl-piperazin-1-yl)-2-methyl-N-(4-trifluoromethyl-benzyl)-butyramide | 2-(3,4-Dichloro-phenyl)-4-((S)-4-methanesulfonyl-3-methyl-piperazin-1-yl)-2-methyl-butyric acid (intermediate 4) and 4-Trifluoromethyl-benzylamine (commercially available) | 580 |
| 76 | 598.5 | 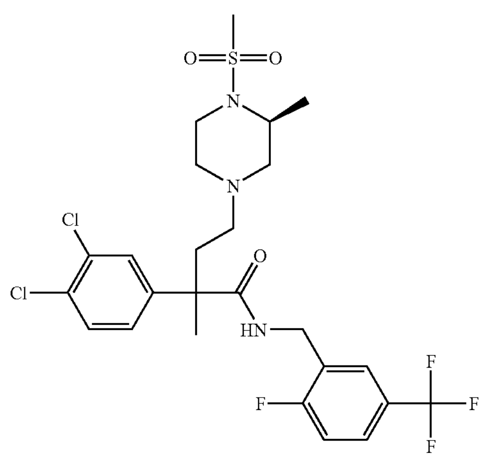 | 2-(3,4-Dichloro-phenyl)-N-(2-fluoro-5-trifluoromethyl-benzyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 2-Fluoro-5-trifluoromethyl-benzylamine (commercially available) | 598.1 |

TABLE 2-continued

| No | MW | structure | Systematic Name | starting materials | MW found MH+ |
|----|------|-----------|-----------------|--------------------|--------|
| 77 | 561.0 | 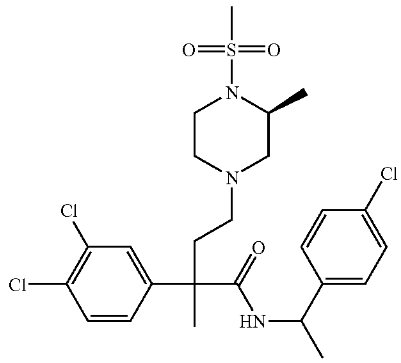 | N-[1-(4-Chloro-phenyl)-ethyl]-2-(3,4-dichloro-phenyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 1-(4-Chloro-phenyl)-ethylamine (commercially available) | 560.3 |
| 78 | 556.6 | 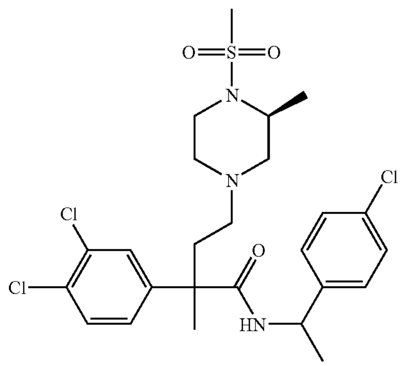 | 2-(3,4-Dichloro-phenyl)-4-((S)-4-methanesulfonyl-3-methyl-piperazin-1-yl)-N-(3-methoxy-benzyl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3-Methoxy-benzyl)-methyl-amine (commercially available) | 556.1 |
| 79 | 561.0 | 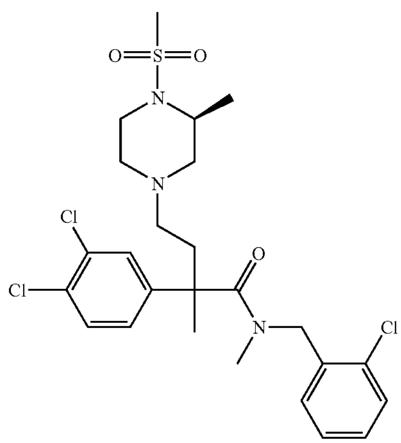 | N-(2-Chloro-benzyl)-2-(3,4-dichloro-phenyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (2-Chloro-benzyl)-methyl-amine (commercially available) | 562.3 |
| 80 | 595.4 | 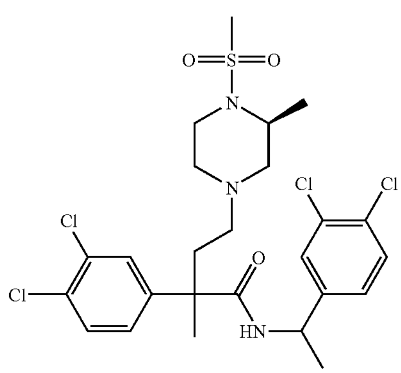 | 2-(3,4-Dichloro-phenyl)-N-[1-(3,4-dichloro-phenyl)-ethyl]-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 1-(3,4-Dichloro-phenyl)-ethylamine (commercially available) | 596.2 |

TABLE 2-continued

| No | MW | structure | Systematic Name | starting materials | MW found MH+ |
|---|---|---|---|---|---|
| 81 | 596.5 | 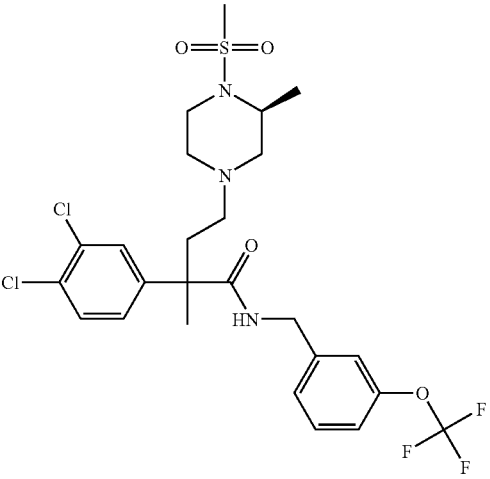 | 2-(3,4-Dichloro-phenyl)-4-((S)-4-methanesulfonyl-3-methyl-piperazin-1-yl)-2-methyl-N-(3-trifluoromethoxy-benzyl)-butyramide | 2-(3,4-Dichloro-phenyl)-4-((S)-4-methanesulfonyl-3-methyl-piperazin-1-yl)-2-methyl-butyric acid (intermediate 4) and 3-Trifluoromethoxy-benzylamine (commercially available) | 596.3 |
| 82 | 564.9 | 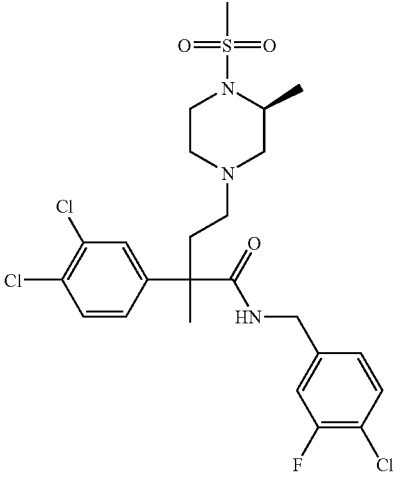 | N-(4-Chloro-3-fluoro-benzyl)-2-(3,4-dichloro-phenyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 3-Chloro-4-fluoro-benzylamine (commercially available) | 566.3 |
| 83 | 596.5 | 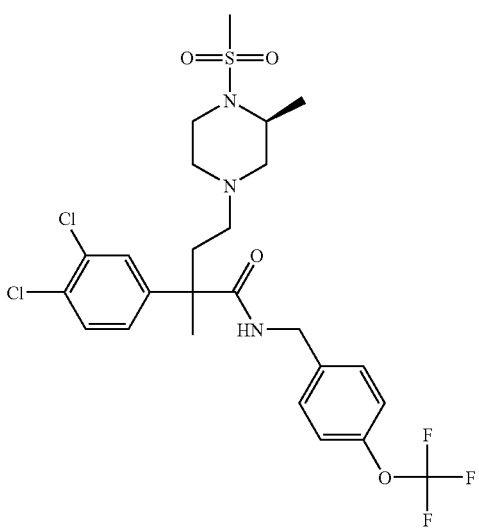 | 2-(3,4-Dichloro-phenyl)-4-((S)-4-methanesulfonyl-3-methyl-piperazin-1-yl)-2-methyl-N-(4-trifluoromethoxy-benzyl)-butyramide | 2-(3,4-Dichloro-phenyl)-4-((S)-4-methanesulfonyl-3-methyl-piperazin-1-yl)-2-methyl-butyric acid (intermediate 4) and 4-Trifluoromethoxy-benzylamine (commercially available) | 596.2 |

TABLE 2-continued

| No | MW | structure | Systematic Name | starting materials | MW found MH+ |
|---|---|---|---|---|---|
| 84 | 614.9 | 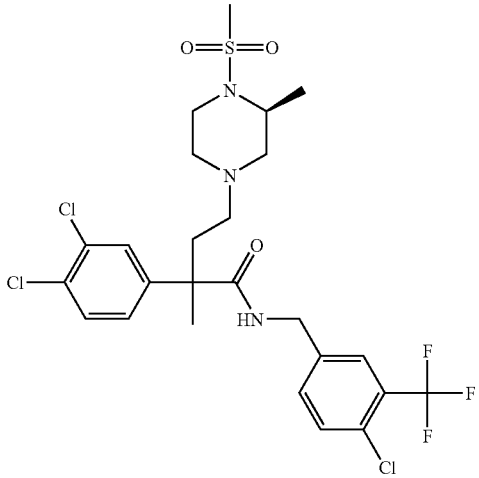 | N-(4-Chloro-3-trifluoromethyl-benzyl)-2-(3,4-dichloro-phenyl)-4-((S)-4-methanesulfonyl-3-methyl-piperazin-1-yl)-2-methyl-butyramide | 2-(3,4-Dichloro-phenyl)-4-((S)-4-methanesulfonyl-3-methyl-piperazin-1-yl)-2-methyl-butyric acid (intermediate 4) and 4-Chloro-3-trifluoromethyl-benzylamine (commercially available) | 614.3 |
| 85 | 594.5 | 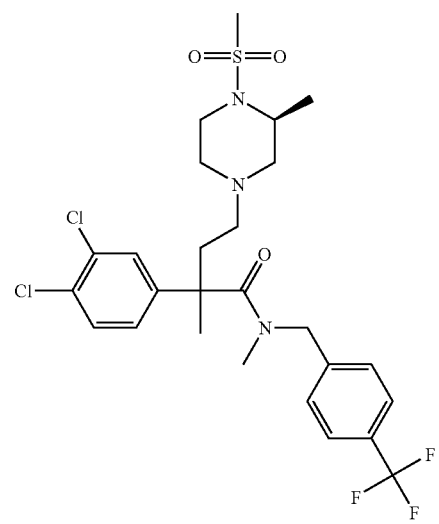 | 2-(3,4-Dichloro-phenyl)-4-((S)-4-methanesulfonyl-3-methyl-piperazin-1-yl)-2,N-dimethyl-N-(4-trifluoromethyl-benzyl)-butyramide | 2-(3,4-Dichloro-phenyl)-4-((S)-4-methanesulfonyl-3-methyl-piperazin-1-yl)-2-methyl-butyric acid (intermediate 4) and Methyl-(4-trifluoromethyl-benzyl)-amine (commercially available) | 594.2 |
| 86 | 561.0 | 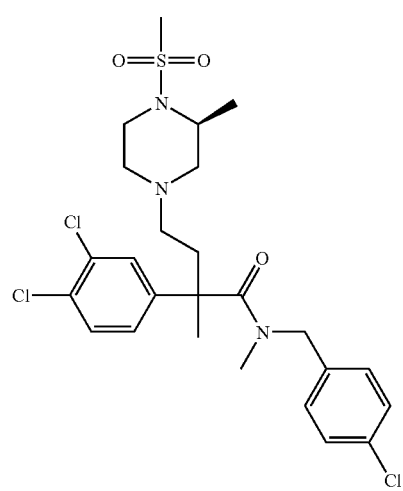 | N-(4-Chloro-benzyl)-2-(3,4-Dichloro-phenyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (4-Chloro-benzyl)-methyl-amine (commercially available) | 562.5 |

TABLE 2-continued

| No | MW | structure | Systematic Name | starting materials | MW found MH+ |
|---|---|---|---|---|---|
| 87 | 594.5 | 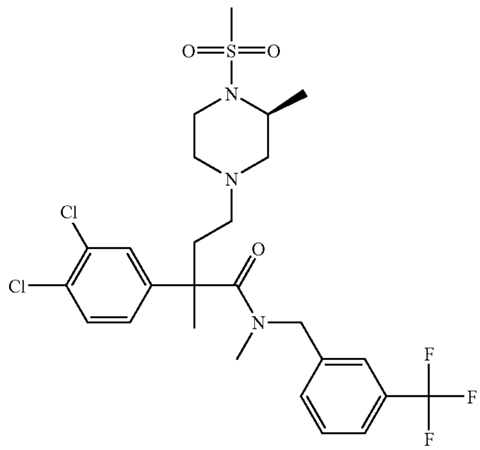 | 2-(3,4-Dichloro-phenyl)-4-((S)-4-methanesulfonyl-3-methyl-piperazin-1-yl)-2,N-dimethyl-N-(3-trifluoromethyl-benzyl)-butyramide | 2-(3,4-Dichloro-phenyl)-4-((S)-4-methanesulfonyl-3-methyl-piperazin-1-yl)-2-methyl-butyric acid (intermediate 4) and Methyl-(3-trifluoromethyl-benzyl)-amine (commercially available) | 594.3 |
| 88 | 561.0 | 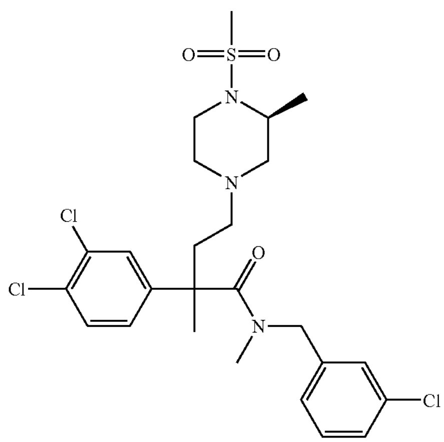 | N-(3-Chloro-benzyl)-2-(3,4-dichloro-phenyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3-Chloro-benzyl)-methyl-amine (commercially available) | 560.3 |
| 89 | 544.5 | 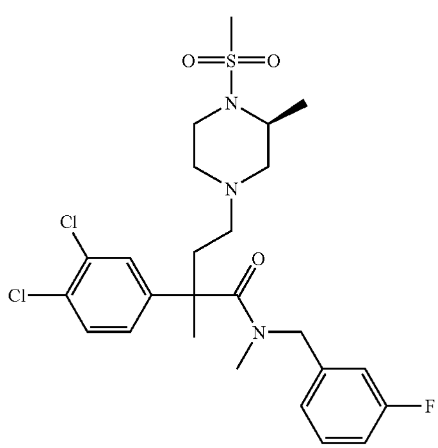 | 2-(3,4-Dichloro-phenyl)-N-(3-fluoro-benzyl)-4-((S)-4-methanesulfonyl-3-methyl-piperazin-1-yl)-2,N-dimethyl-butyramide | 2-(3,4-Dichloro-phenyl)-4-((S)-4-methanesulfonyl-3-methyl-piperazin-1-yl)-2-methyl-butyric acid (intermediate 4) and (3-Fluoro-benzyl)-methyl-amine (commercially available) | 544.2 |

TABLE 2-continued

| No | MW | structure | Systematic Name | starting materials | MW found MH+ |
|---|---|---|---|---|---|
| 90 | 595.5 | 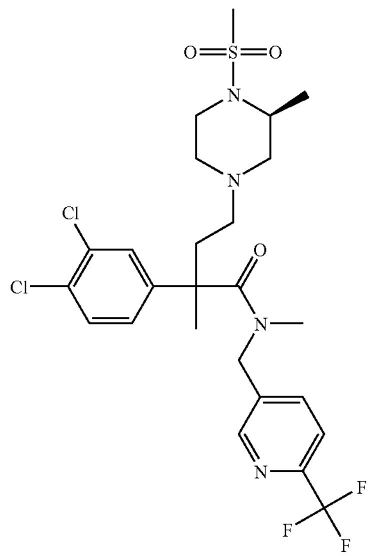 | 2-(3,4-Dichloro-phenyl)-4-((S)-4-methanesulfonyl-3-methyl-piperazin-1-yl)-2,N-dimethyl-N-(6-trifluoromethyl-pyridin-3-ylmethyl)-butyramide | 2-(3,4-Dichloro-phenyl)-4-((S)-4-methanesulfonyl-3-methyl-piperazin-1-yl)-2-methyl-butyric acid (intermediate 4) and C-(6-Trifluoromethyl-pyridin-3-yl)-methylamine (commercially available) | 595.2 |
| 91 | 581.5 | 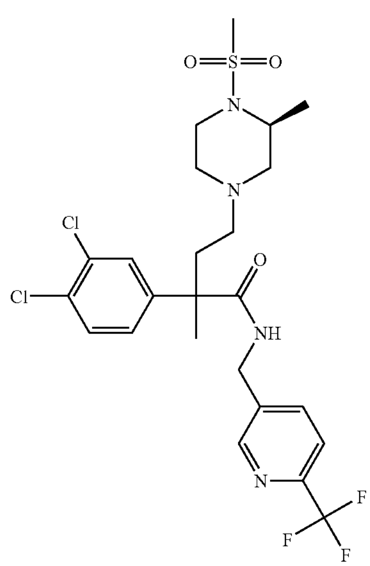 | 2-(3,4-Dichloro-phenyl)-4-((S)-4-methanesulfonyl-3-methyl-piperazin-1-yl)-2-methyl-N-(6-trifluoromethyl-pyridin-3-ylmethyl)-butyramide | 2-(3,4-Dichloro-phenyl)-4-((S)-4-methanesulfonyl-3-methyl-piperazin-1-yl)-2-methyl-butyric acid (intermediate 4) and C-(6-Trifluoromethyl-pyridin-3-yl)-methylamine (commercially available) | 581 |

TABLE 2-continued

| No | MW | structure | Systematic Name | starting materials | MW found MH+ |
|---|---|---|---|---|---|
| 92 | 581.5 | 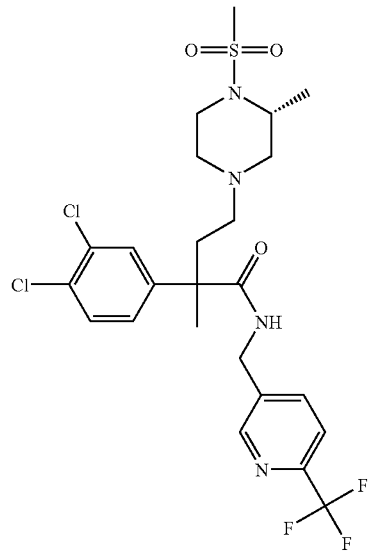 | 2-(3,4-Dichloro-phenyl)-4-((R)-4-methanesulfonyl-3-methyl-piperazin-1-yl)-2-methyl-N-(6-trifluoromethyl-pyridin-3-ylmethyl)-butyramide | 2-(3,4-Dichloro-phenyl)-4-((R)-4-methanesulfonyl-3-methyl-piperazin-1-yl)-2-methyl-butyric acid (intermediate 3) and (commercially available) | 581 |

EXAMPLE 93

(S or R)—N-(3,4-Dichloro-benzyl)-2-(3,4-dichloro-phenyl)-4-((R)-4-methanesulfonyl-3-methyl-piperazin-1-yl)-2-methyl-butyramide MS(m/e): 581.4 (MH+) (or diastereoisomer)

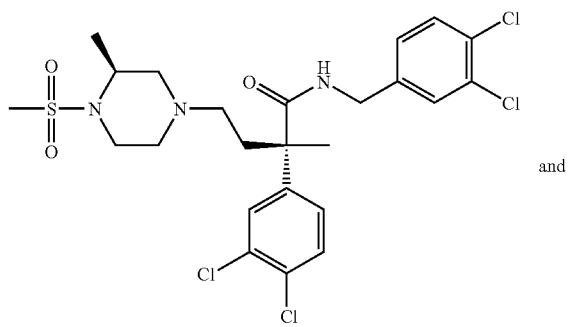

and

EXAMPLE 94

(R or S)—N-(3,4-Dichloro-benzyl)-2-(3,4-dichloro-phenyl)-4-((R)-4-methanesulfonyl-3-methyl-piperazin-1-yl)-2-methyl-butyramide MS(m/e): 581.5 (MH+) (or diastereoisomer)

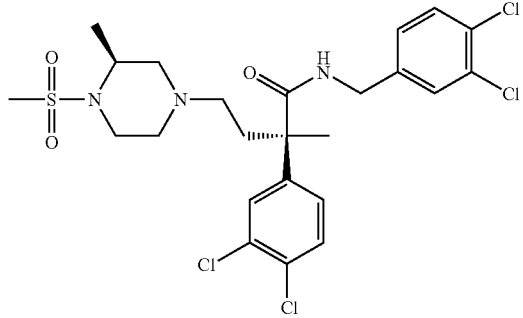

The title compounds were isolated from N-(3,4-dichloro-benzyl)-2-(3,4-dichloro-phenyl)-4-((R)-4-methanesulfonyl-3-methyl-piperazin-1-yl)-2-methyl-butyramide (example 42) through column chromatography on chiral phase.

In analogy to the procedure described for the synthesis of N-(4-chloro-benzyl)-2-(3,4-dichloro-phenyl)-4-(4-methane-sulfonyl-piperazin-1-yl)-N-methyl-butyramide (example 1) further (homo)-piperazine derivatives have been synthesized from the starting materials listed in Table 3. Table 3 comprises examples 95-137.

TABLE 3

| No | MW | structure | Systematic Name | starting materials | MW found MH+ |
|---|---|---|---|---|---|
| 95 | 598.5 | 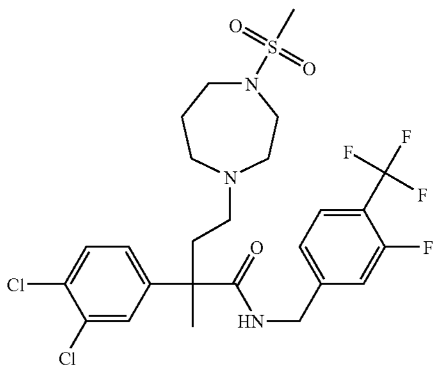 | 2-(3,4-Dichloro-phenyl)-N-(3-fluoro-4-trifluoromethyl-benzyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 3-Fluoro-4-trifluoromethyl-benzylamine (commercially available) | 598.3 |
| 96 | 594.5 | 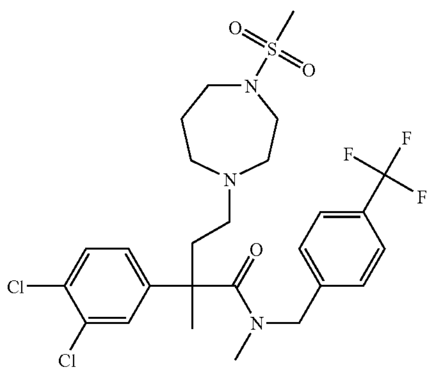 | 2-(3,4-Dichloro-phenyl)-4-(4-methanesulfonyl-[1,4]diazepan-1-yl)-2,N-dimethyl-N-(4-trifluoromethyl-benzyl)-butyramide | 2-(3,4-Dichloro-phenyl)-4-(4-methanesulfonyl-[1,4]diazepan-1-yl)-2-methyl-butyric acid (intermediate 5) and Methyl-(4-trifluoromethyl-benzyl)-amine (commercially available) | 594.3 |
| 97 | 561.0 | 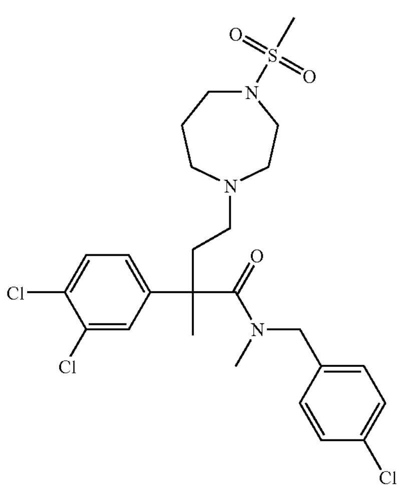 | N-(4-Chloro-benzyl)-2-(3,4-dichloro-phenyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (4-Chloro-benzyl)-methyl-amine(commercially available) | 562.2 |

| No | MW | structure | Systematic Name | starting materials | MW found MH+ |
|---|---|---|---|---|---|
| 98 | 564.9 | 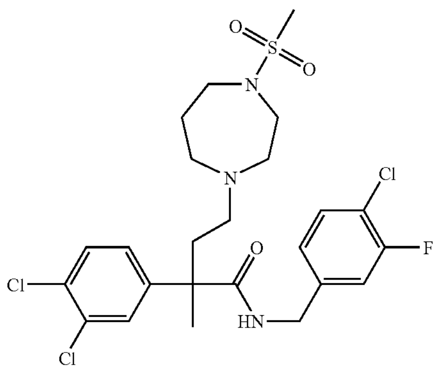 | N-(4-Chloro-3-fluoro-benzyl)-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 3-Chloro-4-fluoro-benzylamine (commercially available) | 566.3 |
| 99 | 596.5 | 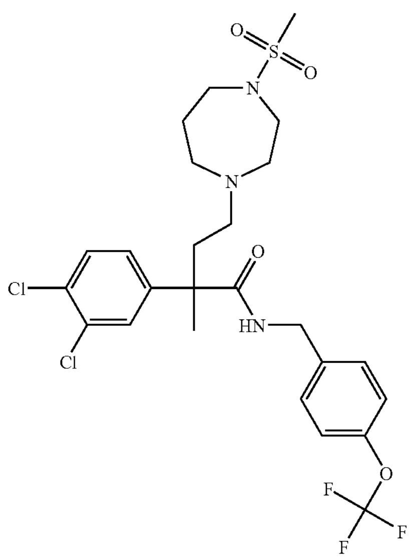 | 2-(3,4-Dichloro-phenyl)-4-(4-methanesulfonyl-[1,4]diazepan-1-yl)-2-methyl-N-(4-trifluoromethoxy-benzyl)-butyramide | 2-(3,4-Dichloro-phenyl)-4-(4-methanesulfonyl-[1,4]diazepan-1-yl)-2-methyl-butyric acid (intermediate 5) and 4-Trifluoromethoxy-benzylamine (commercially available) | 596.2 |
| 100 | 544.5 | 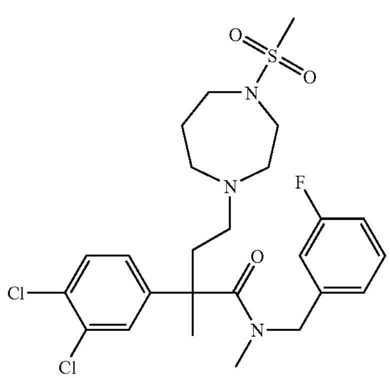 | 2-(3,4-Dichloro-phenyl)-N-(3-fluoro-benzyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3-Fluoro-benzyl)-methyl-amine (commercially available) | 544.3 |

TABLE 3-continued

| No | MW | structure | Systematic Name | starting materials | MW found MH+ |
|---|---|---|---|---|---|
| 101 | 594.5 | 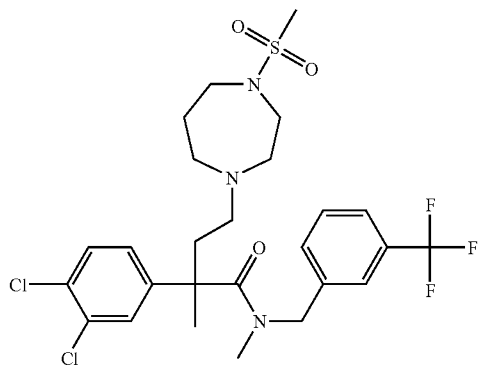 | 2-(3,4-Dichloro-phenyl)-4-(4-methanesulfonyl-[1,4]diazepan-1-yl)-2,N-dimethyl-N-(3-trifluoromethyl-benzyl)-butyramide | 2-(3,4-Dichloro-phenyl)-4-(4-methanesulfonyl-[1,4]diazepan-1-yl)-2-methyl-butyric acid (intermediate 5) and Methyl-(3-trifluoromethyl-benzyl)-amine (commercially available) | 594.3 |
| 102 | 596.5 | 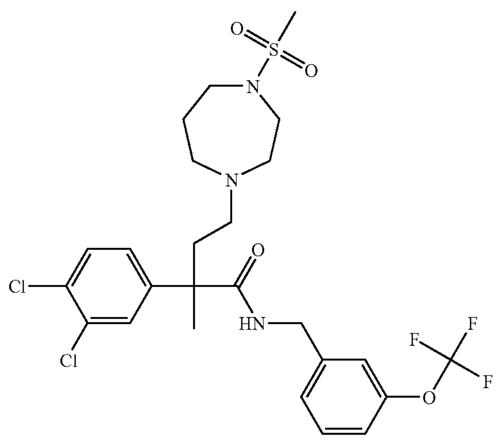 | 2-(3,4-Dichloro-phenyl)-4-(4-methanesulfonyl-[1,4]diazepan-1-yl)-2-methyl-N-(3-trifluoromethoxy-benzyl)-butyramide | 2-(3,4-Dichloro-phenyl)-4-(4-methanesulfonyl-[1,4]diazepan-1-yl)-2-methyl-butyric acid (intermediate 5) and 3-Trifluoromethoxy-benzylamine (commercially available) | 596.2 |
| 103 | 561.0 | 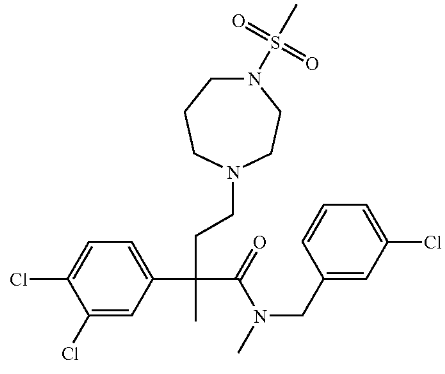 | N-(3-Chloro-benzyl)-2-(3,4-dichloro-phenyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3-Chloro-benzyl)-methyl-amine (commercially available) | 562.2 |

TABLE 3-continued

| No | MW | structure | Systematic Name | starting materials | MW found MH+ |
|---|---|---|---|---|---|
| 104 | 574.5 | 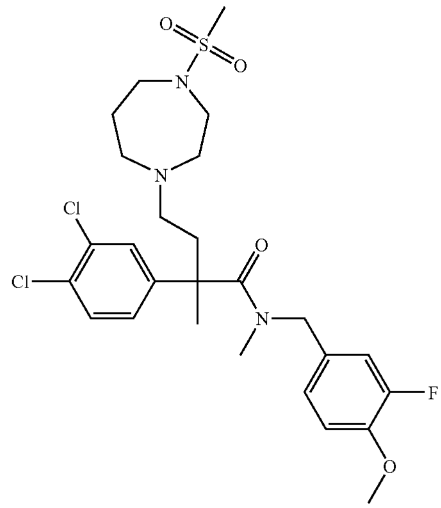 | 2-(3,4-Dichloro-phenyl)-N-(3-fluoro-4-methoxy-benzyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3-Fluoro-4-methoxy-benzyl)-methyl-amine (commercially available) | 574.3 |
| 105 | 582.6 | 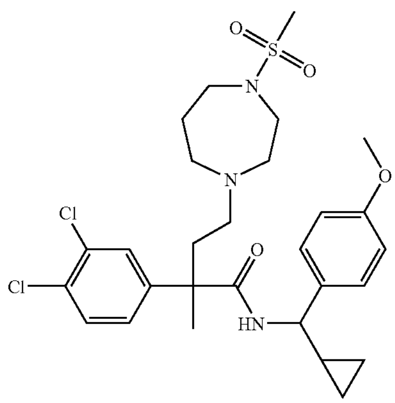 | N-[Cyclopropyl-(4-methoxy-phenyl)-methyl]-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and C-Cyclopropyl-C-(4-methoxy-phenyl)-methylamine (commercially available) | 584.1 |
| 106 | 612.5 | 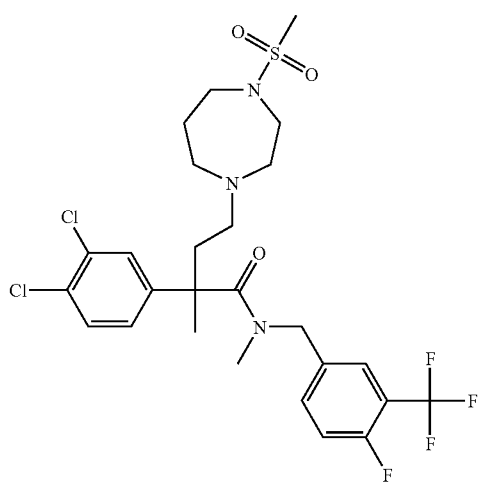 | 2-(3,4-Dichloro-phenyl)-N-(4-fluoro-3-trifluoromethyl-benzyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (4-Fluoro-3-trifluoromethyl-benzyl)-methyl-amine (commercially available) | 612.1 |

TABLE 3-continued

| No | MW | structure | Systematic Name | starting materials | MW found MH+ |
|---|---|---|---|---|---|
| 107 | 648.5 | 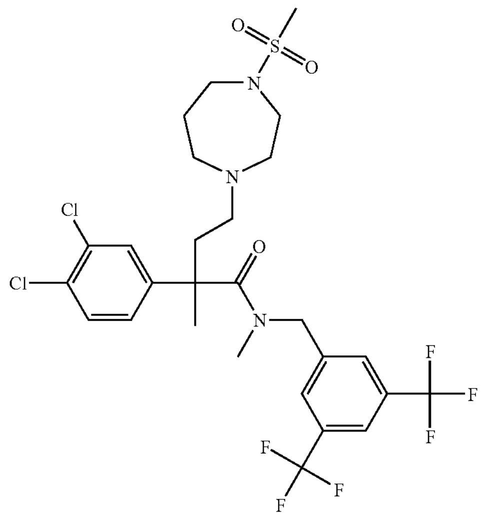 | N-(3,5-Bis-trifluoromethyl-benzyl)-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 3,5-Bis-trifluoromethyl-benzylamine (commercially available) | 648.2 |
| 108 | 622.6 | 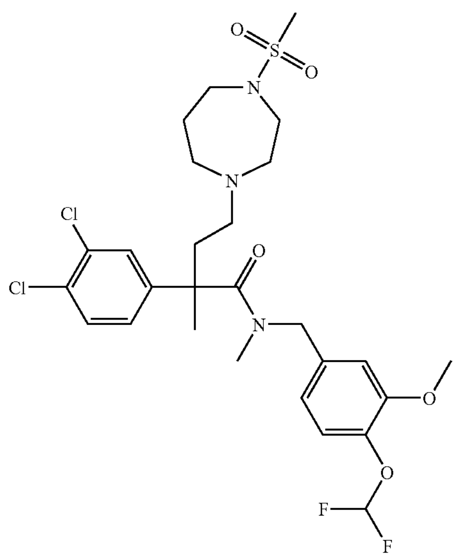 | 2-(3,4-Dichloro-phenyl)-N-(4-difluoromethoxy-3-methoxy-benzyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (4-Difluoromethoxy-3-methoxy-benzyl)-methyl-amine (commercially available) | 622.1 |
| 109 | 540.6 | 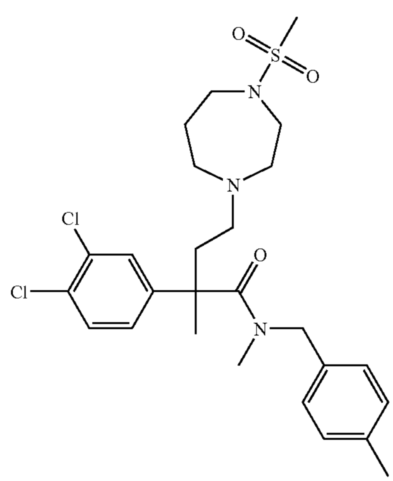 | 2-(3,4-Dichloro-phenyl)-4-(4-methanesulfonyl-[1,4]diazepan-1-yl)-2,N-dimethyl-N-(4-methyl-benzyl)-butyramide | 2-(3,4-Dichloro-phenyl)-4-(4-methanesulfonyl-[1,4]diazepan-1-yl)-2-methyl-butyric acid (intermediate 5) and Methyl-(4-methyl-benzyl)-amine (commercially available) | 540.3 |

TABLE 3-continued

| No | MW | structure | Systematic Name | starting materials | MW found MH+ |
|---|---|---|---|---|---|
| 110 | 555.6 | 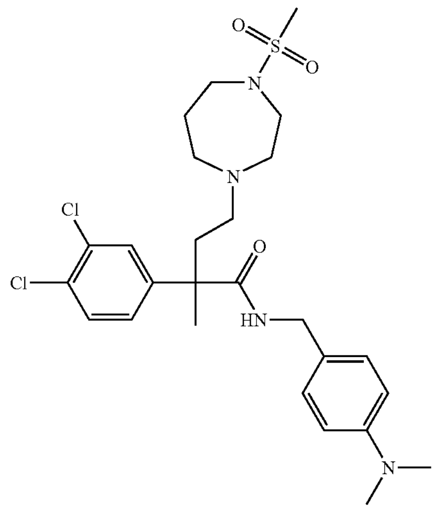 | 2-(3,4-Dichloro-phenyl)-N-(4-dimethylamino-benzyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and (4-Aminomethyl-phenyl)-dimethyl-amine (commercially available) | 555.3 |
| 111 | 629.0 | 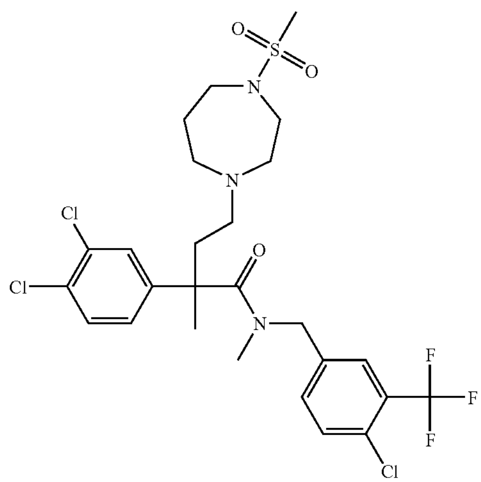 | N-(4-Chloro-3-trifluoromethyl-benzyl)-2-(3,4-dichloro-phenyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (4-Chloro-3-trifluoromethyl-benzyl)-methyl-amine (commercially available) | 630.2 |
| 112 | 612.5 | 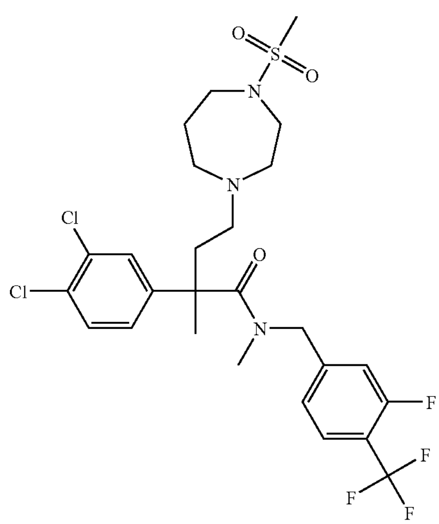 | 2-(3,4-Dichloro-phenyl)-N-(3-fluoro-4-trifluoromethyl-benzyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3-Fluoro-4-trifluoromethyl-benzyl)-methyl-amine (commercially available) | 612.3 |

TABLE 3-continued

| No | MW | structure | Systematic Name | starting materials | MW found MH+ |
|---|---|---|---|---|---|
| 113 | 595.4 | 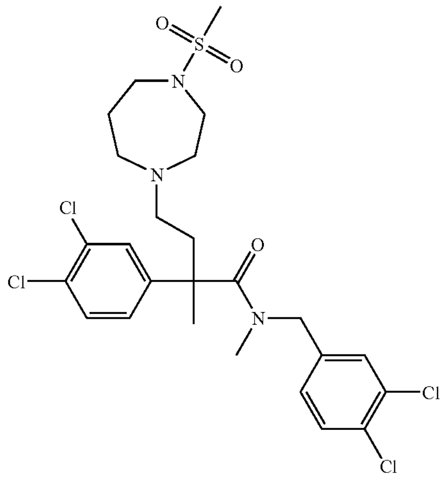 | N-(3,4-Dichloro-benzyl)-2-(3,4-dichloro-phenyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3,4-Dichloro-benzyl)-methyl-amine (commercially available) | 596.2 |
| 114 | 581.4 | 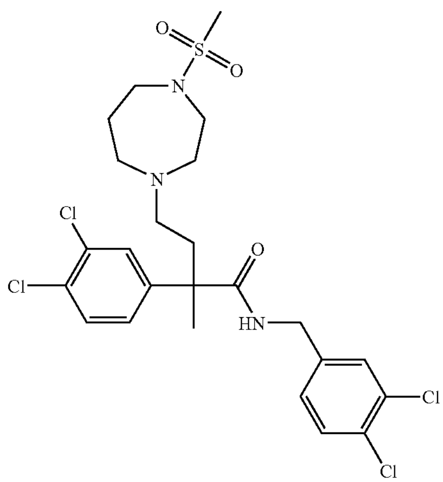 | N-(3,4-Dichloro-benzyl)-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 3,4-Dichloro-benzylamine (commercially available) | 582.2 |
| 115 | 578.5 | 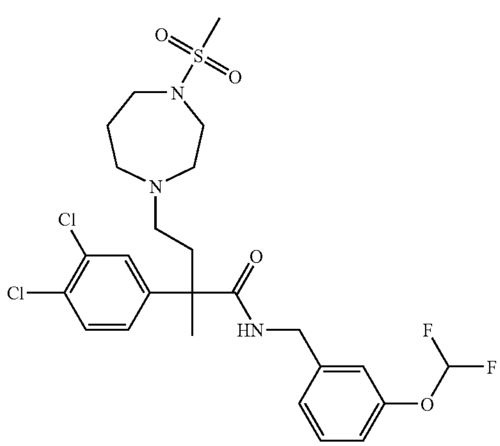 | 2-(3,4-Dichloro-phenyl)-N-(3-difluoromethoxy-benzyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 3-Difluoromethoxy-benzylamine (commercially available) | 578.5 |

TABLE 3-continued

| No | MW | structure | Systematic Name | starting materials | MW found MH+ |
|---|---|---|---|---|---|
| 116 | 598.5 | 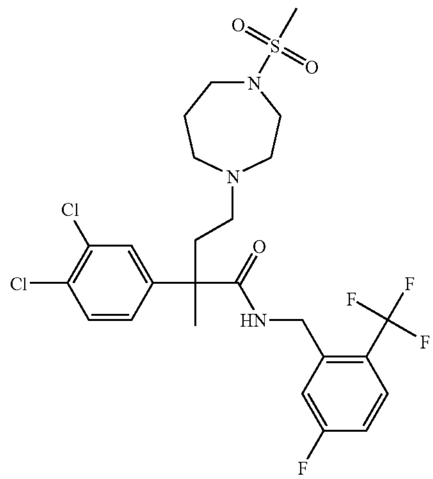 | 2-(3,4-Dichloro-phenyl)-N-(5-fluoro-2-trifluoromethyl-benzyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 5-Fluoro-2-trifluoromethyl-benzylamine (commercially available) | 598.1 |
| 117 | 580.5 | 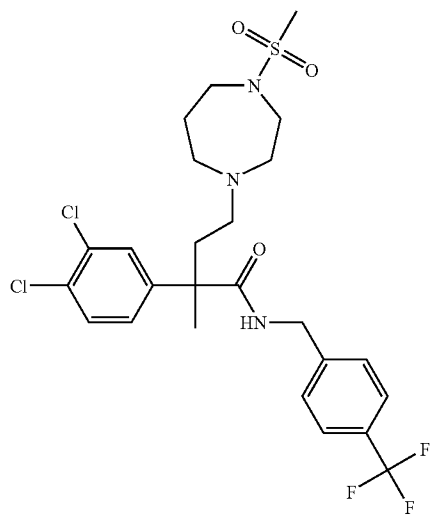 | 2-(3,4-Dichloro-phenyl)-4-(4-methanesulfonyl-[1,4]diazepan-1-yl)-2-methyl-N-(4-trifluoromethyl-benzyl)-butyramide | 2-(3,4-Dichloro-phenyl)-4-(4-methanesulfonyl-[1,4]diazepan-1-yl)-2-methyl-butyric acid (intermediate 5) and 4-Trifluoromethyl-benzylamine (commercially available) | 580.1 |
| 118 | 598.5 | 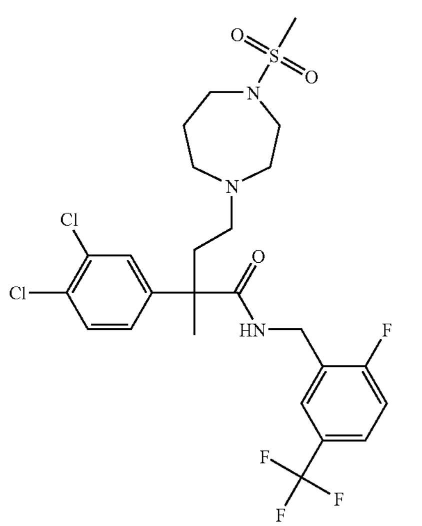 | 2-(3,4-Dichloro-phenyl)-N-(2-fluoro-5-trifluoromethyl-benzyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 2-Fluoro-5-trifluoromethyl-benzylamine (commercially available) | 598.3 |

TABLE 3-continued

| No | MW | structure | Systematic Name | starting materials | MW found MH+ |
|---|---|---|---|---|---|
| 119 | 561.0 | 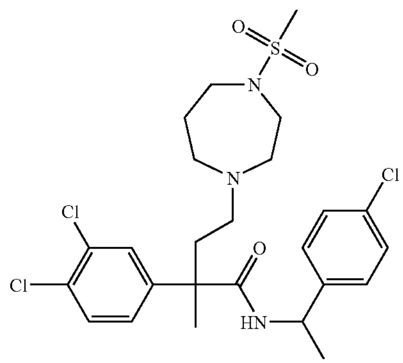 | N-[1-(4-Chloro-phenyl)-ethyl]-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 1-(4-Chloro-phenyl)-ethylamine (commercially available) | 560.3 |
| 120 | 556.6 | 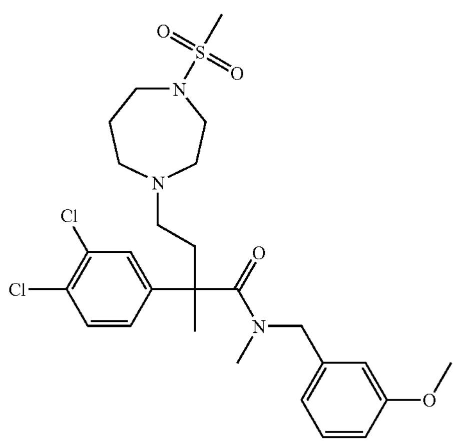 | 2-(3,4-Dichloro-phenyl)-4-(4-methanesulfonyl-[1,4]diazepan-1-yl)-N-(3-methoxy-benzyl)-2,N-dimethyl-butyramide | 2-(3,4-Dichloro-phenyl)-4-(4-methanesulfonyl-[1,4]diazepan-1-yl)-2-methyl-butyric acid (intermediate 5) and (3-Methoxy-benzyl)-methyl amine (commercially available) | 556.2 |
| 121 | 561.0 | 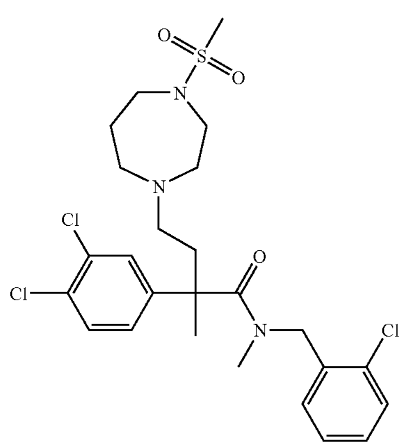 | N-(2-Chloro-benzyl)-2-(3,4-dichloro-phenyl)-4-(4-methanesulfonyl-[1,4]diazepan-1-yl)-2,N-dimethyl-butyramide | 2-(3,4-Dichloro-phenyl)-4-(4-methanesulfonyl-[1,4]diazepan-1-yl)-2-methyl-butyric acid (intermediate 5) and (2-Chloro-benzyl)-methyl-amine (commercially available) | 560.3 |

TABLE 3-continued

| No | MW | structure | Systematic Name | starting materials | MW found MH+ |
|---|---|---|---|---|---|
| 122 | 595.4 | 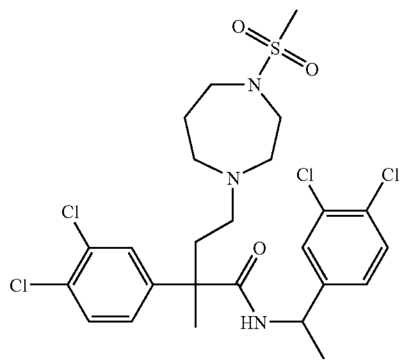 | 2-(3,4-Dichloro-phenyl)-N-[1-(3,4-dichloro-phenyl)-ethyl]-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 1-(3,4-Dichloro-phenyl)-ethylamine (commercially available) | 596.3 |
| 123 | 603.6 | 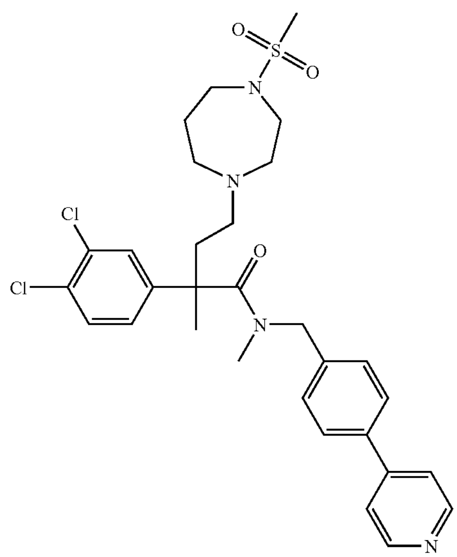 | 2-(3,4-Dichloro-phenyl)-4-(4-methanesulfonyl-[1,4]diazepan-1-yl)-2,N-dimethyl-N-(4-pyridin-4-yl-benzyl-butyramide | 2-(3,4-Dichloro-phenyl)-4-(4-methanesulfonyl-[1,4]diazepan-1-yl)-2-methyl-butyric acid (intermediate 5) and Methyl-(4-pyridin-4-yl-benzyl)-amine (commercially available) | 603.2 |
| 124 | 537.5 | 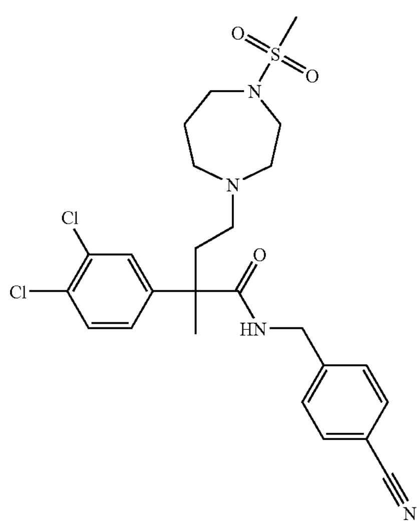 | N-(4-Cyano-benzyl)-2-(3,4-dichloro-phenyl)-4-(4-methanesulfonyl-[1,4]diazepan-1-yl)-2-methyl-butyramide | 2-(3,4-Dichloro-phenyl)-4-(4-methanesulfonyl-[1,4]diazepan-1-yl)-2-methyl-butyric acid (intermediate 5) and 4-Aminomethyl-benzonitrile (commercially available) | 537.3 |

TABLE 3-continued

| No | MW | structure | Systematic Name | starting materials | MW found MH+ |
|---|---|---|---|---|---|
| 125 | 595.5 | 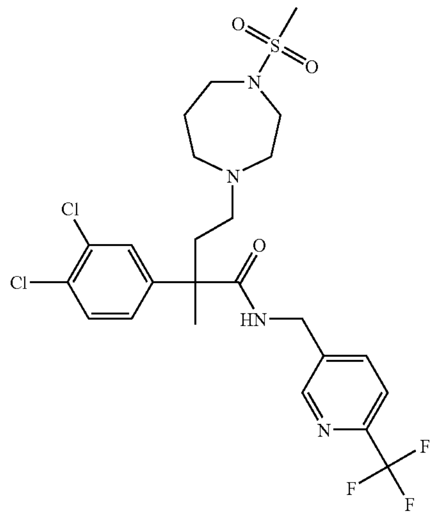 | 2-(3,4-Dichloro-phenyl)-4-(4-methanesulfonyl-[1,4]diazepan-1-yl)-2,N-dimethyl-N-(6-trifluoromethyl-pyridin-3-ylmethyl)-butyramide | 2-(3,4-Dichloro-phenyl)-4-(4-methanesulfonyl-[1,4]diazepan-1-yl)-2-methyl-butyric acid (intermediate 5) and C-(6-Trifluoromethyl-pyridin-3-yl)-methylamine (commercially available) | 595.3 |
| 126 | 581.5 | 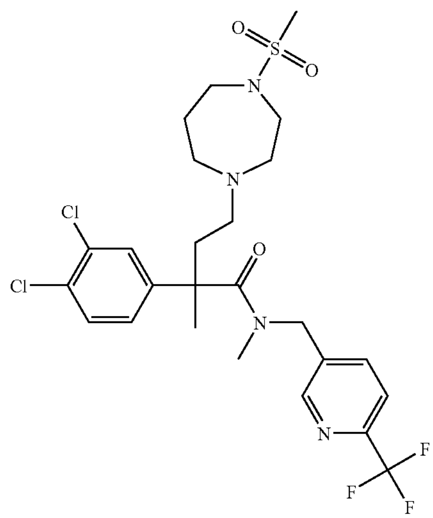 | 2-(3,4-Dichloro-phenyl)-4-(4-methanesulfonyl-[1,4]diazepan-1-yl)-2-methyl-N-(6-trifluoromethyl-pyridin-3-ylmethyl)-butyramide | 2-(3,4-Dichloro-phenyl)-4-(4-methanesulfonyl-[1,4]diazepan-1-yl)-2-methyl-butyric acid (intermediate 5) and C-(6-Trifluoromethyl-pyridin-3-yl)-methylamine (commercially available) | 581 |
| 127 | 580.5 | 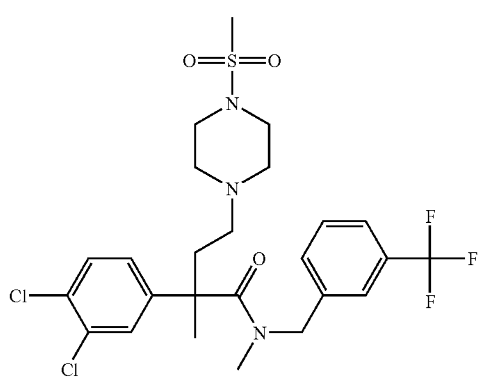 | 2-(3,4-Dichloro-phenyl)-4-(4-methanesulfonyl-piperazin-1-yl)-2,N-dimethyl-N-(3-trifluoromethyl-benzyl)-butyramide | 2-(3,4-Dichloro-phenyl)-4-(4-methanesulfonyl-piperazin-1-yl)-2-methyl-butyric acid (intermediate 2) and Methyl-(3-trifluoromethyl-benzyl)-amine (commercially available) | 580.2 |

| No | MW | structure | Systematic Name | starting materials | MW found MH+ |
|---|---|---|---|---|---|
| 128 | 528.5 | 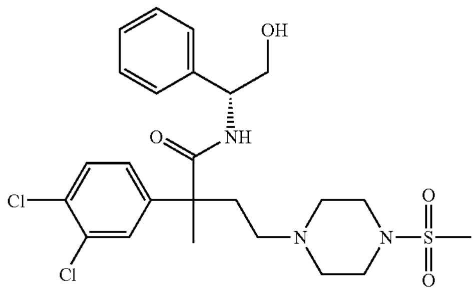 | (R or S)-2-(3,4-Dichloro-phenyl)-N-((R)-2-hydroxy-1-phenyl-ethyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (R)-2-Amino-2-phenyl-ethanol (commercially available) | 528.3 |
| 129 | 528.5 | 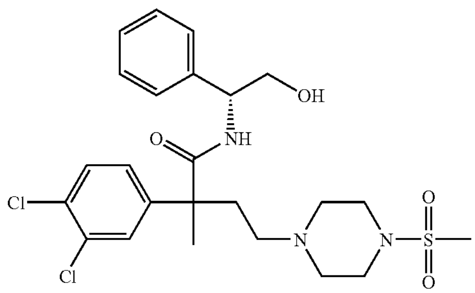 | (S or R)-2-(3,4-Dichloro-phenyl)-N-((R)-2-hydroxy-1-phenyl-ethyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (R)-2-Amino-2-phenyl-ethanol (commercially available) | 528.3 |
| 130 | 562.9 | 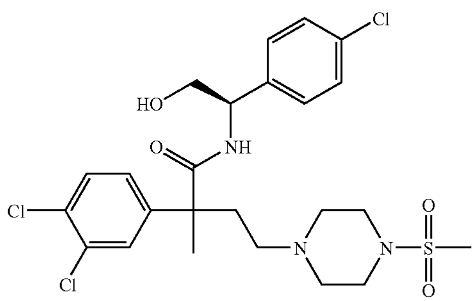 | N-[(R)-1-(4-Chloro-phenyl)-2-hydroxy-ethyl]-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (R)-2-Amino-2-(4-chloro-phenyl-ethanol (commercially available) | 564.3 |
| 131 | 562.9 | 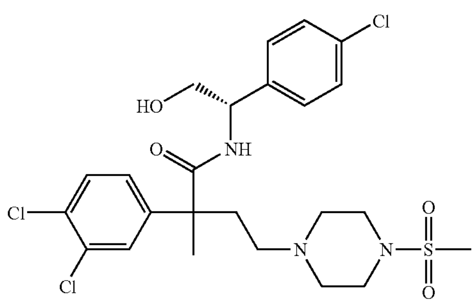 | N-[(S)-1-(4-Chloro-phenyl)-2-hydroxy-ethyl]-2-(3,4-dichloro-phenyl)-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (S)-2-Amino-2-(4-chloro-phenyl)-ethanol (commercially available) | 564.3 |
| 132 | 546.5 | 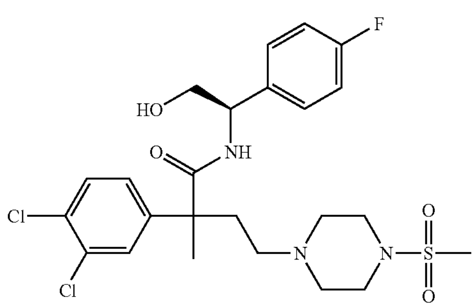 | 2-(3,4-Dichloro-phenyl)-N-[(R)-1-(4-fluoro-phenyl)-2-hydroxy-ethyl]-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (R)-2-Amino-2-(4-fluoro-phenyl)-ethanol (commercially available) | 548.3 |

TABLE 3-continued

| No | MW | structure | Systematic Name | starting materials | MW found MH+ |
|---|---|---|---|---|---|
| 133 | 546.5 | 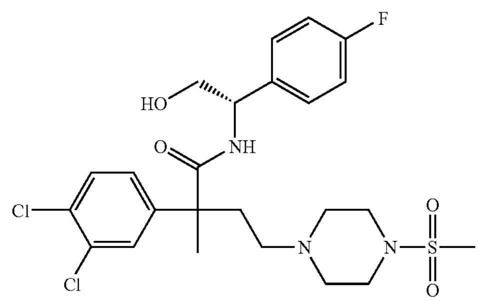 | 2-(3,4-Dichloro-phenyl)-N-[(S)-1-(4-fluoro-phenyl)-2-hydroxy-ethyl]-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and (S)-2-Amino-2-(4-fluoro-phenyl)-ethanol (commercially available) | 548.4 |
| 134 | 530.5 | 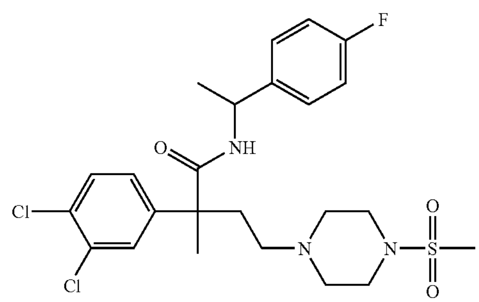 | 2-(3,4-Dichloro-phenyl)-N-[1-(4-fluoro-phenyl)-ethyl]-4-(4-methanesulfonyl-piperazin-1-yl)-2-methyl-butyramide | 2-(3,4-Dichloro-phenyl)-4-(4-methanesulfonyl-piperazin-1-yl)-2-methyl-butyric acid (intermediate 2) and 1-(4-Fluoro-phenyl)-ethylamine (commercially available) | 530.3 |
| 135 | 584.5 | 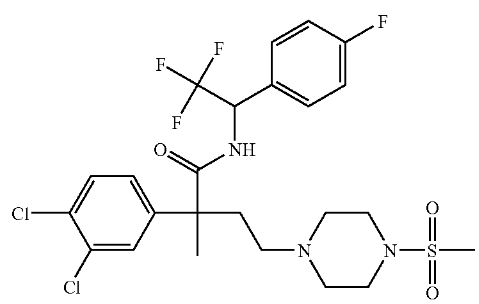 | 2-(3,4-Dichloro-phenyl)-4-(4-methanesulfonyl-piperazin-1-yl)-2-methyl-N-[2,2,2-trifluoro-1-(4-fluoro-phenyl)-ethyl]-butyramide | 2-(3,4-Dichloro-phenyl)-4-(4-methanesulfonyl-piperazin-1-yl)-2-methyl-butyric acid (intermediate 2) and 2,2,2-Trifluoro-1-(4-fluoro-phenyl)-ethylamine (commercially available) | 584.1 |
| 136 | 575.0 | 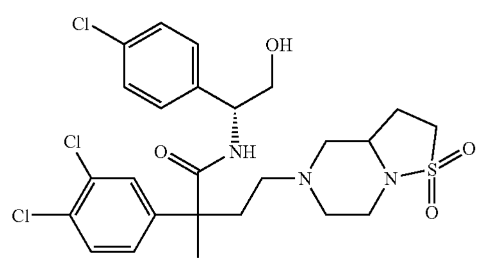 | N-[(R)-1-(4-Chloro-phenyl)-2-hydroxy-ethyl]-2-(3,4-dichloro-phenyl)-4-(1,1-dioxo-hexahydro-1$\lambda^6$-thia-5,7a-diaza-inden-5-yl)-2-methyl-butyramide | 2-(3,4-Dichloro-phenyl)-4-(1,1-dioxo-hexahydro-1lambda*6*-thia-5,7a-diaza-inden-5-yl)-2-methyl-butyric acid (intermediate 6) and (R)-2-Amino-2-(4-chloro-phenyl)-ethanol (commercially available) | 574.1 |
| 137 | 558.5 | 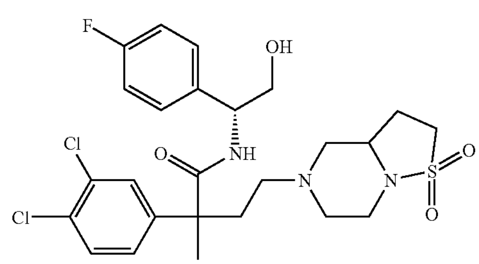 | 2-(3,4-Dichloro-phenyl)-(1,1-dioxo-hexahydro-1$\lambda^6$-thia-5,7a-diaza-inden-5-yl)-N-[(R)-1-(4-fluoro-phenyl)-2-hydroxy-ethyl]-2-methyl butyramide | 2-(3,4-Dichloro-phenyl)-4-(1,1-dioxo-hexahydro-1lambda*6*-thia-5,7a-diaza-inden-5-yl)-2-methyl-butyric acid (intermediate 6) and (R)-2-Amino-2-(4-fluoro-phenyl)-ethanol (commercially available) | 558 |

What is claimed is:
1. A compound of formula IA or IB wherein
R$^1$ is hydrogen or lower alkyl;
R$^2$ is hydrogen, fluoro, hydroxy or lower alkyl;
R$^3$ is hydrogen or lower alkyl;
R$^4$ is —CHR$^5$-A
  R$^5$ is hydrogen, lower alkyl, fluoro, CF$_3$, CH$_2$OH or cycloalkyl;
  A is aryl or heteroaryl, each of which is unsubstituted or substituted by (R$^6$)$_o$;
  R$^6$ is heteroaryl, lower alkyl, lower alkoxy, cyano, halogen, lower alkyl substituted by halogen, lower alkoxy substituted by halogen or NR$^7$R$^8$ wherein when o is more than one, each R$^6$ is the same or different;
  o is 1, 2 or 3;
  R$^7$, R$^8$ are each independently hydrogen or lower alkyl;
R$^9$ is lower alkyl;
R$^{10}$ is lower alkyl, lower alkoxy or halogen;
n is 1 or 2; and
m is 1 or 2;
or a pharmaceutically acceptable acid addition salt thereof.

2. A compound of claim 1, having formula IA.
3. The compound of claim 2, having formula IA-1 wherein
R$^1$ is hydrogen or lower alkyl;
R$^2$ is hydrogen, fluoro or lower alkyl;
R$^3$ is hydrogen or lower alkyl;
R$^4$ is —CHR$^5$-A
  R$^5$ is hydrogen, lower alkyl, fluoro, CF$_3$, CH$_2$OH or cycloalkyl;
  A is aryl or heteroaryl, each of which is unsubstituted or substituted by (R$^6$)$_o$;
  R$^6$ is heteroaryl, lower alkyl, lower alkoxy, cyano, halogen, lower alkyl substituted by halogen, lower alkoxy substituted by halogen or NR$^7$R$^8$ wherein when o is more than one, each R$^6$ is the same or different;
  o is 1, 2 or 3;
  R$^7$, R$^8$ are independently hydrogen or lower alkyl; and
n is 1 or 2;
or a pharmaceutically acceptable acid addition salt thereof.

4. The compound of claim 2, wherein n is 1.
5. The compound of claim 2, wherein R$^2$ is lower alkyl.
6. The compound claim 2, wherein R$^3$ is hydrogen or lower alkyl and R$^4$ is —CHR$^5$-A.
7. The compound of claim 6, wherein A is optionally substituted aryl.
8. The compound of claim 7, wherein A is optionally substituted phenyl.
9. The compound of claim 8, selected from the group consisting of N-(4-chloro-benzyl)-2-(3,4-dichloro-phenyl)-4-(4-methanesulfonyl-piperazin-1-yl)-2,N-dimethyl-butyramide, 2-(3,4-dichloro-phenyl)-N-(3-fluoro-4-trifluoromethyl-benzyl)-4-(4-methanesulfonyl-piperazin-1-yl)-2-methyl-butyramide, N-(3,4-dichloro-benzyl)-2-(3,4-dichloro-phenyl)-4-(4-methanesulfonyl-piperazin-1-yl)-2-methyl-butyramide, 2-(3,4-dichloro-phenyl)-4-(4-methanesulfonyl-piperazin-1-yl)-2,N-dimethyl-N-(4-methyl-benzyl)-butyramide, 2-(3,4-dichloro-phenyl)-4-(4-methanesulfonyl-piperazin-1-yl)-2-methyl-N-(4-trifluoromethyl-benzyl)-butyramide, 2-(3,4-dichloro-phenyl)-4-(4-methanesulfonyl-piperazin-1-yl)-2,N-dimethyl-N-(4-trifluoromethyl-benzyl)-butyramide, N-(4-chloro-benzyl)-2-(3,4-dichloro-phenyl)-4-(4-methanesulfonyl-piperazin-1-yl)-2-methyl-butyramide, N-[cyclopropyl-(4-methoxy-phenyl)-methyl]-2-(3,4-dichloro-phenyl)-4-((R)-4-methanesulfonyl-3-methyl-piperazin-1-yl)-2-methyl-butyramide, 2-(3,4-dichloro-phenyl)-N-(4-fluoro-3-trifluoromethyl-benzyl)-4-((R)-4-methanesulfonyl-3-methyl-piperazin-1-yl)-2,N-dimethyl-butyramide, and N-(3,5-bis-trifluoromethyl-benzyl)-2-(3,4-dichloro-phenyl)-4-((R)-4-methanesulfonyl-3-methyl-piperazin-1-yl)-2-methyl-butyramide.
10. The compound of claim 8, selected from the group consisting of 2-(3,4-dichloro-phenyl)-4-((R)-4-methanesulfonyl-3-methyl-piperazin-1-yl)-2,N-dimethyl-N-(4-methyl-benzyl)-butyramide, N-(4-chloro-3-trifluoromethyl-benzyl)-2-(3,4-dichloro-phenyl)-4-((R)-4-methanesulfonyl-3-methyl-piperazin-1-yl)-2,N-dimethyl-butyramide, 2-(3,4-dichloro-phenyl)-N-(3-fluoro-4-trifluoromethyl-benzyl)-4-((R)-4-methanesulfonyl-3-methyl-piperazin-1-yl)-2,N-dimethyl-butyramide, N-(3,4-dichloro-benzyl)-2-(3,4-dichloro-phenyl)-4-((R)-4-methanesulfonyl-3-methyl-piperazin-1-yl)-2,N-dimethyl-butyramide, N-(3,4-dichloro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-N-(3-difluoromethoxy-benzyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(4-trifluoromethyl-benzyl)-butyramide, 2-(3,4-dichloro-phenyl)-N-(2-fluoro-5-trifluoromethyl-benzyl)-4-((R)-4-methanesulfonyl-3-methyl-piperazin-1-yl)-2-methyl-butyramide, N-[1-(4-chloro-phenyl)-ethyl]-2-(3,4-dichloro-phenyl)-4-((R)-4-methanesulfonyl-3-methyl-piperazin-1-yl)-2-methyl-butyramide, and N-(2-chloro-benzyl)-2-(3,4- dichloro-phenyl)-4-((R)-4-methanesulfonyl-3-methyl-piperazin-1-yl)-2,N-dimethyl-butyramide.

11. The compound of claim 8, selected from the group consisting of 2-(3,4-dichloro-phenyl)-N-[1-(3,4-dichloro-phenyl)-ethyl]-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(3-trifluoromethoxy-benzyl)-butyramide, N-(4-chloro-3-fluoro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2-methyl-N-(4-trifluoromethoxy-benzyl)-butyramide, N-(4-chloro-3-trifluoromethyl-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-((R)-4-methanesulfonyl-3-methyl-piperazin-1-yl)-2,N-dimethyl-N-(4-trifluoromethyl-benzyl)-butyramide, N-(4-chloro-benzyl)-2-(3,4-dichloro-phenyl)-4-((R)-4-methanesulfonyl-3-methyl-piperazin-1-yl)-2,N-dimethyl-butyramide, 2-(3,4-dichloro-phenyl)-4-((R)-4-methanesulfonyl-3-methyl-piperazin-1-yl)-2,N-dimethyl-N-(3-trifluoromethyl-benzyl)-butyramide, N-[cyclopropyl-(4-methoxy-phenyl)-methyl]-2-(3,4-dichloro-phenyl)-4-((S)-4-methanesulfonyl-3-methyl-piperazin-1-yl)-2-methyl-butyramide, and 2-(3,4-dichloro-phenyl)-N-(4-fluoro-3-trifluoromethyl-benzyl)-4-((S)-4-methanesulfonyl-3-methyl-piperazin-1-yl)-2,N-dimethyl-butyramide.

12. The compound of claim 8, selected from the group consisting of N-(3,5-bis-trifluoromethyl-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2,N-dimethyl-N-(4-methyl-benzyl)-butyramide, N-(4-chloro-3-trifluoromethyl-benzyl)-2-(3,4-dichloro-phenyl)-4-((S)-4-methanesulfonyl-3-methyl-piperazin-1-yl)-2,N-dimethyl-butyramide, 2-(3,4-dichloro-phenyl)-N-(3-fluoro-4-trifluoromethyl-benzyl)-4-((S)-4-methanesulfonyl-3-methyl-piperazin-1-yl)-2,N-dimethyl-butyramide, N-(3,4-dichloro-benzyl)-2-(3,4-dichloro-phenyl)-4-((S)-4-methanesulfonyl-3-methyl-piperazin-1-yl)-2,N-dimethyl-butyramide, N-(3,4-dichloro-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2-methyl-N-(4-trifluoromethyl-benzyl)-butyramide, N-[1-(4-chloro-phenyl)-ethyl]-2-(3,4-dichloro-phenyl)-4-((S)-4-methanesulfonyl-3-methyl-piperazin-1-yl)-2-methyl-butyramide, 2-(3,4-dichloro-phenyl)-N-[1-(3,4-dichloro-phenyl)-ethyl]-4-((S)-4-methanesulfonyl-3-methyl-piperazin-1-yl)-2-methyl-butyramide, and N-(4-chloro-3-fluoro-benzyl)-2-(3,4-dichloro-phenyl)-4-((S)-4-methanesulfonyl-3-methyl-piperazin-1-yl)-2-methyl-butyramide.

13. The compound of claim 8, selected from the group consisting of 2-(3,4-dichloro-phenyl)-4-((S)-4-methanesulfonyl-3-methyl-piperazin-1-yl)-2-methyl-N-(4-trifluoromethoxy-benzyl)-butyramide, N-(4-chloro-3-trifluoromethyl-benzyl)-2-(3,4-dichloro-phenyl)-4-((S)-4-methanesulfonyl-3-methyl-piperazin-1-yl)-2-methyl-butyramide, 2-(3,4-dichloro-phenyl)-4-((S)-4-methanesulfonyl-3-methyl-piperazin-1-yl)-2,N-dimethyl-N-(4-trifluoromethyl-benzyl)-butyramide, N-(4-chloro-benzyl)-2-(3,4-dichloro-phenyl)-4-((S)-4-methanesulfonyl-3-methyl-piperazin-1-yl)-2,N-dimethyl-butyramide, 2-(3,4-dichloro-phenyl)-4-((S)-4-methanesulfonyl-3-methyl-piperazin-1-yl)-2,N-dimethyl-N-(3-trifluoromethyl-benzyl)-butyramide, (S)—N-(3,4-dichloro-benzyl)-2-(3,4-dichloro-phenyl)-4-((R)-4-methanesulfonyl-3-methyl-piperazin-1-yl)-2-methyl-butyramide, (R)—N-(3,4-dichloro-benzyl)-2-(3,4-dichloro-phenyl)-4-((R)-4-methanesulfonyl-3-methyl-piperazin-1-yl)-2-methyl-butyramide, 2-(3,4-dichloro-phenyl)-4-(4-methanesulfonyl-piperazin-1-yl)-2,N-dimethyl-N-(3-trifluoromethyl-benzyl)-butyramide, (R or S)-2-(3,4-dichloro-phenyl)-N—((R)-2-hydroxy-1-phenyl-ethyl)-4-(4-methanesulfonyl-piperazin-1-yl)-2-methyl-butyramide and N—[(R)-1-(4-chloro-phenyl)-2-hydroxy-ethyl]-2-(3,4-dichloro-phenyl)-4-(4-methanesulfonyl-piperazin-1-yl)-2-methyl-butyramide.

14. The compound of claim 2, wherein n is 2.

15. The compound of claim 14, selected from the group consisting of 2-(3,4-dichloro-phenyl)-N-(3-fluoro-4-trifluoromethyl-benzyl)-4-(4-methanesulfonyl-[1,4]diazepan-1-yl)-2-methyl-butyramide, 2-(3,4-dichloro-phenyl)-4-(4-methanesulfonyl-[1,4]diazepan-1-yl)-2,N-dimethyl-N-(4-trifluoromethyl-benzyl)-butyramide, N-(4-chloro-benzyl)-2-(3,4-dichloro-phenyl)-4-(4-methanesulfonyl-[1,4]diazepan-1-yl)-2,N-dimethyl-butyramide, N-(4-chloro-3-fluoro-benzyl)-2-(3,4-dichloro-phenyl)-4-(4-methanesulfonyl-[1,4]diazepan-1-yl)-2-methyl-butyramide, 2-(3,4-dichloro-phenyl)-N-(3-fluoro-benzyl)-4-(4-methanesulfonyl-[1,4]diazepan-1-yl)-2,N-dimethyl-butyramide, 2-(3,4-dichloro-phenyl)-4-(4-methanesulfonyl-[1,4]diazepan-1-yl)-2,N-dimethyl-N-(3-trifluoromethyl-benzyl)-butyramide, N-(3-chloro-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-(3-fluoro-4-methoxy-benzyl)-4-(4-methanesulfonyl-[1,4]diazepan-1-yl)-2,N-dimethyl-butyramide, 2-(3,4-dichloro-phenyl)-N-(4-fluoro-3-trifluoromethyl-benzyl)-4-(4-methanesulfonyl-[1,4]diazepan-1-yl)-2,N-dimethyl-butyramide, and 2-(3,4-dichloro-phenyl)-N-(4-difluoromethoxy-3-methoxy-benzyl)-4-(4-methanesulfonyl-[1,4]diazepan-1-yl)-2,N-dimethyl-butyramide.

16. The compound of claim 14, selected from the group consisting of 2-(3,4-dichloro-phenyl)-4-(4-methanesulfonyl-[1,4]diazepan-1-yl)-2,N-dimethyl-N-(4-methyl-benzyl)-butyramide, N-(4-chloro-3-trifluoromethyl-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-(3-fluoro-4-trifluoromethyl-benzyl)-4-(4-methanesulfonyl-[1,4]diazepan-1-yl)-2,N-dimethyl-butyramide, N-(3,4-dichloro-benzyl)-2-(3,4-dichloro-phenyl)-4-(4-methanesulfonyl-[1,4]diazepan-1-yl)-2,N-dimethyl-butyramide, N-(3,4-dichloro-benzyl)-2-(3,4-dichloro-phenyl)-4-(4-methanesulfonyl-[1,4]diazepan-1-yl)-2-methyl-butyramide, 2-(3,4-dichloro-phenyl)-4-(4-methanesulfonyl-[1,4]diazepan-1-yl)-2-methyl-N-(4-trifluoromethyl-benzyl)-butyramide, N-(2-chloro-benzyl)-2-(3,4-dichloro-phenyl)-4-(4-methanesulfonyl-[1,4]diazepan-1-yl)-2,N-dimethyl-butyramide, 2-(3,4-dichloro-phenyl)-N-[1-(3,4-dichloro-phenyl)-ethyl]-4-(4-methanesulfonyl-[1,4]diazepan-1-yl)-2-methyl-butyramide, and 2-(3,4-dichloro-phenyl)-4-(4-methanesulfonyl-[1,4]diazepan-1-yl)-2,N-dimethyl-N-(4-pyridin-4-yl-benzyl)-butyramide.

17. The compound of claim 1, having formula IB.

18. The compound of claim 17, wherein n is 1.

19. The compound of claim 17, wherein $R^2$ is lower alkyl.

20. The compound of claim 17, wherein $R^3$ is hydrogen or lower alkyl and $R^4$ is —$CHR^5$-A.

21. The compound of claim 20, wherein A is optionally substituted aryl.

22. The compound of claim 21, wherein A is optionally substituted phenyl.

23. The compound of claim 22, selected from the group consisting of N—[(R)-1-(4-chloro-phenyl)-2-hydroxy-ethyl]-2-(3,4-dichloro-phenyl)-4-(1,1-dioxo-hexahydro-1λ⁶-thia-5,7a-diaza-inden-5-yl)-2-methyl-butyramide and 2-(3,4-dichloro-phenyl)-4-(1,1-dioxo-hexahydro-1λ⁶-thia-5,7a-diaza-inden-5-yl)-N—[(R)-1-(4-fluoro-phenyl)-2-hydroxy-ethyl]-2-methyl-butyramide.

24. A pharmaceutical composition comprising a therapeutically effective amount of a compound of formula IA or IB

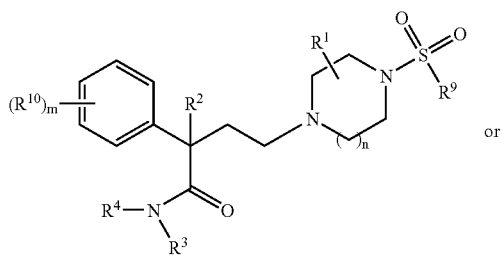

IA

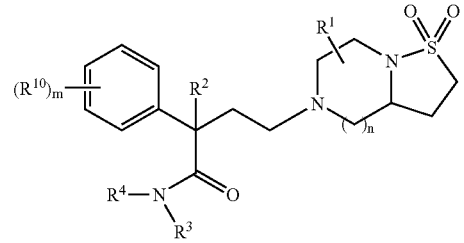

IB wherein
$R^1$ is hydrogen or lower alkyl;
$R^2$ is hydrogen, fluoro, hydroxy or lower alkyl;
$R^3$ is hydrogen or lower alkyl;
$R^4$ is —$CHR^5$-A
$R^5$ is hydrogen, lower alkyl, fluoro, $CF_3$, $CH_2OH$ or cycloalkyl;
A is aryl or heteroaryl, each of which is unsubstituted or substituted by $(R^6)_o$;
$R^6$ is heteroaryl, lower alkyl, lower alkoxy, cyano, halogen, lower alkyl substituted by halogen, lower alkoxy substituted by halogen or $NR^7R^8$ wherein when o is more than one, each $R^6$ is the same or different;
o is 1, 2 or 3;
$R^7$, $R^8$ are each independently hydrogen or lower alkyl;
$R^9$ is lower alkyl;
$R^{10}$ is lower alkyl, lower alkoxy or halogen;
n is 1 or 2; and
m is 1 or 2;
or a pharmaceutically acceptable acid addition salt thereof and a pharmaceutically acceptable carrier.

* * * * *